US009487783B2

(12) United States Patent
Bhat et al.

(10) Patent No.: US 9,487,783 B2
(45) Date of Patent: Nov. 8, 2016

(54) TARGETING MICRORNAS FOR METABOLIC DISORDERS

(71) Applicant: Regulus Therapeutics Inc., San Diego, CA (US)

(72) Inventors: Balkrishen Bhat, Cambridge, MA (US); Neil W. Gibson, San Diego, CA (US); Diedre MacKenna, San Diego, CA (US); Brandee Wagner, La Jolla, CA (US); David P. Bartel, Brookline, MA (US)

(73) Assignee: Regulus Therapeutics Inc., San Diego, CA (US)

( * ) Notice: Subject to any disclaimer, the term of this patent is extended or adjusted under 35 U.S.C. 154(b) by 0 days.

(21) Appl. No.: 14/819,648

(22) Filed: Aug. 6, 2015

(65) Prior Publication Data

US 2016/0046940 A1    Feb. 18, 2016

Related U.S. Application Data

(60) Provisional application No. 62/143,434, filed on Apr. 6, 2015, provisional application No. 62/062,749, filed on Oct. 10, 2014, provisional application No. 62/034,739, filed on Aug. 7, 2014.

(51) Int. Cl.
| | |
|---|---|
| *C12N 15/11* | (2006.01) |
| *C12N 15/113* | (2010.01) |
| *A61K 31/7088* | (2006.01) |
| *A61K 45/06* | (2006.01) |

(52) U.S. Cl.
CPC ......... *C12N 15/113* (2013.01); *A61K 31/7088* (2013.01); *A61K 45/06* (2013.01); *C12N 2310/113* (2013.01); *C12N 2310/141* (2013.01); *C12N 2310/315* (2013.01); *C12N 2310/3231* (2013.01); *C12N 2310/345* (2013.01); *C12N 2310/346* (2013.01); *C12N 2310/351* (2013.01); *C12N 2310/51* (2013.01)

(58) Field of Classification Search
CPC ...................................... C12N 15/113
USPC ................................ 514/6.5, 44 A
See application file for complete search history.

(56) References Cited

U.S. PATENT DOCUMENTS

| | | | |
|---|---|---|---|
| 8,404,659 B2 | 3/2013 | Kauppinen et al. | |
| 8,592,388 B2 | 11/2013 | Stoffel et al. | |
| 8,877,730 B2 | 11/2014 | Stoffel et al. | |
| 9,243,249 B2 | 1/2016 | Stoffel et al. | |

(Continued)

FOREIGN PATENT DOCUMENTS

| | | |
|---|---|---|
| CN | 101121934 B | 12/2011 |
| WO | WO 2005/013901 A2 | 2/2005 |

(Continued)

OTHER PUBLICATIONS

International Search Report for PCT/US2015/043926, dated Nov. 9, 2015.

(Continued)

*Primary Examiner* — Jezia Riley
(74) *Attorney, Agent, or Firm* — McNeill Baur PLLC

(57) ABSTRACT

Described herein are compounds comprising modified oligonucleotides that are complementary to miR-103 and/or miR-107 and methods of treating diseases and disorders using the compounds.

8 Claims, 18 Drawing Sheets

(56) References Cited

U.S. PATENT DOCUMENTS

| | | |
|---|---|---|
| 2006/0185027 A1 | 8/2006 | Bartel et al. |
| 2015/0038550 A1 | 2/2015 | Stoffel et al. |
| 2015/0073124 A1 | 3/2015 | Ohgi et al. |
| 2016/0208259 A1 | 7/2016 | Stoffel et al. |

FOREIGN PATENT DOCUMENTS

| | | |
|---|---|---|
| WO | WO 2005/118806 A2 | 12/2005 |
| WO | WO 2006/020768 A2 | 2/2006 |
| WO | WO 2006/078278 A2 | 7/2006 |
| WO | WO 2006/137941 A2 | 12/2006 |
| WO | WO 2007/021896 A2 | 2/2007 |
| WO | WO 2007/027894 A2 | 3/2007 |
| WO | WO 2007/090073 A2 | 8/2007 |
| WO | WO 2007/112753 A2 | 10/2007 |
| WO | WO 2007/112754 A2 | 10/2007 |
| WO | WO 2009/043353 A2 | 4/2009 |
| WO | WO 2009/073809 A2 | 6/2009 |
| WO | 2010/133970 | 11/2010 |
| WO | WO 2010/144485 A1 | 12/2010 |
| WO | WO 2011/117353 A1 | 9/2011 |
| WO | WO 2012/135152 A1 | 10/2012 |
| WO | WO 2013/033230 A1 | 3/2013 |
| WO | WO 2013/040429 A1 | 3/2013 |
| WO | 2013/133221 | 9/2013 |
| WO | WO 2013/192486 A1 | 12/2013 |
| WO | WO 2013/192576 A2 | 12/2013 |
| WO | WO 2014/043544 A1 | 3/2014 |
| WO | WO 2014/048441 A1 | 4/2014 |
| WO | WO 2014/076195 A1 | 5/2014 |
| WO | WO2014/118267 A1 | 8/2014 |
| WO | WO 2014/118272 A1 | 8/2014 |
| WO | WO 2014/179445 A1 | 11/2014 |
| WO | WO 2014/179620 A1 | 11/2014 |
| WO | WO 2015/113922 A1 | 8/2015 |

OTHER PUBLICATIONS

Mao, Y: et al., "MicroRNAs as Pharmacological Targets in Diabetes," Pharmacological Research, vol. 75, Sep. 1, 2013, pp. 37-47.

Li, Z. et al., "Therapeutic Targeting of MicroRNAs: Current Status and Future Challenges," Nature Review, Drug Discovery, vol. 13, No. 8, Jul. 11, 2014, pp. 622-638.

Sayed, D. et al., "MicroRNA-21 Targets Sprouty2 and Promotes Cellular Outgrowths," Molecular Biology of the Cell, American Society for Cell Biology, vol. 19, No. 8, Aug. 2008, pp. 3272-3282.

Regulus Therapeutics Inc., "RG-125(AZD4076), a microRNA Therapeutic Targeting microRNA-103/107 Being Developed for the Treatment of NASH in Patients with Type 2 Diabetes/Pre-Diabetes, Enters Phase I Clinical Development," Press Release, Regulus Therapeutics Inc., Dec. 18, 2015, 2 pages.

Sundqvist et al., "Preclinical pharmacokinetics-pharmacodynamics modelling to guide first-time-in-human studies with the anti-miR-103/107, RG-125 (AZD4076)," Abstract 824, European Association for the Study of Diabetes meeting, Jul. 2015, 1 page.

Sundqvist et al., "Preclinical pharmacokinetics-pharmacodynamics modelling to guide first-time-in-human studies with the anti-miR-103/107, RG-125 (AZD4076)," Abstract 824, European Association for the Study of Diabetes meeting, Sep. 15, 2015, 1 page.

Turnbull, "Antagonizing miR-103/107 to treat metabolic disease: RG-125/AZD4076 is a first-in-modality clinical candidate," Oral presentation, Oligonucleotide Therapeutic Society, Oct. 15, 2015, 21 pages.

Wagner et al., "RG-125 (AZD4076): clinical candidate with a novel modality to treat insulin resistance through inhibiting miR-103/107," Abstract 823, European Association for the Study of Diabetes meeting, Jul. 2015, 1 page.

Wagner et al., "RG-125 (AZD4076): clinical candidate with a novel modality to treat insulin resistance through inhibiting miR-103/107," Poster presentation, European Association for the Study of Diabetes meeting, Sep. 15, 2015, 1 page.

Bhat et al., "RG-101, a GalNAc-conjugated anti-miR Employing a Unique Mechanism of Action by Targeting Host Factor MicroRNA-122 (miR-122), Demonstrates Potent Activity and Reduction of HCV in Preclinical Studies," 64th Annual Meeting AASLD, Washington D.C., Nov. 3, 2013, 1 page.

Esau et al., "MicroRNA-143 Regulates Adipocyte Differentiation," Journal of Biological Chemistry, 279(50): 52361-52365, 2004.

Horwich et al., "Design and delivery of antisense oligonucleotides to block microRNA function in cultured *Drosophila* and human cells," Nature Protocols, 3:1537-1549, 2008.

Karskela et al., "Synthesis and Cellular Uptake of Fluorescently Labeled Multivalent Hyaluronan Disaccharide Conjugates of Oligonucleotide Phosphorothioates," Bioconjugate Chem, 19:2549-2558, 2008.

Katajisto et al., "Solid-Phase Synthesis of Multiantennary Oligonucleotide Glycoconjugates Utilizing On-Support Oximation," Bioconjugate Chem., 15:890-896, 2004.

Leriche et al., "Cleavable linkers in chemical biology," Bioorg, Med, Chem, 20:571-582, 2012.

Liu et al., "Sustained Improvement in Glucose Control Comparable to Rosiglitazone in DIO Mice after Subcutaneous Administration of Anti-miR-107 Oligonucleotide," Keystone Symposia: Pathogenesis of Diabetes: Emerging Insights into Molecular Mechanisms, Jan. 29-Feb. 3, 2012, 1 page.

Lu et al., "A single anti-microRNA antisense oligodeoxyribonucleotide (AMO) targeting multiple microRNAs offer an improved approach for microRNA interference," Nucleic Acids Research, vol. 37, No. 3, e24, 2009, 10 pages.

Maier et al., "Synthesis of Antisense Oligonucleotides Conjugated to a Multivalent Carbohydrate Cluster for Cellular Targeting," Bioconjugate Chem., 14:18-29, 2003.

Regulus Therapeutics Inc., "Press Release—MicroRNA: The Year in Review and a Look Ahead," Dec. 9, 2009, 3 pages.

Regulus Therapeutics Inc., "Press Release—Regulus Presents New Preclinical Data on Multiple Programs and Provides Portfolio Overview at 10th Annual Oligonucleotide Therapeutics Society (OTS) Meeting," Oct. 14, 2014, 3 pages.

Regulus Therapeutics Inc., "Press Release—RG-125 (AZD4076), a microRNA Therapeutic Targeting microRNA-103/107 for the Treatment of NASH in Patients with Type 2 Diabetes/Pre-Diabetes, Selected as Clinical Candidate by AstraZeneca," Apr. 7, 2015, 3 pages.

Regulus Therapeutics Inc., "Webinar Series—MicroRNA: The Year in Review and a Look Ahead," Dec. 14, 2009, 42 pages.

Spinelli et al., "Glycoclusters on oligonucleotide and PNA scaffolds: synthesis and applications," Chem. Soc. Rev., 42:4557-4573, 2013.

Trajkovski et al., "MicroRNAs 103 and 107 regulate insulin sensitivity," Nature, 474:649-654, 2011.

Tripathi et al., "The Nuclear-Retained Noncoding RNA MALAT1 Regulates Alternative Splicing by Modulating SR Splicing Factor Phosphorylation," Molecular Cell, 39:925-938, 2010.

Wagner et al., "Anti-Diabetic Activity of miR-103/107 Anti-miRs," Poster Presentation at Oligonucleotide Therapeutics Society meeting, Oct. 12-15, 2014, 1 page.

Xanthopoulos, "Transcript of Oral Presentation, 12th Annual Needham Healthcare Conference," May 1, 2013, 9 pages.

Xu et al., "Effects of Multiple-target Anti-microRNA Antisense Oligodeoxynucleotides on Proliferation and Migration of Gastric Cancer Cells," Asian Pacific Journal of Cancer Prevention, 13, 3203-3207, 2012.

Zatsepin et al., "Synthesis and Applications of Oligonucleotide—Carbohydrate Conjugates," Chemistry & Biodiversity, 1:1401-1417, 2004.

(I)

(II)

(III)

SEQUENCE LISTING

```
<160> NUMBER OF SEQ ID NOS: 24

<210> SEQ ID NO 1
<211> LENGTH: 23
<212> TYPE: RNA
<213> ORGANISM: homo sapiens

<400> SEQUENCE: 1
agcagcauug uacagggcua uga                                          23

<210> SEQ ID NO 2
<211> LENGTH: 23
<212> TYPE: RNA
<213> ORGANISM: homo sapiens

<400> SEQUENCE: 2
agcagcauug uacagggcua uca                                          23

<210> SEQ ID NO 3
<211> LENGTH: 78
<212> TYPE: RNA
<213> ORGANISM: homo sapiens

<400> SEQUENCE: 3
uacugcccuc ggcuucuuua cagugcugcc uuguugcaua uggaucaagc agcauuguac  60
agggcuauga aggcauug                                                78

<210> SEQ ID NO 4
<211> LENGTH: 78
<212> TYPE: RNA
<213> ORGANISM: homo sapiens

<400> SEQUENCE: 4
```

```
uugugcuuuc agcuucuuua cagugcugcc uuguagcauu caggucaagc agcauuguac    60
agggcuauga aagaacca                                                 78

<210> SEQ ID NO 5
<211> LENGTH: 81
<212> TYPE: RNA
<213> ORGANISM: homo sapiens

<400> SEQUENCE: 5
cucucugcuu ucagcuucuu uacaguguug ccuugguggca uggaguucaa gcagcauugu    60
acagggcuau caaagcacag a                                              81

<210> SEQ ID NO 6
<211> LENGTH: 10
<212> TYPE: RNA
<213> ORGANISM: homo sapiens

<400> SEQUENCE: 6
caaugcugca                                                           10

<210> SEQ ID NO 7
<211> LENGTH: 22
<212> TYPE: RNA
<213> ORGANISM: artificial sequence
<220> FEATURE:
<223> OTHER INFORMATION: Modified oligonucleotide

<400> SEQUENCE: 7
caaugcugca aacaaugcug ca                                             22

<210> SEQ ID NO 8
<211> LENGTH: 10
<212> TYPE: RNA
<213> ORGANISM: artificial sequence
<220> FEATURE:
<223> OTHER INFORMATION: Modified oligonucleotide

<400> SEQUENCE: 8
caaugcugcc                                                           10

<210> SEQ ID NO 9
<211> LENGTH: 22
<212> TYPE: RNA
<213> ORGANISM: artificial sequence
<220> FEATURE:
<223> OTHER INFORMATION: Modified oligonucleotide

<400> SEQUENCE: 9
caaugcugcc aacaaugcug cc                                             22

<210> SEQ ID NO 10
<211> LENGTH: 10
<212> TYPE: RNA
```

```
<213> ORGANISM: artificial sequence
<220> FEATURE:
<223> OTHER INFORMATION: Modified oligonucleotide

<400> SEQUENCE: 10
caaugcugcg                                                              10

<210> SEQ ID NO 11
<211> LENGTH: 22
<212> TYPE: RNA
<213> ORGANISM: artificial sequence
<220> FEATURE:
<223> OTHER INFORMATION: Modified oligonucleotide

<400> SEQUENCE: 11
caaugcugcg aacaaugcug cg                                                22

<210> SEQ ID NO 12
<211> LENGTH: 23
<212> TYPE: RNA
<213> ORGANISM: homo sapiens

<400> SEQUENCE: 12
auagcagcac auaauggutu gug                                               23

<210> SEQ ID NO 13
<211> LENGTH: 22
<212> TYPE: RNA
<213> ORGANISM: homo sapiens

<400> SEQUENCE: 13
uagcagcaca ucaugguuua ca                                                22

<210> SEQ ID NO 14
<211> LENGTH: 22
<212> TYPE: RNA
<213> ORGANISM: homo sapiens

<400> SEQUENCE: 14
uagcagcacg uaaauauugg cg                                                22

<210> SEQ ID NO 15
<211> LENGTH: 22
<212> TYPE: RNA
<213> ORGANISM: homo sapiens

<400> SEQUENCE: 15
uagcagcaca gaaauauugg cc                                                22
```

```
<210> SEQ ID NO 16
<211> LENGTH: 21
<212> TYPE: RNA
<213> ORGANISM: homo sapiens

<400> SEQUENCE: 16
cagcagcaca cugugguuug u                                              21

<210> SEQ ID NO 17
<211> LENGTH: 23
<212> TYPE: RNA
<213> ORGANISM: homo sapiens

<400> SEQUENCE: 17
uagcagcggg aacaguucug cag                                            23

<210> SEQ ID NO 18
<211> LENGTH: 22
<212> TYPE: RNA
<213> ORGANISM: homo sapiens

<400> SEQUENCE: 18
cagcagcaau ucauguuuug aa                                             22

<210> SEQ ID NO 19
<211> LENGTH: 19
<212> TYPE: RNA
<213> ORGANISM: homo sapiens

<400> SEQUENCE: 19
aagcagcugc cucugaggc                                                 19

<210> SEQ ID NO 20
<211> LENGTH: 21
<212> TYPE: DNA
<213> ORGANISM: artificial sequence
<220> FEATURE:
<223> OTHER INFORMATION: Modified oligonucleotide

<400> SEQUENCE: 20
atagccctgt acaatgctgc t                                              21

<210> SEQ ID NO 21
<211> LENGTH: 21
<212> TYPE: DNA
<213> ORGANISM: artificial sequence
<220> FEATURE:
<223> OTHER INFORMATION: Modified oligonucleotide
```

```
<400> SEQUENCE: 21
atagccctgt acaatgctgc a                                             21

<210> SEQ ID NO 22
<211> LENGTH: 21
<212> TYPE: DNA
<213> ORGANISM: artificial sequence
<220> FEATURE:
<223> OTHER INFORMATION: Modified oligonucleotide

<400> SEQUENCE: 22
atagccctgt acaatgctgc c                                             21

<210> SEQ ID NO 23
<211> LENGTH: 23
<212> TYPE: DNA
<213> ORGANISM: artificial sequence
<220> FEATURE:
<223> OTHER INFORMATION: Modified oligonucleotide

<400> SEQUENCE: 23
tgatagccct gtacaatgct gct                                           23

<210> SEQ ID NO 24
<211> LENGTH: 9
<212> TYPE: DNA
<213> ORGANISM: artificial sequence
<220> FEATURE:
<223> OTHER INFORMATION: Modified oligonucleotide

<400> SEQUENCE: 24 caatgctgc                                                            9
```

TARGETING MICRORNAS FOR METABOLIC DISORDERS

This application claims the benefit of priority of U.S. Provisional Application No. 62/034,739, filed Aug. 7, 2014; 62/062,749, filed Oct. 10, 2014; and 62/143,434, filed Apr. 6, 2015; each of which is incorporated by reference herein in its entirety for any purpose.

SEQUENCE LISTING

This application is being filed electronically via EFS-Web and includes an electronically submitted sequence listing in .txt format. The .txt file contains a sequence listing entitled "2015-08-06_01138-0019-00US_SeqListing.txt" was created on Aug. 5, 2015 and is 4,596 bytes in size. The sequence listing contained in this .txt file is part of the specification and is hereby incorporated by reference herein in its entirety.

FIELD OF INVENTION

Provided herein are methods and compositions for the treatment of metabolic disorders.

DESCRIPTION OF RELATED ART

MicroRNAs (miRNAs), also known as "mature miRNA" are small (approximately 18-24 nucleotides in length), non-coding RNA molecules encoded in the genomes of plants and animals. In certain instances, highly conserved, endogenously expressed miRNAs regulate the expression of genes by binding to the 3'-untranslated regions (3'-UTR) of specific mRNAs. More than 1000 different miRNAs have been identified in plants and animals. Certain mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662).

Families of miRNAs can be characterized by nucleotide identity at positions 2-8 of the miRNA, a region known as the seed sequence. Lewis et al. describe several miRNA families, as well as miRNA superfamilies, which are characterized by related seed sequences (Lewis et al. Cell. 2005, 120(1):15-20). MicroRNAs miR-103 and miR-107 are family members, as they have identical seed regions. Thus these two microRNAs will regulate similar, if not identical, sets of target genes.

Inhibiting miR-103 and miR-107 has been shown to reduce blood glucose levels and improve insulin sensitivity. See, e.g., PCT Publication No. 2010/133970 A1.

SUMMARY OF INVENTION

Embodiment 1

A compound comprising a modified oligonucleotide having the structure:

[oligo1]-[x-N]$_m$-x-[oligo2]

wherein:
oligo1 consists of 7 to 15 linked nucleosides and has a nucleobase sequence that is complementary to the nucleobase sequence of miR-103 and/or miR-107 with no more than 1 mismatch;
oligo2 consists of 7 to 15 linked nucleosides and has a nucleobase sequence that is complementary to the nucleobase sequence of miR-103 and/or miR-107 with no more than 1 mismatch;
each x is independently selected from a phosphodiester bond and a phosphorothioate bond;
each N is independently selected from a modified nucleoside and an unmodified nucleoside;
m is an integer from 1 to 5;
wherein at least one x is a phosphodiester bond.

Embodiment 2

The compound of embodiment 1, wherein the modified oligonucleotide consists of 15 to 32, 15 to 30, 15 to 28, 15 to 26, 15 to 24, or 15 to 22, or 15 to 20 nucleosides.

Embodiment 3

The compound of embodiment 1 or embodiment 2, wherein oligo1 has a nucleobase sequence that is 100% complementary to the nucleobase sequence of miR-103 and/or miR-107.

Embodiment 4

The compound of any one of the preceding embodiments, wherein oligo1 has a nucleobase sequence that is complementary to at least 6, at least 7, or 8 nucleotides of the seed region of miR-103 and/or miR-107.

Embodiment 5

The compound of any one of the preceding embodiments, wherein oligo2 has a nucleobase sequence that is 100% complementary to the nucleobase sequence of miR-103 and/or miR-107.

Embodiment 6

The compound of any one of the preceding embodiments, wherein oligo2 has a nucleobase sequence that is complementary to at least 6, at least 7, or 8 nucleotides of the seed region of miR-103 and/or miR-107.

Embodiment 7

The compound of any one of embodiments 1, 2, 4, and 6, wherein oligo1 has a mismatch with the first nucleotide at the 5' end of miR-103 and miR-107.

Embodiment 8

The compound of any one of embodiments 1, 2, 4, 6, and 7, wherein oligo2 has a mismatch with the first nucleotide at the 5' end of miR-103 and miR-107.

Embodiment 9

The compound of any one of the preceding embodiments, wherein at least 2 x are phosphodiester bonds.

Embodiment 10

The compound of any one of the preceding embodiments, wherein each x is a phosphodiester bond.

Embodiment 11

The compound of any one of the preceding embodiments, wherein at least one N is an unmodified nucleoside.

Embodiment 12

The compound of any one of the preceding embodiments, wherein each N is an unmodified nucleoside.

Embodiment 13

The compound of any one of the preceding embodiments, wherein m is 1, 2, 3, 4, or 5.

Embodiment 14

The compound of any one of the preceding embodiments, wherein m is 1, 2, or 3.

Embodiment 15

A compound comprising a modified oligonucleotide having the structure:

[oligo1]-[x-N]$_m$-x-[oligo2]-[x-N]$_m$-x-[oligo3]

wherein:
oligo1 consists of 7 to 15 linked nucleosides and has a nucleobase sequence that is complementary to the nucleobase sequence of miR-103 and/or miR-107 with no more than 1 mismatch;
oligo2 consists of 7 to 15 linked nucleosides and has a nucleobase sequence that is complementary to the nucleobase sequence of miR-103 and/or miR-107 with no more than 1 mismatch;
oligo3 consists of 7 to 15 linked nucleosides and has a nucleobase sequence that is complementary to the nucleobase sequence of a third microRNA with no more than 1 mismatch;
each x is independently selected from a phosphodiester bond and a phosphorothioate bond;
each N is independently selected from a modified nucleoside and an unmodified nucleoside;
each m is independently an integer from 1 to 5;
wherein at least one x is a phosphodiester bond.

Embodiment 16

The compound of embodiment 15, wherein at least one x between oligo1 and oligo2 is a phosphodiester bond and at least one x between oligo2 and oligo3 is a phosphodiester bond.

Embodiment 17

The compound of embodiment 15 or embodiment 16, wherein the modified oligonucleotide consists of 23 to 55, 23 to 50, 23 to 45, 23 to 40, 23 to 35, 23 to 30, or 23 to 26 nucleosides.

Embodiment 18

The compound of any one of embodiments 15 to 17, wherein oligo1 has a nucleobase sequence that is 100% complementary to the nucleobase sequence of miR-103 and/or miR-107.

Embodiment 19

The compound of any one of embodiments 15 to 18, wherein oligo1 has a nucleobase sequence that is complementary to at least 6, at least 7, or 8 nucleotides of the seed region of miR-103 and/or miR-107.

Embodiment 20

The compound of any one of embodiments 15 to 19, wherein oligo2 has a nucleobase sequence that is 100% complementary to the nucleobase sequence of miR-103 and/or miR-107.

Embodiment 21

The compound of any one of embodiments 15 to 20, wherein oligo2 has a nucleobase sequence that is complementary to at least 6, at least 7, or 8 nucleotides of the seed region of miR-103 and/or miR-107.

Embodiment 22

The compound of any one of embodiments 15 to 21, wherein oligo3 has a nucleobase sequence that is 100% complementary to the nucleobase sequence of the third microRNA.

Embodiment 23

The compound of any one of embodiments 15 to 22, wherein oligo3 has a nucleobase sequence that is complementary to at least 6, at least 7, or 8 nucleotides of the seed region of the third microRNA.

Embodiment 24

The compound of any one of embodiments 15 to 23, wherein the third microRNA is miR-103 and/or miR-107

Embodiment 25

The compound of any one of the preceding embodiments, wherein at least 4 x are phosphodiester bonds.

Embodiment 26

The compound of embodiment 23, wherein at least 2 x between oligo1 and oligo2 are phosphodiester bonds and at least 2 x between oligo2 and oligo3 are phosphodiester bonds.

Embodiment 27

The compound of any one of the preceding embodiments, wherein each x is a phosphodiester bond.

Embodiment 28

The compound of any one of the preceding embodiments, wherein at least one N is an unmodified nucleoside.

Embodiment 29

The compound of embodiment 28, wherein at least one N between oligo1 and oligo2 is an unmodified nucleoside, and at least one N between oligo2 and oligo3 is an unmodified nucleoside.

Embodiment 30

The compound of any one of the preceding embodiments, wherein each N is an unmodified nucleoside.

Embodiment 31

The compound of any one of the preceding embodiments, wherein each m is independently selected from 1, 2, 3, 4, and 5.

Embodiment 32

The compound of any one of the preceding embodiments, wherein each m is independently selected from 1, 2, or 3.

Embodiment 33

The compound of any one of embodiments 15 to 32, wherein oligo1 has a mismatch with the first nucleotide at the 5' end of miR-103 and miR-107 and/or oligo2 has a mismatch with the first nucleotide at the 5' end of miR-103 and miR-107, and/or oligo3 has a mismatch with the first nucleotide at the 5' end of miR-103 and miR-107.

Embodiment 34

The compound of any one of the preceding embodiments, wherein the compound comprises a conjugate moiety linked to the 5' terminus or the 3' terminus of the modified oligonucleotide, or both.

Embodiment 35

The compound of embodiment 34, wherein the compound comprises a conjugate moiety linked to the 3' terminus of the modified oligonucleotide.

Embodiment 36

The compound of embodiment 34 or embodiment 35, wherein the compound comprises a conjugate moiety linked to the 5' terminus of the modified oligonucleotide.

Embodiment 37

The compound of embodiment 34, wherein the compound comprises a conjugate moiety linked to the 5' terminus or the 3' terminus of the modified oligonucleotide, but not both.

Embodiment 38

The compound of embodiment 34, wherein the compound comprises a first conjugate moiety linked to the 3' terminus of the modified oligonucleotide and a second conjugate moiety linked to the 5' terminus of the modified oligonucleotide.

Embodiment 39

The compound of any one of embodiments 34 to 38, wherein the conjugate moiety comprises at least one ligand selected from a carbohydrate, cholesterol, a lipid, a phospholipid, an antibody, a lipoprotein, a hormone, a peptide, a vitamin, a steroid, and a cationic lipid.

Embodiment 40

The compound of any one of embodiments 34 to 39, wherein the compound has the structure:

$L_n$-linker-MO wherein each L is, independently, a ligand and n is from 1 to 10; and MO is the modified oligonucleotide.

Embodiment 41

The compound of any of one embodiments 34 to 39, wherein the compound has the structure:

$L_n$-linker-X-MO wherein each L is, independently, a ligand and n is from 1 to 10; X is a phosphodiester linkage or a phosphorothioate linkage; and MO is the modified oligonucleotide.

Embodiment 42

The compound of any one of embodiments 34 to 39, wherein the compound has the structure:

$L_n$-linker-$X_1$—$N_m$—$X_2$-MO wherein each L is, independently, a ligand and n is from 1 to 10; each N of $N_m$ is, independently, a modified or unmodified nucleoside and m is from 1 to 5; $X_1$ and $X_2$ are each, independently, a phosphodiester linkage or a phosphorothioate linkage; and MO is the modified oligonucleotide.

Embodiment 43

The compound of any one of embodiments 34 to 39, wherein the compound has the structure:

$L_n$-linker-X—$N_m$—Y-MO wherein each L is, independently, a ligand and n is from 1 to 10; each N of $N_m$ is, independently, a modified or unmodified nucleoside and m is from 1 to 5; X is a phosphodiester linkage or a phosphorothioate linkage; Y is a phosphodiester linkage; and MO is the modified oligonucleotide.

Embodiment 44

The compound of any one of embodiments 34 to 39, wherein the compound has the structure:

$L_n$-linker-Y—$N_m$—Y-MO wherein each L is, independently, a ligand and n is from 1 to 10; each N of $N_m$ is, independently, a modified or unmodified nucleoside and m is from 1 to 5; each Y is a phosphodiester linkage; and MO is the modified oligonucleotide.

Embodiment 45

The compound of any of embodiments 40 to 44, wherein if n is greater than 1, $L_n$-linker has the structure:

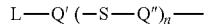

wherein each L is, independently, a ligand; n is from 1 to 10; S is a scaffold; and Q' and Q" are, independently, linking groups.

Embodiment 46

The compound of embodiment 45, wherein Q' and Q" are each independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

Embodiment 47

The compound of embodiment 45 or 46, wherein the scaffold links 2, 3, 4, or 5 ligands to a modified oligonucleotide.

Embodiment 48

The compound of embodiment 47, wherein the scaffold links 3 ligands to a modified oligonucleotide.

Embodiment 49

The compound of any one of embodiments 40 to 48, wherein the compound has the structure:

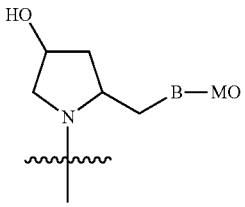

wherein:
B is selected from —O—, —S—, —N($R^N$)—, —Z—P(Z')(Z")O—, —Z—P(Z')(Z")O—$N_m$—X—, and —Z—P(Z')(Z")O—$N_m$—Y—;
MO is the modified oligonucleotide;
$R^N$ is selected from H, methyl, ethyl, propyl, isopropyl, butyl, and benzyl;
Z, Z', and Z" are each independently selected from O and S;
each N of $N_m$ is, independently, a modified or unmodified nucleoside;
m is from 1 to 5;
X is selected from a phosphodiester linkage and a phosphorothioate linkage;
Y is a phosphodiester linkage; and
the wavy line indicates the connection to the rest of the linker and ligand(s).

Embodiment 50

The compound of any one of embodiments 41 to 49, wherein X is a phosphodiester linkage.

Embodiment 51

The compound of any one of embodiments 40 to 50, wherein n is from 1 to 5, 1 to 4, 1 to 3, or 1 to 2.

Embodiment 52

The compound of any one of embodiments 40 to 51, wherein n is 3.

Embodiment 53

The compound of any one of embodiments 40 to 52, wherein at least one ligand is selected from a carbohydrate, cholesterol, a lipid, a phospholipid, an antibody, a lipoprotein, a hormone, a peptide, a vitamin, a steroid, and a cationic lipid.

Embodiment 54

The compound of embodiment 53, wherein at least one ligand is a carbohydrate.

Embodiment 55

The compound of embodiment 54, wherein at least one ligand is selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-mannofuranose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, N-acetylgalactosamine.

Embodiment 56

The compound of embodiment 54 or embodiment 55, wherein at least one ligand is selected from N-acetylgalactosamine, galactose, galactosamine, N-formylgalactosamine, N-propionyl-galactosamine, N-n-butanoylgalactosamine, and N-iso-butanoyl-galactosamine.

Embodiment 57

The compound of embodiment 56, wherein each ligand is N-acetylgalactosamine.

Embodiment 58

The compound of any one of embodiments 40 to 57, wherein the compound has the structure:

(I)

wherein each N of $N_m$ is, independently, a modified or unmodified nucleoside and m is from 1 to 5; $X_1$ and $X_2$ are each, independently, a phosphodiester linkage or a phosphorothioate linkage; and MO is the modified oligonucleotide.

Embodiment 59

The compound of any one of the preceding embodiments, wherein oligo1 consists of 7 to 15 linked nucleosides, 7 to 14 linked nucleosides, 7 to 13 linked nucleosides, 7 to 12 linked nucleosides, 7 to 11 linked nucleosides, 7 to 10 linked nucleosides, 8 to 15 linked nucleosides, 8 to 14 linked nucleosides, 8 to 13 linked nucleosides, 8 to 12 linked nucleosides, 8 to 11 linked nucleosides, 8 to 10 linked nucleosides, or 10 linked nucleosides.

Embodiment 60

The compound of embodiment 59, wherein oligo1 comprises at least one nucleoside with a modified sugar moiety.

Embodiment 61

The compound of embodiment 59 or embodiment 60, wherein oligo1 comprises at least one nucleoside with an unmodified sugar moiety.

Embodiment 62

The compound of any one of embodiments 59 to 61, wherein oligo1 comprises a plurality of nucleosides with a modified sugar moiety, and a plurality of nucleosides with an unmodified sugar moiety.

Embodiment 63

The compound of any one of embodiments 59 to 62, wherein at least 4, at least 5, at least 6, at least 7, or at least 8 nucleosides of oligo1 have a modified sugar moiety.

Embodiment 64

The compound of embodiment 63, wherein each nucleoside of oligo1 has a modified sugar moiety.

Embodiment 65

The compound of any one of embodiments 60 to 64, wherein each modified nucleoside is independently selected from a 2'-O-methyl sugar moiety, a 2'-O-methoxyethyl sugar moiety, a 2'-fluoro sugar moiety, and a bicyclic sugar moiety.

Embodiment 66

The compound of embodiment 65, wherein each bicyclic sugar moiety is independently selected from a cEt sugar moiety and an LNA sugar moiety.

Embodiment 67

The compound of any one of embodiments 60 to 66, wherein each unmodified sugar moiety is independently selected from a β-D-deoxyribose and a β-D-ribose.

Embodiment 68

The compound of any one of the preceding embodiments, wherein oligo2 consists of 7 to 15 linked nucleosides, 7 to 14 linked nucleosides, 7 to 13 linked nucleosides, 7 to 12 linked nucleosides, 7 to 11 linked nucleosides, 7 to 10 linked nucleosides, 8 to 15 linked nucleosides, 8 to 14 linked nucleosides, 8 to 13 linked nucleosides, 8 to 12 linked nucleosides, 8 to 11 linked nucleosides, 8 to 10 linked nucleosides, or 10 linked nucleosides.

Embodiment 69

The compound of embodiment 68, wherein oligo2 comprises at least one nucleoside with a modified sugar moiety.

Embodiment 70

The compound of embodiment 68 or embodiment 69, wherein oligo2 comprises at least one nucleoside with an unmodified sugar moiety.

Embodiment 71

The compound of any one of embodiments 68 to 70, wherein oligo2 comprises a plurality of nucleosides with a modified sugar moiety, and a plurality of nucleosides with an unmodified sugar moiety.

Embodiment 72

The compound of any one of embodiments 68 to 71, wherein at least 4, at least 5, at least 6, at least 7, or at least 8 nucleosides of oligo2 have a modified sugar moiety.

Embodiment 73

The compound of embodiment 68, wherein each nucleoside of oligo2 has a modified sugar moiety.

Embodiment 74

The compound of any one of embodiments 68 to 73, wherein each modified nucleoside is independently selected from a 2'-O-methyl sugar moiety, a 2'-O-methoxyethyl sugar moiety, a 2'-fluoro sugar moiety, and a bicyclic sugar moiety.

Embodiment 75

The compound of embodiment 74, wherein each bicyclic sugar moiety is independently selected from a cEt sugar moiety and an LNA sugar moiety.

Embodiment 76

The compound of any one of embodiments 68 to 75, wherein each unmodified sugar moiety is independently selected from a β-D-deoxyribose and a β-D-ribose.

Embodiment 77

The compound of any one of embodiments 15 to 76, wherein oligo3 consists of 7 to 15 linked nucleosides, 7 to 14 linked nucleosides, 7 to 13 linked nucleosides, 7 to 12 linked nucleosides, 7 to 11 linked nucleosides, 7 to 10 linked nucleosides, 8 to 15 linked nucleosides, 8 to 14 linked nucleosides, 8 to 13 linked nucleosides, 8 to 12 linked nucleosides, 8 to 11 linked nucleosides, or 8 to 10 linked nucleosides, or 10 linked nucleosides.

Embodiment 78

The compound of embodiment 77, wherein oligo3 comprises at least one nucleoside with a modified sugar moiety.

Embodiment 79

The compound of embodiment 77 or embodiment 78, wherein oligo3 comprises at least one nucleoside with an unmodified sugar moiety.

Embodiment 80

The compound of any one of embodiments 77 to 79, wherein oligo3 comprises a plurality of nucleosides with a modified sugar moiety, and a plurality of nucleosides with an unmodified sugar moiety.

Embodiment 81

The compound of any one of embodiments 77 to 80, wherein at least 4, at least 5, at least 6, at least 7, or at least 8 nucleosides of oligo3 have a modified sugar moiety.

Embodiment 82

The compound of embodiment 81, wherein each nucleoside of oligo3 has a modified sugar moiety.

Embodiment 83

The compound of any one of embodiments 78 to 82, wherein each modified nucleoside is independently selected from a 2'-O-methyl sugar moiety, a 2'-O-methoxyethyl sugar moiety, a 2'-fluoro sugar moiety, and a bicyclic sugar moiety.

Embodiment 84

The compound of embodiment 83, wherein each bicyclic sugar moiety is independently selected from a cEt sugar moiety and an LNA sugar moiety.

Embodiment 85

The compound of any one of embodiments 77 to 84, wherein each unmodified sugar moiety is independently selected from a β-D-deoxyribose and a β-D-ribose.

Embodiment 86

The compound of any one of the preceding embodiments, wherein oligo1 has the nucleobase sequence 5'-CAAUGCUGCA-3' (SEQ ID NO: 6).

Embodiment 87

The compound of any one of the preceding embodiments, wherein oligo2 has the nucleobase sequence 5'-CAAUGCUGCA-3' (SEQ ID NO: 6).

Embodiment 88

The compound of any one of the preceding embodiments, wherein the compound comprises a modified oligonucleotide having nucleobase sequence 5'-CAAUGCUG-CAAACAAUGCUGCA-3' (SEQ ID NO: 7).

Embodiment 89

The compound of any one of the preceding embodiments, wherein oligo 1 is 5'-$C_SA_SA_SU_SG_SC_SU_SG_SC_SA_S$-3' (SEQ ID NO: 6), wherein each nucleoside followed by a subscript "S" is a S-cEt nucleoside.

Embodiment 90

The compound of any one of the preceding embodiments, wherein oligo 2 is 5'-$C_SA_SA_SU_SG_SC_SU_SG_SC_SA_S$-3' (SEQ ID NO: 6), wherein each nucleoside followed by a subscript "S" is a S-cEt nucleoside.

Embodiment 91

The compound of any one of the preceding embodiments, wherein the modified oligonucleotide consists of 5'-$C_SA_S$ $A_SU_SG_SC_SU_SG_SC_SA_SA AC_SA_SA_SU_SG_SC_SU_SG_SC_SA_S$-3' (SEQ ID NO: 7), wherein each nucleoside followed by a subscript "S" is a S-cEt nucleoside and each nucleoside not followed by a subscript is a deoxynucleoside.

Embodiment 92

The compound of any one of embodiments 89 to 91, wherein each internucleoside linkage linking two S-cEt nucleosides is a phosphorothioate linkage.

Embodiment 93

The compound of embodiment 91 or embodiment 92, wherein at least one internucleoside linkage linking a deoxynucleoside nucleoside to another nucleoside is a phosphodiester linkage.

Embodiment 94

The compound of embodiment 93, wherein each internucleoside linkage linking a deoxynucleoside nucleoside to another nucleoside is a phosphodiester linkage.

Embodiment 95

A compound comprising the structure:

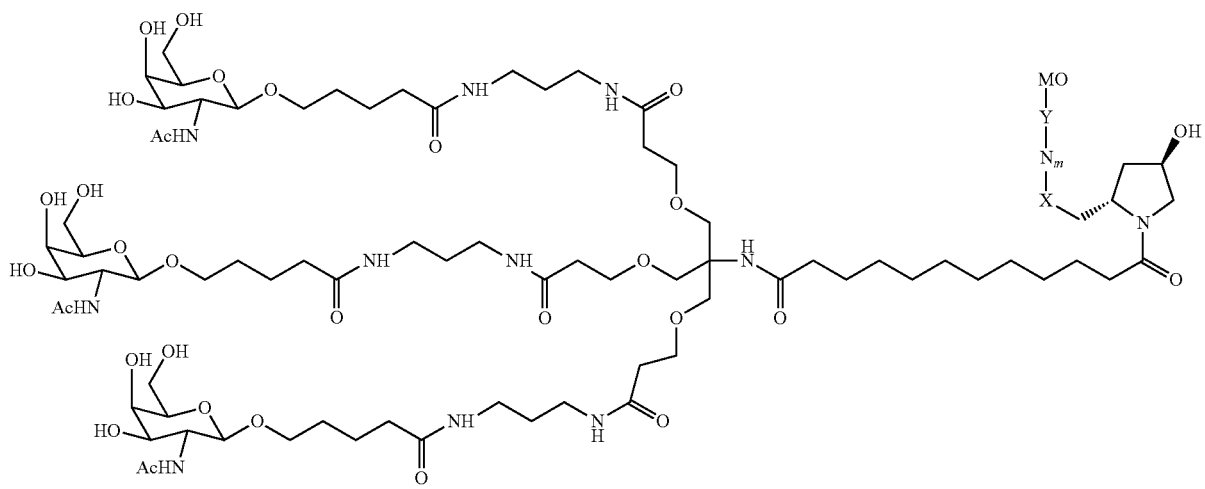

(II)

wherein X is a phosphodiester linkage; each N of $N_m$ is a deoxyadenosine (A); m is 2; Y is a phosphodiester linkage; and MO is 5'-$C_SA_SA_SU_SG_SC_SU_SG_SC_SA_SAAC_SA_S A_SU_SG_SC_SU_SG_SC_SA_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages.

Embodiment 96

A method for reducing a blood glucose level of a subject comprising administering to the subject a compound of any one of embodiments 1 to 95, 148, 156-163, 178, and 184.

Embodiment 97

The method of embodiment 96, wherein the subject has an elevated blood glucose level.

Embodiment 98

The method of embodiment 96 or embodiment 97, comprising measuring the blood glucose level of the subject.

Embodiment 99

The method of any one of embodiments 96 to 98, wherein the subject has an elevated blood glucose level.

Embodiment 100

The method of any one of embodiments 96 to 99, wherein the blood glucose level is a fasted blood glucose level, a post-prandial blood glucose level, a whole blood glucose level, or a plasma blood glucose level.

Embodiment 101

The method of any one of embodiments 96 to 100, comprising reducing the blood glucose level to below 200 mg/dL, below 175 mg/dL, below 150 mg/dL, below 125 mg/dL, below 120 mg/dL, below 115 mg/dL, below 110 mg/dL, below 105 mg/dL, or below 100 mg/dL.

Embodiment 101.2

The method of any one of embodiments 96 to 101, comprising reducing the hemoglobin A1c (HbA1c) level of a subject to below 8%, to below 7.5%, to below 7%, to below 6.5%, to below 6%, to below 5.5%, to below 5%, or to below 4.5%.

Embodiment 102

A method for preventing or delaying the onset of an elevated blood glucose level in a subject at risk for developing an elevated glucose level comprising administering to the subject a compound of any one of embodiments 1 to 95, 148, 156-163, 178, and 184.

Embodiment 103

A method for improving insulin sensitivity in a subject comprising administering to the subject a compound of any one of embodiments 1 to 95, 148, 156-163, and 178.

Embodiment 104

The method of embodiment 103, wherein the subject has insulin resistance.

Embodiment 105

A method for preventing or delaying the onset of insulin resistance in a subject at risk for developing insulin resistance comprising administering to the subject a compound of any one of embodiments 1 to 95, 148, 156-163, 178, and 184.

Embodiment 106

A method for improving glucose tolerance in a subject comprising administering to the subject a compound of any one of embodiments 1 to 95, 148, 156-163, 178, and 184.

Embodiment 107

The method of embodiment 106, wherein the subject has impaired glucose tolerance.

Embodiment 108

A method of treating at least one metabolic disorder in a subject, comprising administering to the subject having a metabolic disorder a compound of any one of embodiments 1 to 95, 148, 156-163, 178, and 184.

Embodiment 109

A method of preventing or delaying the onset of at least one metabolic disorder in a subject, comprising administering to the subject having a metabolic disorder a compound of any one of embodiments 1 to 95, 148, 156-163, 178, and 184.

Embodiment 110

The method of embodiment 108 or embodiment 109, wherein at least one metabolic disorder is selected from among pre-diabetes, diabetes, metabolic syndrome, obesity, diabetic dyslipidemia, hyperlipdemia, hypertension, hypertriglyceridemia, hyperfattyacidemia, hypercholesterolemia, and hyperinsulinemia.

Embodiment 111

A method of increasing adipocyte differentiation in a subject comprising administering to the subject a compound of any one of embodiments 1 to 95, 148, 156-163, 178, and 184.

Embodiment 112

A method of increasing the number of small adipocytes in a subject comprising administering to the subject a compound of any one of embodiments 1 to 95, 148, 156-163, 178, and 184.

Embodiment 113

The method of any one of embodiments 96 to 112, comprising reducing body weight of the subject.

Embodiment 114

The method of any of any one of embodiments 96 to 113, comprising reducing body fat in the subject.

Embodiment 115

The method of any of any one of embodiments 96 to 114, wherein the administering comprises parenteral administration, such as intravenous administration or subcutaneous administration; or oral administration.

Embodiment 116

The method of any of any one of embodiments 96 to 115, comprising administering at least one additional therapy.

Embodiment 117

The method of embodiment 116, wherein the at least one additional therapy is a glucose-lowering agent or a lipid lowering agent.

Embodiment 118

The method of embodiment 117, wherein the glucose-lowering agent is selected from among a PPAR agonist (gamma, dual, or pan), a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, a meglitinide, a thiazolidinedione, and sulfonylurea.

Embodiment 119

The method of any one of embodiments 116 to 118, wherein the at least one additional therapy is administered at the same time as administration of the compound, prior to administration of the compound, or after administration of the compound.

Embodiment 120

The method of any one of embodiments 116 to 118, wherein the at least one additional therapy is administered less frequently than the compound or more frequently than the compound.

Embodiment 121

The method of any one of embodiments 96 to 120, wherein the compound is administered as a pharmaceutical composition.

Embodiment 122

A method of improving insulin resistance in a cell or tissue comprising contacting the cell or tissue with a compound of any one of embodiments 1 to 95, 148, 156-163, 178, and 184.

Embodiment 123

The method of embodiment 122, wherein the cell or tissue is a liver, fat, or skeletal muscle cell or tissue.

Embodiment 124

A method of increasing insulin sensitivity in a cell or tissue comprising contacting the cell or tissue with a compound of any one of embodiments 1 to 95, 148, 156-163, 178, and 184.

Embodiment 125

The method of embodiment 124, wherein the cell is an adipocyte cell.

Embodiment 126

A method of inducing adipocyte differentiation comprising contacting an undifferentiated adipocyte with a compound of any one of embodiments 1 to 95, 148, 156-163, 178, and 184.

Embodiment 127

A pharmaceutical composition comprising a compound of any one of embodiments 1 to 95, 148, and 156-163 and a pharmaceutically acceptable carrier.

Embodiment 128

The method of any one of embodiments 96 to 107, wherein the subject has at least one metabolic disorder.

Embodiment 129

The method of embodiment 128, wherein the wherein at least one metabolic disorder is selected from among pre-diabetes, diabetes, metabolic syndrome, obesity, diabetic dyslipidemia, hyperlipdemia, hypertension, hypertriglyceridemia, hyperfattyacidemia, hypercholesterolemia, and hyperinsulinemia.

Embodiment 130

Use of a compound of any one of embodiments 1 to 95, 148, 156-163, 178, and 184 for use in therapy.

Embodiment 131

The use of embodiment 130, wherein the therapy is reduction of a blood glucose level in a subject, or prevention of an elevated blood glucose level in a subject.

Embodiment 132

The use of embodiment 130, wherein the therapy is treatment of a metabolic disorder.

Embodiment 133

The use of embodiment 132, wherein the metabolic disorder is selected from among pre-diabetes, diabetes, metabolic syndrome, obesity, diabetic dyslipidemia, hyperlipdemia, hypertension, hypertriglyceridemia, hyperfattyacidemia, hypercholesterolemia, and hyperinsulinemia.

Embodiment 134

The method of embodiment 124, wherein the cell is a liver cell or the tissue is a liver tissue.

Embodiment 135

A method of treating fatty liver disease comprising administering to a subject a compound of any one of embodiments 1 to 95, 148, 156-163, 178, and 184.

Embodiment 136

The method of embodiment 135, wherein the fatty liver disease is selected from non-alcoholic fatty liver disease (NAFLD), alcoholic fatty liver disease, alcoholic steatohepatitis, and non-alcoholic steatohepatitis (NASH).

Embodiment 137

The use of any one of embodiments 130 to 133, wherein the therapy is treatment of fatty liver disease in a subject.

Embodiment 138

The use of embodiment 137, wherein the fatty liver disease is selected from non-alcoholic fatty liver disease (NAFLD), alcoholic fatty liver disease, alcoholic steatohepatitis, and non-alcoholic steatohepatitis (NASH).

Embodiment 139

A method of reducing liver triglycerides comprising administering to a subject a compound of any one of embodiments 1 to 95, 148, 156-163, and 179.

Embodiment 140

The method of any one of embodiments 96 to 126, 128, 129, 134, and 139, wherein the subject has fatty liver disease.

Embodiment 141

The method of embodiment 140, wherein the fatty liver disease is selected from non-alcoholic fatty liver disease (NAFLD), alcoholic fatty liver disease, alcoholic steatohepatitis, and non-alcoholic steatohepatitis (NASH).

Embodiment 142

The use of embodiment 130, wherein the therapy comprises reducing liver triglycerides in a subject.

Embodiment 143

The use of embodiment 142, wherein the subject has fatty liver disease.

Embodiment 144

The use of embodiment 143, wherein the fatty liver disease is selected from non-alcoholic fatty liver disease (NAFLD), alcoholic fatty liver disease, alcoholic steatohepatitis, and non-alcoholic steatohepatitis (NASH).

Embodiment 145

A method of treating a metabolic disorder comprising administering to a subject a compound comprising a modified oligonucleotide consisting of a single region of 8 to 25 linked nucleosides, wherein the nucleobase sequence of the single region is complementary to miR-103 and/or miR-107, and wherein the compound comprises a conjugate moiety linked to the 5' terminus or the 3' terminus of the modified oligonucleotide, and wherein the conjugate moiety comprises a ligand that improves cellular uptake in a liver cell.

Embodiment 146

The method of embodiment 145, wherein the conjugate moiety comprises a ligand having affinity for the asialoglycoprotein receptor.

Embodiment 147

The method of embodiment 145 or 146, wherein the ligand is selected from N-acetylgalactosamine, galactose, galactosamine, N-formylgalactosamine, N-propionyl-galactosamine, N-n-butanoylgalactosamine, and N-iso-butanoylgalactosamine.

Embodiment 148

The compound of embodiment 95, wherein Y is linked to the 3' terminus of MO.

Embodiment 149

A method of treating a metabolic disorder comprising administering to a subject a compound comprising a modified oligonucleotide consisting of a single region of 8 to 25 linked nucleosides, wherein the nucleobase sequence of the single region is complementary to miR-103 and/or miR-107 with a mismatch to the 5' terminal A of miR-103 or miR-107.

Embodiment 150

The method of embodiment 149, wherein the 3' terminal nucleotide of the modified oligonucleotide is the mismatched position.

Embodiment 151

The method of embodiment 149 or embodiment 150, wherein the 3' terminal nucleotide of the modified oligonucleotide is selected from A, C, and G.

Embodiment 152

The method of any one of embodiments 149 to 151, wherein the compound comprises a conjugate moiety linked to the 5' terminus or the 3' terminus of the modified oligonucleotide, and wherein the conjugate moiety comprises a ligand that improves cellular uptake in a liver cell.

Embodiment 153

The method of embodiment 152, wherein the conjugate moiety comprises a ligand having affinity for the asialoglycoprotein receptor.

Embodiment 154

The method of embodiment 152 or 153, wherein the ligand is selected from N-acetylgalactosamine, galactose, galactosamine, N-formylgalactosamine, N-propionyl-galactosamine, N-n-butanoylgalactosamine, and N-iso-butanoylgalactosamine.

Embodiment 155

The method of any one of embodiments 152 to 153, wherein the modified oligonucleotide is fully complementary to miR-103 or miR-107 except for the mismatch to the 5' terminal A of miR-103 or miR-107.

Embodiment 156

A compound comprising a modified oligonucleotide consisting of a single region of 8 to 25 linked nucleosides, wherein the nucleobase sequence of the single region is complementary to miR-103 and/or miR-107 with a mismatch to the 5' terminal A of miR-103 and miR-107.

Embodiment 157

The compound of embodiment 156, wherein the 3' terminal nucleotide of the modified oligonucleotide is the mismatched position.

Embodiment 158

The compound of embodiment 156 or embodiment 157, wherein the 3' terminal nucleotide of the modified oligonucleotide is selected from A, C, and G.

Embodiment 159

The compound of any one of embodiments 156 to 158, wherein the compound comprises a conjugate moiety linked to the 5' terminus or the 3' terminus of the modified oligonucleotide, and wherein the conjugate moiety comprises a ligand that improves cellular uptake in a liver cell.

Embodiment 160

The compound of embodiment 159, wherein the conjugate moiety comprises a ligand having affinity for the asialoglycoprotein receptor.

Embodiment 161

The compound of embodiment 159 or 160, wherein the ligand is selected from N-acetylgalactosamine, galactose, galactosamine, N-formylgalactosamine, N-propionyl-galactosamine, N-n-butanoylgalactosamine, and N-iso-butanoylgalactosamine.

Embodiment 162

The compound of any one of embodiments 156 to 161, wherein the modified oligonucleotide is fully complementary to miR-103 or miR-107 except for the mismatch to the 5' terminal A of miR-103 or miR-107.

Embodiment 163
A compound having the structure:
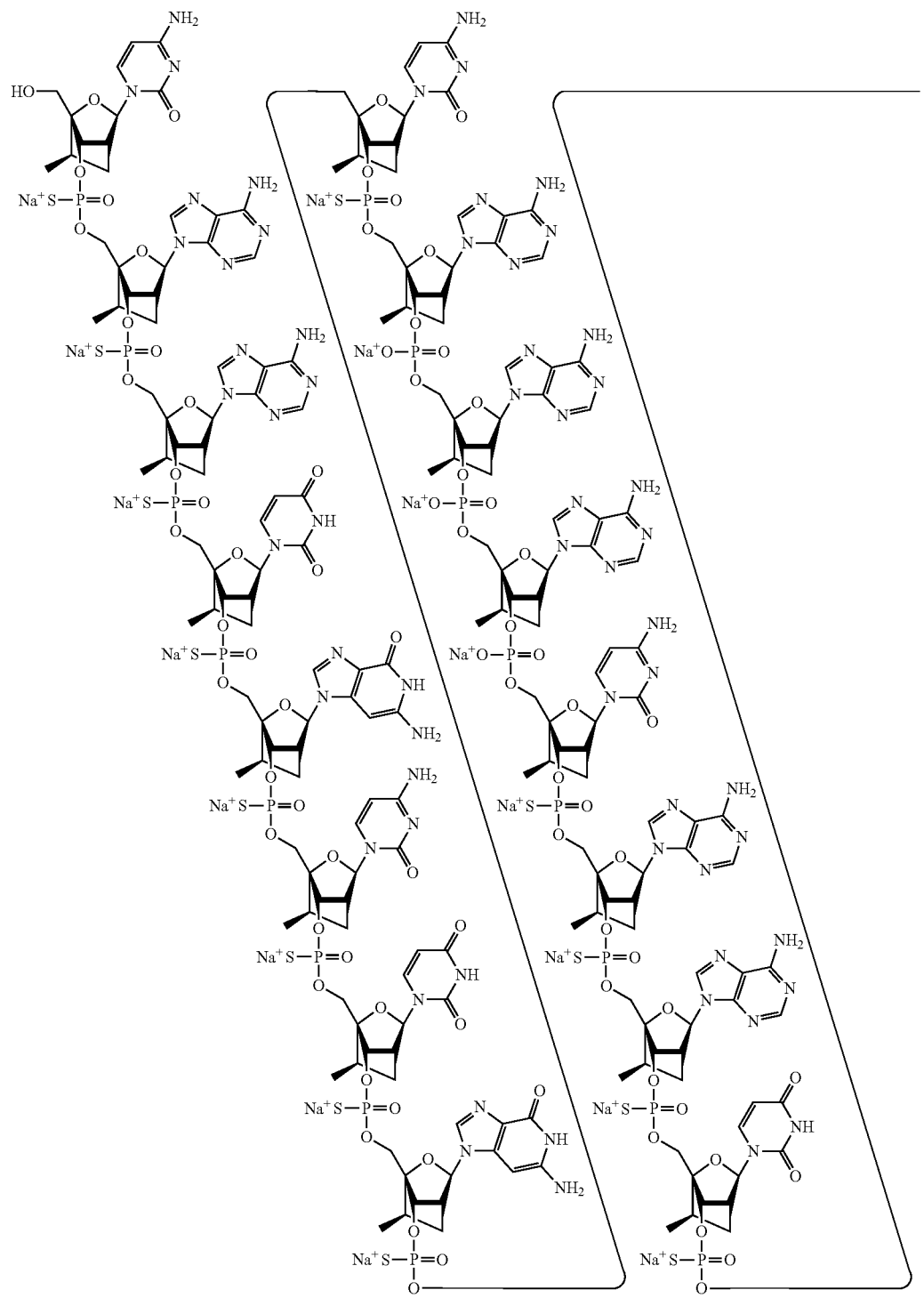

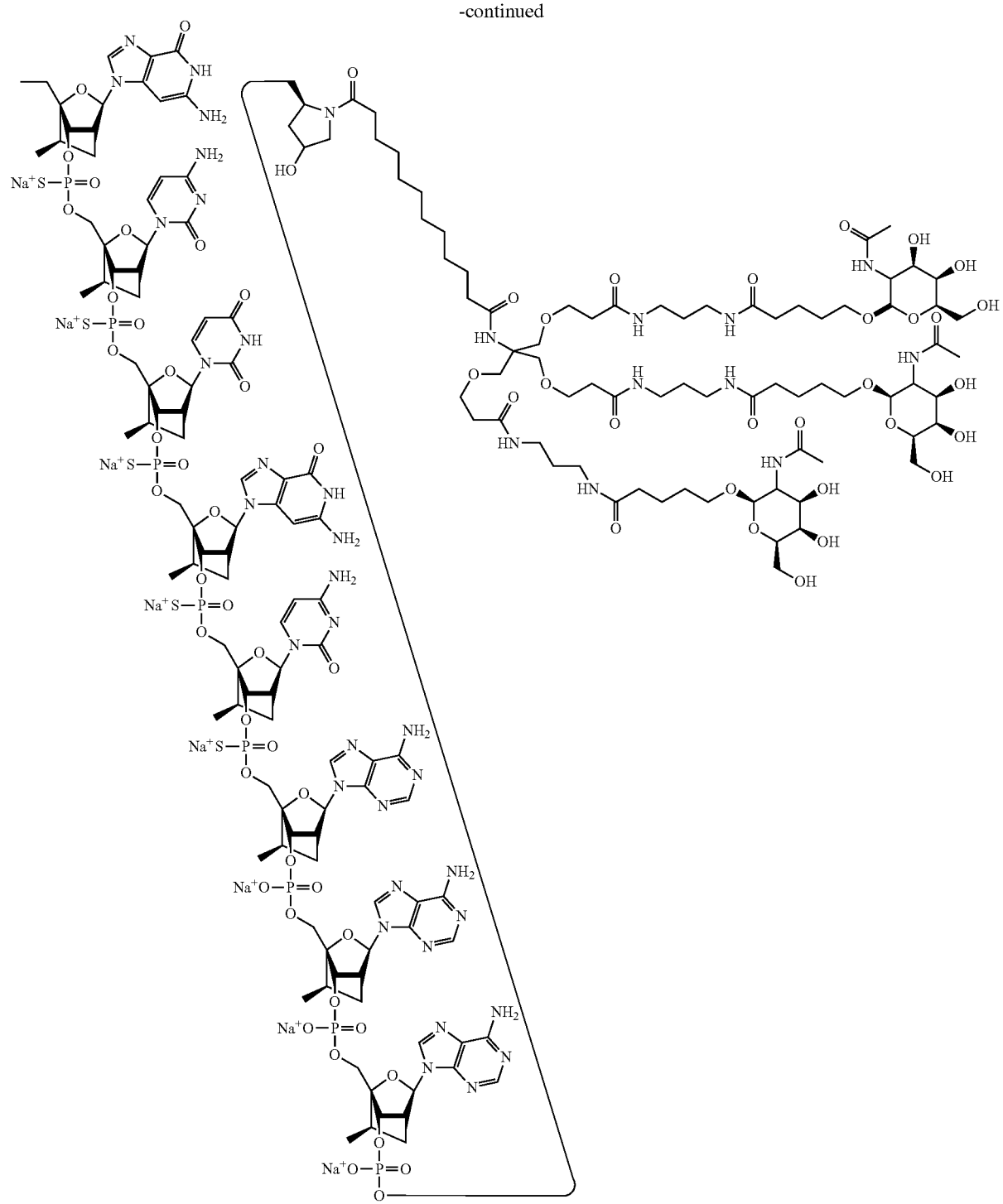

Embodiment 164

A pharmaceutical composition comprising the compound of embodiment 163 and a pharmaceutically acceptable carrier.

Embodiment 165

The pharmaceutical composition of embodiment 164, which comprises 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg of the compound of claim 163.

Embodiment 166

The pharmaceutical composition of embodiment 164 or embodiment 165, which is an aqueous composition.

Embodiment 167

The pharmaceutical composition of embodiment 164 or embodiment 165, which is a lyophilized composition.

Embodiment 168

The method of any one of embodiments 135, 136, 139 to 141, and 145-155, wherein the subject has a metabolic disorder selected from among pre-diabetes, diabetes, metabolic syndrome, obesity, diabetic dyslipidemia, hyperlipdemia, hypertension, hypertriglyceridemia, hyperfattyacidemia, hypercholesterolemia, and hyperinsulinemia.

Embodiment 169

The method of any one of embodiments 135, 136, 139, 140, 141, and 145-155, wherein the subject has a metabolic disorder selected from pre-diabetes and type 2 diabetes.

Embodiment 170

The method of embodiment 135 or embodiment 140, wherein the fatty liver disease is selected from non-alcoholic fatty liver disease (NAFLD) and non-alcoholic steatohepatitis (NASH).

Embodiment 171

The method of embodiment 170, wherein the subject has a metabolic disorder selected from pre-diabetes and type 2 diabetes.

Embodiment 172

The method of embodiment 170, wherein the subject has insulin resistance, elevated blood glucose levels, or elevated HbA1c levels.

Embodiment 173

The use of embodiment 130, wherein the therapy is for treatment of fatty liver disease in a subject with at least one metabolic disorder selected from pre-diabetes, diabetes, metabolic syndrome, obesity, diabetic dyslipidemia, hyperlipdemia, hypertension, hypertriglyceridemia, hyperfattyacidemia, hypercholesterolemia, and hyperinsulinemia.

Embodiment 174

The use of embodiment 130, wherein the therapy is for treatment of fatty liver disease in a subject with a metabolic disorder selected from pre-diabetes and type 2 diabetes.

Embodiment 175

The use of embodiment 130, wherein the therapy is for treatment of fatty liver disease in a subject with insulin resistance, elevated blood glucose levels or elevated HbA1c levels.

Embodiment 176

The use of any of embodiments 173, 174 and 175, wherein the fatty liver disease is selected from non-alcoholic fatty liver disease (NAFLD), alcoholic fatty liver disease, alcoholic steatohepatitis, and non-alcoholic steatohepatitis (NASH).

Embodiment 177

The use of any one of embodiments 137, 143, 173, 174, and 175, wherein the fatty liver disease is selected from non-alcoholic fatty liver disease (NAFLD) and non-alcoholic steatohepatitis (NASH).

Embodiment 178

The method of any one of embodiments 96-121, 128, 129, 135, 139-141, and 168-172, wherein the compound is administered at a dose of 50 to 150 mg, at a frequency of once per week.

Embodiment 179

The compound of Embodiment 95, wherein the compound consists of the structure:

(II)

wherein X is a phosphodiester linkage; each N of $N_m$ is a deoxyadenosine (A); m is 2; Y is a phosphodiester linkage; Y is linked to the 3'-terminus of MO; MO is 5'-$C_SA_S$ $A_SU_SG_SC_SU_SG_SC_SA_SAAC_SA_SA_SU_SG_SC_SU_SG_SC_SA_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages; or a pharmaceutically acceptable salt thereof.

Embodiment 180

A pharmaceutical composition comprising the compound of Embodiment 179 and a pharmaceutically acceptable carrier.

Embodiment 181

A compound for treating a metabolic disorder in a subject, comprising a modified oligonucleotide consisting of 8 to 25 linked nucleosides, wherein the nucleobase sequence of the modified oligonucleotide is complementary to miR-103 and/or miR-107, and wherein the compound comprises a conjugate moiety linked to the 5' terminus or the 3' terminus of the modified oligonucleotide, and wherein the conjugate moiety comprises a ligand that improves cellular uptake in a liver cell.

Embodiment 182

The compound of embodiment 150, wherein the conjugate moiety comprises a ligand having affinity for the asialoglycoprotein receptor.

Embodiment 183

The compound of embodiment 150 or 151, wherein the ligand is selected from N-acetylgalactosamine, galactose, galactosamine, N-formylgalactosamine, N-propionyl-galactosamine, N-n-butanoylgalactosamine, and N-iso-butanoyl-galactosamine.

Embodiment 184

The compound of embodiment 156, wherein the compound consists of the structure:

wherein X is a phosphodiester linkage; each N of $N_m$ is a deoxyadenosine (A); m is 2; Y is a phosphodiester linkage; Y is linked to the 3' terminus of MO; and MO is 5'-$C_SA_S$ $A_SU_SG_SC_SU_SG_SC_SA_S$-3' (SEQ ID NO: 6), wherein each nucleoside followed by a subscript "S" is a S-cEt nucleoside, and each internucleoside linkage between two S-cEt nucleosides is a phosphorothioate linkage; or a pharmaceutically acceptable salt thereof.

Embodiment 185

A pharmaceutical composition comprising the compound of embodiment 184 and a pharmaceutically acceptable carrier.

(II)

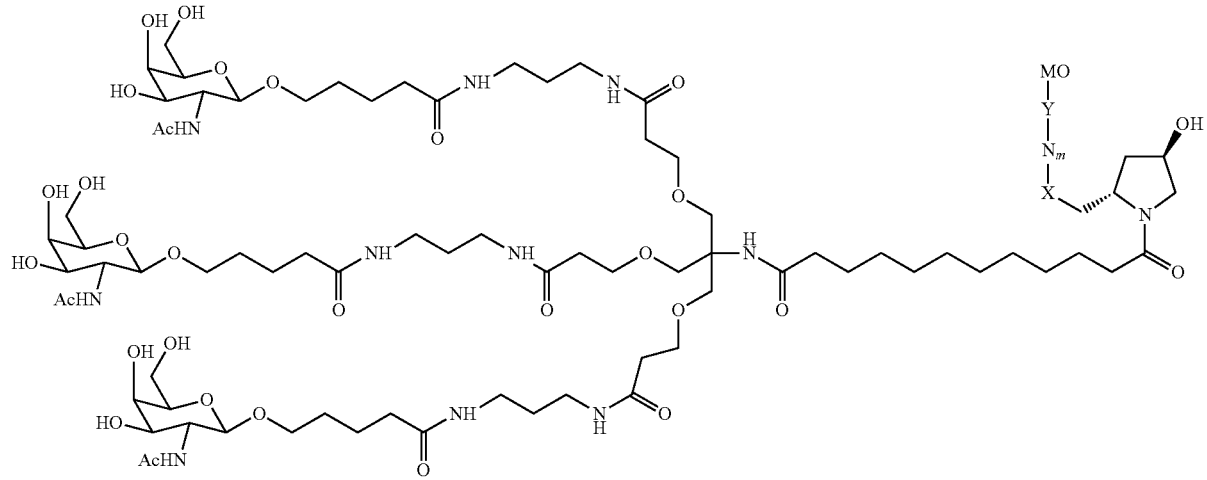

FIG. 12A-E shows a hyperinsulinemic euglycemic clamp study in DIO mice administered the indicated compound, as described in the Examples.

Figure 13:
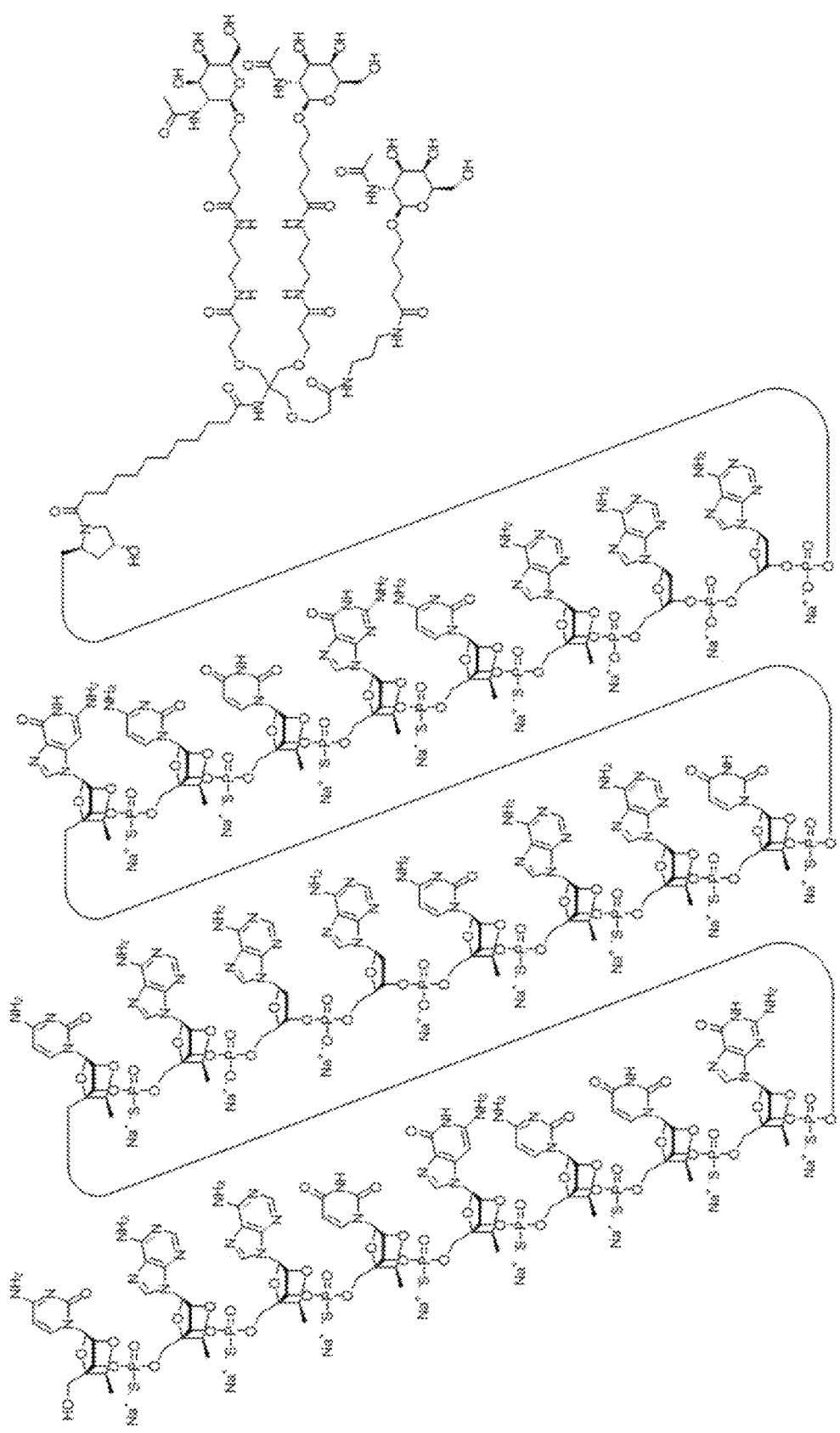

FIG. 13 shows the structure of compound 47043.

DETAILED DESCRIPTION

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Blood glucose level" means the concentration of glucose in the blood of a subject. In certain embodiments, blood glucose levels are expressed as milligrams of glucose per deciliter of blood. In certain embodiments, blood glucose levels are expressed as mmol of glucose per liter of blood.

"Elevated blood glucose level" means a blood glucose level that is higher than normal.

"Fasted blood glucose level" means a blood glucose level after a subject has fasted for a certain length of time. For example, a subject may fast for at least 8 hours prior to measurement of a fasted blood glucose level.

"Post-prandial blood glucose level" means a blood glucose level after a subject has eaten a meal. In certain embodiments, a post-prandial blood glucose level is measured two hours after a subject has eaten a meal.

"Whole blood glucose level" means the concentration of glucose in whole blood which has not been subjected to separation.

"Plasma blood glucose level" means the concentration of glucose in plasma following separation of whole blood into plasma and red blood cell fractions.

"Insulin sensitivity" means the ability of cells to take up glucose in response to insulin action.

"Insulin resistance" means a condition in which normal amounts of insulin are inadequate to produce a normal insulin response from fat, muscle and liver cells. Insulin resistance in fat cells results in hydrolysis of stored triglycerides, which elevates free fatty acids in the blood. Insulin resistance in muscle reduces the uptake of glucose from the blood by muscle cells. Insulin resistance in liver reduces glucose storage and a failure to suppress glucose production. Elevated free fatty acids, reduced glucose uptake, and elevated glucose production all contribute to elevated blood glucose levels. High plasma levels of insulin and glucose due to insulin resistance often leads to metabolic syndrome and type 2 diabetes.

"Improving insulin resistance" means increasing the ability of cells to produce a normal insulin response. In certain embodiments, insulin resistance is improved in muscle cells, leading to an increased uptake of glucose in muscle cells. In certain embodiments, insulin resistance is improved in liver cells, leading to increased glucose storage in liver cells. In certain embodiments, insulin resistance is improved in fat cells, leading to reduced hydrolysis of triglycerides, and consequently reduced free fatty acid in the blood.

"Metabolic disorder" means a condition characterized by an alteration or disturbance in one or more metabolic processes in the body. Metabolic disorders include, but are not limited to, hyperglycemia, prediabetes, diabetes, type 1 diabetes, type 2 diabetes, obesity, diabetic dyslipidemia, metabolic syndrome, and hyperinsulinemia. "Diabetes" or "diabetes mellitus" means a disease in which the body does not produce or properly use insulin, resulting in abnormally high blood glucose levels. In certain embodiments, diabetes is type 1 diabetes. In certain embodiments, diabetes is type 2 diabetes.

"Prediabetes" means a condition in which a subject's blood glucose levels are higher than in a subject with normal blood glucose levels but lower but not high enough for a diagnosis of diabetes.

"Type 1 diabetes" means diabetes characterized by loss of the insulin-producing beta cells of the islets of Langerhans in the pancreas leading to a deficiency of insulin (also known as insulin-dependent diabetes mellitus or IDDM). Type I diabetes can affect children or adults, but typically appears between the ages of 10 and 16.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Diabetic dyslipidemia" or "Type 2 diabetes with dyslipidemia" means a condition characterized by Type 2 diabetes, reduced HDL-C, elevated serum triglycerides, and elevated small, dense LDL particles.

"Metabolic syndrome" means a condition characterized by a clustering of lipid and nonlipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Steatosis" means a condition characterized by the excessive accumulation of triglycerides in hepatocytes.

"Steatohepatitis" means steatosis with inflammation.

"Non-alcoholic fatty liver disease (NAFLD)" means a condition characterized by accumulation of fat in the liver in subjects who consume little to no alcohol. In certain embodiments, NAFLD is related to insulin resistance and the metabolic syndrome. "Nonalcoholic steatohepatitis (NASH)" means a condition characterized by accumulation of fat in the liver, combined with inflammation and scarring in the liver. In certain embodiments NASH results from a worsening progression of NAFLD.

"Alcoholic steatohepatitis (ASH)" means an alcohol-induced condition characterized by accumulation of fat in the liver, combined with inflammation and scarring in the liver.

"Glucose Tolerance Test" or "GTT" means a test performed to determine how quickly glucose is cleared from the blood. Typically, the test involves administration of glucose, followed by measurement of glucose levels in blood at intervals over a period of time. "IPGTT" means a GTT performed following intraperitoneal injection of glucose. "OGTT" means a GTT performed following oral administration of glucose. In certain embodiments, a GTT is used to test for pre-diabetes. In certain embodiments, a GTT is used to identify a subject with diabetes. In certain embodiments, a GTT is used to identify a subject at risk for developing diabetes. In certain embodiments a GTT is used to identify a subject having insulin resistance.

"Insulin Tolerance Test (ITT)" means a test performed to measure insulin sensitivity through hormone response to the stress of a low blood sugar level. In certain embodiments, a ITT is used to test for pre-diabetes. In certain embodiments, a ITT is used to identify a subject with diabetes. In certain embodiments, a ITT is used to identify a subject at risk for developing diabetes. In certain embodiments a ITT is used to identify a subject having insulin resistance.

"Metabolic rate" means the rate of metabolism or the amount of energy expended in a given period. "Basal metabolic rate" means the amount of energy expended while at rest in a neutrally temperate environment, in the post-absorptive state (meaning that the digestive system is inactive, which requires about twelve hours of fasting in humans); the release of energy in this state is sufficient only for the functioning of the vital organs, such as the heart, lungs, brain and the rest of the nervous system, liver, kidneys, sex organs, muscles and skin.

"Target nucleic acid" means a nucleic acid to which an oligonucleotide is designed to hybridize.

"Target RNA" means an RNA to which an oligonucleotide is complementary.

"Targeting" means the process of design and selection of nucleobase sequence that will hybridize to a target nucleic acid.

"Targeted to" means having a nucleobase sequence that will allow hybridization to a target nucleic acid.

"Target engagement" means the interaction of an oligonucleotide with the microRNA to which it is complementary, in a manner that changes the activity, expression or level of the microRNA. In certain embodiments, target engagement means an anti-miR interacting with the microRNA to which it is complementary, such that the activity of the microRNA is inhibited.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"5' target site" means the nucleobase of a target nucleic acid which is complementary to the 3'-most nucleobase of a particular oligonucleotide.

"3' target site" means the nucleobase of a target nucleic acid which is complementary to the 5'-most nucleobase of a particular oligonucleotide.

"Region" means a portion of linked nucleosides within a nucleic acid. In certain embodiments, an oligonucleotide has a nucleobase sequence that is complementary to a region of a target nucleic acid. For example, in certain embodiments an oligonucleotide is complementary to a region of a microRNA stem-loop sequence. In certain embodiments, an oligonucleotide is fully complementary to a region of a microRNA stem-loop sequence.

"Segment" means a smaller or sub-portion of a region.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microrna.sanger.ac.uk/). In certain embodiments, microRNA is abbreviated as "microRNA" or "miR."

"Pre-microRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature microRNA sequence. Pre-microRNA sequences and stem-loop sequences may overlap. Examples of stem-loop sequences are found in the microRNA database known as miRBase (http://microrna.sanger.ac.uk/).

"Pri-microRNA" or "pri-miR" means a non-coding RNA having a hairpin structure that is a substrate for the double-stranded RNA-specific ribonuclease Drosha.

"microRNA precursor" means a transcript that originates from a genomic DNA and that comprises a non-coding, structured RNA comprising one or more microRNA sequences. For example, in certain embodiments a microRNA precursor is a pre-microRNA. In certain embodiments, a microRNA precursor is a pri-microRNA.

"microRNA-regulated transcript" means a transcript that is regulated by a microRNA.

"Monocistronic transcript" means a microRNA precursor containing a single microRNA sequence.

"Polycistronic transcript" means a microRNA precursor containing two or more microRNA sequences.

"Seed sequence" means a nucleobase sequence comprising from 6 to 8 contiguous nucleobases of nucleobases 1 to 9 of the 5'-end of a mature microRNA sequence.

"Seed match sequence" means a nucleobase sequence that is complementary to a seed sequence, and is the same length as the seed sequence.

"Anti-miR" means an oligonucleotide having nucleobase sequence complementary to a microRNA. In certain embodiments, an anti-miR is a modified oligonucleotide.

"Anti-miR-103/107," means an oligonucleotide having a nucleobase sequence complementary to miR-103 and miR107. In certain embodiments, an anti-miR-103/107 is 90% complementary to miR-103 and miR-107. In some such embodiments, an anti-miR-103/107 oligonucleotide consists of 10 linked nucleosides wherein 9 linked nucleotides are fully complementary to miR-103 and miR-107, and one nucleoside is a mismatch. In some such embodiments, the mismatch is located at the 3' end of the anti-miR-103/107 oligonucleotide. In certain embodiments, an anti-miR-103/ 107 is at least 80%, at least 85%, at least 90%, or at least 95% complementary to miR-103 and miR-107. In certain embodiments, an anti-miR-103/107 is a modified oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Gapmer" means a modified oligonucleotide having an internal region of linked β-D-deoxyribonucleosides positioned between two external regions of linked nucleosides, where each nucleoside of each external region comprises a modified sugar moiety. The β-D-deoxyribonucleosides may or may not have a modified nucleobase.

"Gap" is an internal region of a gapmer that is positioned between the external regions.

"Wing" is an external region of a gapmer that is adjacent to a 5' or 3' end of the internal region of the gapmer.

"Symmetric gapmer" means each nucleoside of each external region comprises the same sugar modification.

"Asymmetric gapmer" means each nucleoside of one external region comprises a first sugar modification, and each nucleoside of the other external region comprises a second sugar modification.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybrizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary to a microRNA, i.e. each nucleobase of the oligonucleotide is complementary to a nucleobase at a corresponding position in the microRNA. In certain embodiments, an oligonucleotide wherein each nucleobase has complementarity to a nucleobase within a region of a microRNA stem-loop sequence is fully complementary to the microRNA stem-loop sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"miR-103" means the mature miRNA having the nucleobase sequence set forth in SEQ ID NO: 1 (AGCAGCAUU-GUACAGGGCUAUGA).

"miR-107" means the mature miRNA having the nucleobase sequence set forth in SEQ ID NO: 2 (AGCAGCAUU-GUACAGGGCUAUCA). "miR-103-1 stem-loop sequence" means the miR-103 precursor having the nucleobase sequence set forth in SEQ ID NO: 3 (UACUGCC-CUC GGCUUCUUUACAGUGCUGCCUUGUUG-CAUAUGGAUCAAGCAGCAUUGUACAGGGCUAUG AAGGCAUUG).

"miR-103-2" means the miR-103 precursor having the nucleobase sequence set forth in SEQ ID NO: 4 (UUGUGC-UUUCAGCUUCUUUACAGUGCUGCCUUGUAG-CAUUCAGGU CAAGCAGCAUUGUACAGGGC-UAUGAAAGAACCA).

"miR-107 stem loop sequence" means the miR-107 precursor having the nucleobase sequence set forth in SEQ ID NO: 5 (CUCUCUGCUUUCAGCUUCUUUACAGUGU UGCCUUGUGGCAUGGAGUUCAAGCAGCAUU-GUACAGGGCUAUCAAAGCACAGA).

"miR-103/miR-107" means a microRNA having the nucleobase sequence of SEQ ID NO: 1 or SEQ ID NO: 2.

"Oligomeric compound" means a compound that comprises a plurality of linked monomeric subunits. Oligomeric compounds included oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

A "region of a modified oligonucleotide" refers to a portion set forth as oligo1, oligo2, or oligo3 in the modified oligonucleotide structures shown herein (e.g., [oligo1]-[x-N]$_m$-x-[oligo2] or [oligo1]-[x-N]$_m$-x-[oligo2]-[x-N]$_m$-x-[oligo3]). A region of a modified oligonucleotide may be an anti-miR-103/107. In some embodiments, each region of a modified oligonucleotide is an anti-miR-103/107. Thus, in some embodiments, a modified oligonucleotide may have the structure [anti-miR-103/107]-[x-N]$_m$-x-[anti-miR-103/107].

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar, and unmodified nucleobase. A modified nucleoside may have a modified sugar and a modified nucleobase. A modified nucleoside may have a natural sugar and a modified nucleobase.

"2'-modified nucleoside" means a nucleoside comprising a sugar with any modification at the position equivalent to the 2' position of the furanosyl ring as the positions are numbered in 2-deoxyribose or ribose. It is to be understood that 2'-modified nucleosides include, without limitation, nucleosides comprising bicyclic sugar moieties.

"Modified internucleoside linkage" means any change from a naturally occurring internucleoside linkage.

"Phosphorothioate internucleoside linkage" means a linkage between nucleosides where one of the non-bridging atoms is a sulfur atom.

A "phosphorothioate linkage" means a linkage between two chemical moieties having the same structure as a phosphorothioate internucleoside linkage, e.g., —OP(O)(S)O—.

A "phosphodiester linkage" means a linkage between two chemical moieties having the same structure as a phosphodiester internucleoside linkage, e.g., —OP(O)$_2$O—.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Modified nucleobase" means any nucleobase that is not an unmodified nucleobase.

"Furanosyl" means a structure comprising a 5-membered ring consisting of four carbon atoms and one oxygen atom.

"Naturally occurring furanosyl" means a ribofuranosyl as found in naturally occurring RNA or a deoxyribofuranosyl as found in naturally occurring DNA.

"Sugar moiety" means a naturally occurring furanosyl or a modified sugar moiety.

"Modified sugar moiety" means a substituted sugar moiety or a sugar surrogate.

"Substituted sugar moiety" means a furanosyl that is not a naturally occurring furanosyl. Substituted sugar moieties include, but are not limited to sugar moieties comprising modifications at the 2'-position, the 5'-position and/or the 4'-position of a naturally occurring furanosyl. Certain substituted sugar moieties are bicyclic sugar moieties.

"Sugar surrogate" means a structure that does not comprise a furanosyl and that is capable of replacing the naturally occurring furanosyl of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

"β-D-deoxyribose" means a naturally occurring DNA sugar moiety.

"β-D-ribose" means a naturally occurring RNA sugar moiety.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a (CH$_2$)—O bridge between the 4' and 2' furanose ring atoms.

"ENA sugar moiety" means a substituted sugar moiety comprising a (CH$_2$)$_2$—O bridge between the 4' and 2' furanose ring atoms.

"Constrained ethyl (cEt) sugar moiety" means a substituted sugar moiety comprising a CH(CH$_3$)—O bridge between the 4' and the 2' furanose ring atoms. In certain embodiments, the CH(CH$_3$)—O bridge is constrained in the S orientation. In certain embodiments, the CH(CH$_3$)—O bridge is constrained in the R orientation.

"S-cEt sugar moiety" means a substituted sugar moiety comprising an S-constrained CH(CH$_3$)—O bridge between the 4' and the 2' furanose ring atoms.

"R-cEt sugar moiety" means a substituted sugar moiety comprising an R-constrained CH(CH$_3$)—O bridge between the 4' and the 2' furanose ring atoms.

"2'-O-methyl nucleoside" means a modified nucleoside having a 2'-O-methyl sugar modification.

"2'-O-methoxyethyl nucleoside" means a modified nucleoside having a 2'-O-methoxyethyl sugar modification. A 2'-O-methoxyethyl nucleoside may comprise a modified or unmodified nucleobase.

"2'-fluoro nucleoside" means a modified nucleoside having a 2'-fluoro sugar modification. A 2'-fluoro nucleoside may comprise a modified or unmodified nucleobase.

"Bicyclic nucleoside" means a modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"Non-bicyclic nucleoside" means a nucleoside that has a sugar other than a bicyclic sugar. In certain embodiments, a non-bicyclic nucleoside comprises a naturally occurring sugar. In certain embodiments, a non-bicyclic nucleoside comprises a modified sugar. In certain embodiments, a non-bicyclic nucleoside is a β-D-deoxyribonucleoside. In certain embodiments, a non-bicyclic nucleoside is a 2'-O-methoxyethyl nucleoside.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

"Motif" means a pattern of modified and/or unmodified nucleobases, sugars, and/or internucleoside linkages in an oligonucleotide. In certain embodiments, a motif is a nucleoside pattern.

"Nucleoside pattern" means a pattern of nucleoside modifications in an oligonucleotide or a region thereof. A nucleoside pattern is a motif that describes the arrangement of nucleoside modifications in an oligonucleotide.

"Stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

"Stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

"Stabilizing internucleoside linkage" means an internucleoside linkage that provides improved nuclease stability to an oligonucleotide relative to that provided by a phosphodiester internucleoside linkage. In one embodiment, a stabilizing internucleoside linkage is a phosphorothioate internucleoside linkage.

A "linking group" as used herein refers to an atom or group of atoms that attach a first chemical entity to a second chemical entity via one or more covalent bonds.

A "linker" as used herein, refers to an atom or group of atoms that attach one or more ligands to a modified or unmodified nucleoside via one or more covalent bonds. The modified or unmodified nucleoside may be part of a modified oligonucleotide as described herein, or may be attached to a modified oligonucleotide through a phosphodiester or phosphorothioate bond. In some embodiments, the linker attaches one or more ligands to the 3' end of a modified oligonucleotide. In some embodiments, the linker attaches one or more ligands to the 5' end of a modified oligonucleotide. In some embodiments, the linker attaches one or more ligands to a modified or unmodified nucleoside that is attached to the 3' end of a modified oligonucleotide. In some embodiments, the linker attaches one or more ligands to a modified or unmodified nucleoside that is attached to the 5' end of a modified oligonucleotide. When the linker attaches one or more ligands to the 3' end of a modified oligonucleotide or to a modified or unmodified nucleoside attached to the 3' end of a modified oligonucleotide, in some embodiments, the attachment point for the linker may be the 3' carbon of a modified or unmodified sugar moiety. When the linker attaches one or more ligands to the 5' end of a modified oligonucleotide or to a modified or unmodified nucleoside attached to the 5' end of a modified oligonucleotide, in some embodiments, the attachment point for the linker may be the 5' carbon of a modified or unmodified sugar moiety.

"Subject" means a human or non-human animal selected for treatment or therapy.

"Subject in need thereof" means the state in which a subject is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intracardial administration" means administration into the heart. In certain embodiments, intracardial administration occurs by way of a catheter. In certain embodiments, intracardial administration occurs by way of open heart surgery.

"Pulmonary administration" means administration to the lungs.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Pharmaceutically acceptable salt" means a physiologically and pharmaceutically acceptable salt of a compound provided herein, i.e., a salt that retains the desired biological activity of the compound and does not have undesired toxicological effects when administered to a subject. Non-limiting exemplary pharmaceutically acceptable salts of compounds provided herein include sodium and potassium salt forms. The term "compound" as used herein includes pharmaceutically acceptable salts thereof unless specifically indicated otherwise.

"Improved liver function" means the change in liver function toward normal limits. In certain embodiments, liver function is assessed by measuring molecules found in a subject's blood. For example, in certain embodiments, improved liver function is measured by a reduction in blood liver transaminase levels.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

Overview

Metabolic disorders are characterized by one or more abnormalities in metabolic function in the body. Certain metabolic disorders are related to defects in how the body uses blood glucose, resulting in abnormally high levels of blood glucose. Metabolic disorders may also be characterized by a deficiency in insulin production, or a deficiency in sensitivity to insulin. Metabolic disorders affect millions of people worldwide, and can be life-threatening disorders. As such, there is a need for method and compositions to treat, prevent, or delay the onset of metabolic disorders.

The administration of oligonucleotides complementary to miR-103 and/or miR-107 resulted in improved blood glucose levels, decreased gluconeogenesis, enhanced insulin sensitivity, and decreased plasma cholesterol. See, e.g., PCT Publication No. 2010/133970 A1. These effects were observed in animal models of diabetes/insulin resistance. Also observed was a decrease in body weight, which was due to a decrease in body fat. As miR-103 and miR-107 differ by one nucleobase, an oligonucleotide having a sequence complementary to the nucleobase sequence of miR-103 may hybridize to and inhibit the activity of both miR-103 and miR-107. Likewise, an oligonucleotide having a sequence complementary to the nucleobase sequence of miR-107 may hybridize to and inhibit the activity of both miR-103 and miR-107. As such, oligonucleotides complementary to either one or both of miR-103 and miR-107 may be used to achieve the phenotypic outcomes described herein.

Administration of a compound comprising an oligonucleotide complementary to miR-103, miR-107 or a precursor thereof may result in one or more clinically desirable outcomes. Such clinically desirable outcomes include but are not limited to reduced blood glucose levels, reduced hemoglobin A1c (HbA1c) levels, improved glucose tolerance, improved insulin resistance, and reduced gluconeogenesis.

Accordingly, provided herein are methods and compositions to reduce blood glucose levels, decrease gluconeogenesis, improve insulin sensitivity, and decrease plasma cholesterol. Also provided herein are methods to treat, prevent, or delay the onset of metabolic disorders that are related to elevated blood glucose levels, increased gluconeogenesis, impaired insulin sensitivity, and increased plasma cholesterol. In certain embodiments, metabolic disorders include, but are not limited to, prediabetes, diabetes, including Type 1 or Type 2 diabetes, metabolic syndrome, obesity, diabetic dyslipidemia, hyperglycemia, hypoglycemia, and hyperinsulinemia. In certain embodiments, a subject having a metabolic disorder has a fatty liver disease. In certain embodiments, fatty liver diseases include, but are not limited to, non-alcoholic fatty liver disease (NAFLD), alcoholic fatty liver disease, and non-alchoholic steatohepatitis (NASH).

The present invention provides a novel structure that allows administration of a single compound, which comprises a modified oligonucleotide comprising two or more regions, each of which is targeted to a microRNA (which may be the same or different). The modified oligonucleotide comprises one or more phosphodiester bonds and/or unmodified nucleosides between the regions, which allow for at least partial degradation of the modified oligonucleotide into its separate regions, e.g., in a target tissue, thereby allowing each region to target its respective microRNA separately in the target tissue.

The activity of a modified oligonucleotide is based on the specific hybridization event that occurs between a modified oligonucleotide and its target RNA and produces a desired pharmacological endpoint. In order for this to occur, certain pharmacokinetic processes must take place, for example, delivery of an intact drug to the target cell or tissue, and entry of the modified oligonucleotide into the cell containing the target RNA. Modified oligonucleotides may be conjugated to one or more moieties which improve delivery to the target cell or tissue and/or cellular uptake of the oligonucleotide, ultimately resulting in enhanced potency. For example, increased cellular uptake of compounds may be achieved by utilizing conjugates that are ligands for cell-surface receptors. The binding of a ligand conjugated to an exogenous molecule (e.g., a drug) to its cell surface receptor leads to receptor-mediated endocytosis of the conjugated molecule, thereby facilitating transmembrane transport of the exogenous molecule. For example, the targeted delivery to hepatocyte cells may be achieved by covalently attaching a conjugate comprising a carbohydrate moiety to a modified oligonucleotide. Upon recognition and binding of the carbohydrate moiety by the asialoglycoprotein receptor present on the surface of a hepatocyte cell, the conjugated modified oligonucleotide is transported across the cell membrane into the hepatocyte. By improving delivery in this manner, the potency of the modified oligonucleotide can be enhanced, as a lower does of compound is required to achieve the desired pharmacological endpoint.

Certain conjugates described herein have the advantage of providing improved delivery to target cell types and also being cleavable in vivo to produce the unconjugated modified oligonucleotide upon in vivo administration. As described above, in vivo targeting to a specific tissue or cell type may be enhanced by using a conjugate moiety. Once the conjugated modified oligonucleotide reaches its site of action, however, the presence of all or part of the covalently-linked conjugate moiety may alter the activity of certain conjugated modified oligonucleotides or may impact the analyses required to understand certain pharmacokinetic properties of the modified oligonucleotide, such as half-life in the target cell. As such, it may be desirable to administer a compound comprising a modified oligonucleotide attached to a conjugate moiety that is sufficiently stable to improve cellular uptake, but also allows for cleavage of the conjugate moiety once the compound has been internalized by the target cell. Accordingly, provided herein are compounds comprising a modified oligonucleotide linked to a cleavable conjugate moiety, which improve the potency of the modified oligonucleotide and permit partial or completed release of the modified oligonucleotide in its unconjugated form.

In certain embodiments, provided herein is a compound comprising a modified oligonucleotide having two regions, each of which is targeted to miR-103 and miR-107. The compound is efficacious in experimental models of diabetes, as evidenced by reduced glucose levels, improved HOMA-IR and improved insulin sensitivity. The compound additionally results in decreased liver triglyceride levels. The compound has been optimized based on several criteria, including efficacy, safety, viscosity in solution, and cross-reactivity with non-specific microRNA sequences.

In certain embodiments, provided herein are methods for reducing blood glucose levels in a subject comprising administering to the subject a compound described herein, wherein the compound comprises a modified oligonucleotide having at least one region consisting of 7 to 12 linked nucleosides and having a nucleobase sequence complementary to miR-103 and/or miR-107. In some embodiments, the compound comprises a modified oligonucleotide having two regions, wherein each region consists of 7 to 12 linked nucleosides and has a nucleobase sequence complementary to miR-103 and/or miR-107. In some embodiments, each region consists of 10 linked nucleosides and has a nucleobase sequence complementary to miR-103 and/or miR-107.

In some embodiments, a compound comprises the structure:

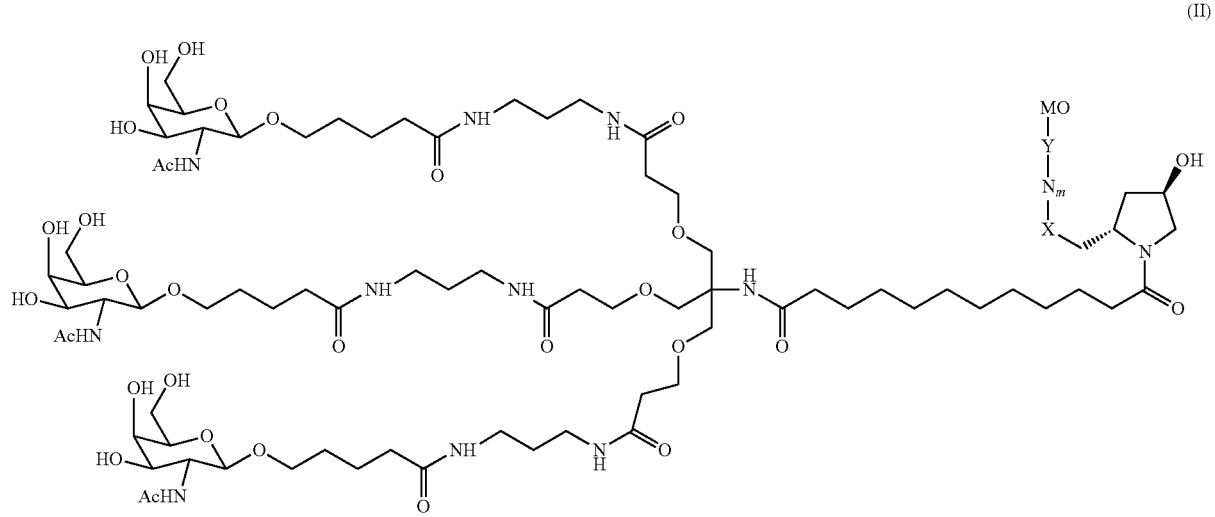

(II)

wherein X is a phosphodiester linkage; each N of $N_m$ is a deoxyadenosine (A); m is 2; Y is a phosphodiester linkage; and MO is 5'-$C_SA_SA_SU_SG_SC_SU_SG_SC_SA_S$AA$C_SA_S$$A_SU_SG_SC_SU_SG_SC_SA_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages. In certain embodiments, Y is linked to the 3' terminus of MO.

In certain embodiments, provided herein are methods for reducing blood glucose levels in a subject comprising administering to the subject a compound described herein.

In certain embodiments, the methods provided herein comprise measuring blood glucose levels. Blood glucose levels may be measured before and/or after administration of a compound described herein. Blood glucose levels may be measured in whole blood, or may be measured in plasma. Blood glucose levels may be measured in a clinical laboratory, or may be measured using a blood glucose meter.

In certain embodiments, blood glucose levels are measured in a subject when the subject has fasted for at least 8 hours. In certain embodiments, blood glucose levels are measured at random times, and the measurement is not timed according to the intake of food or drink. In certain embodiments, blood glucose levels are measured in the post-prandial state, i.e. after the subject has eaten a meal. In certain embodiments, blood glucose levels are measured in a subject two hours after the subject has eaten a meal. In certain embodiments, blood glucose levels are measured at timed intervals following administration of glucose to the subject, in order to determine how quickly the subject's body clears glucose from the blood. Any measurements of blood glucose levels may be made in whole blood or in plasma.

In certain embodiments, the subject has elevated blood glucose levels. In certain embodiments, a subject is identified as having elevated blood glucose levels. Such identification is typically made by a medical professional. In certain embodiments, an elevated blood glucose levels is a fasting blood glucose level between 100 and 125 mg/dL. In certain embodiments, an elevated blood glucose level is a fasting blood glucose level above 126 mg/dL. In certain embodiments, an elevated blood glucose level is a two-hour post-prandial glucose level between 140 and 199 mg/dL. In certain embodiments, an elevated blood glucose level is a two-hour post-prandial glucose level at 200 mg/dL or higher.

In certain embodiments, a subject having elevated blood glucose levels has pre-diabetes. In certain embodiments, a subject is identified as having pre-diabetes. In certain such embodiments, the subject has a fasting blood glucose level between 100 and 125 mg/dL. In certain such embodiments, the subject has a two-hour post-prandial blood glucose level between 140 and 199 mg/dL. A diagnosis of pre-diabetes is typically made by a medical professional, who may consider factors in addition to blood glucose levels when determining whether a subject has pre-diabetes.

In certain embodiments, a subject having elevated blood glucose levels has diabetes. In certain embodiments, a subject is identified as having diabetes according to the subject's blood glucose levels. In certain such embodiments, the subject has a fasting blood glucose level above 126 mg/dL. In certain such embodiments, the subject has a two-hour post-prandial blood glucose level at or above 200 mg/dL. A diagnosis of diabetes is typically made by a medical professional, who may consider factors in addition to blood glucose levels when determining whether a subject has diabetes.

In certain embodiments, the method provided herein comprises monitoring blood glucose levels before administration of a compound described herein. In certain embodiments, the methods provided herein comprise measuring blood glucose levels after administration of a compound described herein. In certain embodiments, a subject measures blood glucose levels one or more times daily.

In certain embodiments, methods for reducing blood glucose levels comprise reducing a subject's blood glucose levels to blood glucose levels determined as desirable by medical organizations, such as the American Diabetes Association or the World Health Organization. In certain embodiments, blood glucose levels are reduced below 130 mg/dL when measured before a subject has had a meal. In certain embodiments, blood glucose levels are reduced to below 180 mg/dL when measured after a subject has had a meal.

In certain embodiments, the administration occurs at least once per week. In certain embodiments, the administration occurs once every two weeks. In certain embodiments, the administration occurs once every three weeks. In certain embodiments, the administration occurs once every four weeks. The frequency of administration may be set by a medical professional to achieve a desirable blood glucose level in a subject. The frequency of administration may be dependent upon a subject's blood glucose levels. For example, in certain embodiments, administration may be more frequent when a subject has elevated blood glucose levels.

In certain embodiments, a dosing regimen may include doses during a loading period and/or a maintenance period. During the loading period, which in some embodiments occurs at the initiation of therapy and may last, for example, one to three weeks or more, a single administration may be given or multiple administrations may be given every day, every 2 days, every 3 days, every 4 days, every 5 days, every 6 days, or every week. During a maintenance period, which in some embodiments follows the loading period and may last for a number of months or years, or for the duration of the lifetime of the subject, doses may be given at a frequency ranging from every day to every 3 months, which is understood to include every day, every 2 days, every 3 days, every 4 days, every 5 days, every 6 days, every week, every 2 weeks, every 3 weeks, every 4 weeks, every month, every 2 months, or every 3 months. In some embodiments, the loading period comprises administration of larger doses and/or more frequent doses than the maintenance period.

Measurements of HbA1c levels may be used to determine how well a subject's blood glucose levels are controlled over time. HbA1c levels are an indication of the amount of glycated hemoglobin in the blood, and can provide an estimate of how well a subject's blood glucose levels have been managed over 2-3 month period prior to the measurement of HbA1c levels. High HbA1c levels may put a subject at risk for developing complications related to diabetes, such as eye disease, heart disease, kidney disease, nerve damage, or stroke. As such, in certain embodiments it is desirable that a subject's HbA1c levels be within ranges that are considered normal by a medical professional. In certain embodiments, an HbA1c level of 6% or less is normal. In certain embodiments, a medical professional may recommend that a subject's HbA1c level be 7% or less. In certain embodiments, the administering results in reduced HbA1c levels. In certain embodiments, the administering reduces the HbA1c level of a subject to below 8%, to below 7.5%, to below 7%, to below 6.5%, to below 6%, to below 5.5%, to below 5%, or to below 4.5%.

In certain embodiments, a subject having elevated blood glucose levels is insulin resistant. One of the main functions of insulin is to lower blood glucose levels. A subject whose cells are sensitive to the effects of insulin needs only a relatively small amount of insulin to keep blood glucose levels in the normal range. A subject who is insulin resistant requires more insulin to get the same blood glucose-lowering effects. Insulin resistance may cause hyperinsulinemia. Hyperinsulinemia may be associated with high blood pressure, heart disease and heart failure, obesity (particularly abdominal obesity), osteoporosis, and certain types of cancer, such as colon, breast, and prostate cancer.

Insulin resistance may be detected using a procedure known as the hyperinsulinemic euglycemic clamp, which measures the amount of glucose necessary to compensate for an increased insulin level without causing hypoglycemia. During the procedure, insulin is infused at 10-120 mU per m2 per minute. In order to compensate for the insulin infusion, a 20% solution of glucose is infused to maintain blood sugar levels between 5 and 5.5 mmol/L. The rate of glucose infusion is determined by checking the blood sugar levels every 5 to 10 minutes. Low-dose insulin infusions are more useful for assessing the response of the liver, whereas high-dose insulin infusions are useful for assessing peripheral (i.e., muscle and fat) insulin action. The rate of glucose infusion during the last 30 minutes of the test determines insulin sensitivity. If high levels (7.5 mg/min or higher) are required, the subject is insulin-sensitive. Very low levels (4.0 mg/min or lower) indicate that the subject is resistant to insulin action. Levels between 4.0 and 7.5 mg/min are not definitive and suggest impaired glucose tolerance. Impaired glucose tolerance may be an early sign of insulin resistance. Glucose tracers, such as 3-3H glucose, 6,6 2H-glucose, or 1-13C glucose, may be used in the procedure. Other radioactive forms of glucose may be employed in a research setting. Prior to beginning the hyperinsulinemic period, a 3 hour tracer infusion enables the determination of the basal rate of glucose production. During the clamp procedure, the plasma tracer concentrations enable the calculation of whole-body insulin-stimulated glucose metabolism, as well as the production of glucose by the body (i.e., endogenous glucose production).

In certain embodiments, provided herein are methods for improving insulin resistance in a subject comprising administering to the subject a compound described herein. In certain embodiments, the subject has insulin resistance. In certain embodiments, the methods comprise selecting a subject having insulin resistance. In certain embodiments, a subject having elevated blood glucose levels has insulin resistance. In certain embodiments, a subject having diabetes has insulin resistance. In certain embodiments, a subject having type 2 diabetes has insulin resistance. In certain embodiments, a subject having type 1 diabetes has insulin resistance.

In certain embodiments, provided herein are methods for reducing gluconeogenesis in a subject comprising administering to the subject a compound described herein. In certain embodiments, the subject has elevated gluconeogenesis. In certain embodiments, the subject is identified as having elevated gluconeogenesis. In certain embodiments, the administering results in a reduction in gluconeogenesis. In certain embodiments, a pyruvate tolerance test is used to measure gluconeogenesis in a subject. In certain embodiments, blood glucose levels are used to measure gluconeogenesis in a subject. In certain embodiments, the rate of gluconeogenesis is measured in a subject. In certain embodiments, a reduction in gluconeogenesis is a reduction in the rate of gluconeogenesis. In certain embodiments, the rate of gluconeogenesis is measured in the subject prior to administration. In certain embodiments, the rate of gluconeogenesis is measured in the subject after administration.

In certain embodiments, provided herein are methods for reducing plasma cholesterol in a subject comprising administering to the subject a compound described herein. In certain embodiments, the subject has elevated plasma cholesterol. In certain embodiments, the subject is identified as having elevated plasma cholesterol. In certain embodiments, the administering reduces plasma cholesterol. In certain embodiments, the plasma cholesterol is plasma LDL-cholesterol. In certain embodiments, the plasma cholesterol is plasma VLDL-cholesterol.

In certain embodiments, provided herein are methods for treating a metabolic disorder in a subject comprising administering to the subject a compound described herein. In certain embodiments, the subject has a metabolic disorder. In certain embodiments, the subject is identified as having a metabolic disorder. In certain embodiments, a metabolic disorder includes, without limitation, prediabetes, diabetes (including Type 1 or Type 2 diabetes), metabolic syndrome, obesity, or diabetic dyslipidemia, hyperglycemia, hypoglycemia, and hyperinsulinemia. In certain embodiments, the subject is diagnosed with one or more metabolic disorders. A subject may be diagnosed with a metabolic disorder following the administration of medical tests well-known to those in the medical profession.

Fatty liver diseases are often associated with metabolic disorders. In certain embodiments, a subject having a metabolic disorder has a fatty liver disease. In certain embodiments, a fatty liver disease is non-alcoholic fatty liver disease (NAFLD). In certain embodiments, a fatty liver disease is alcoholic fatty liver disease. In certain embodiments, a fatty liver disease is alcoholic steatohepatitis. In certain embodiments, a fatty liver disease is non-alcoholic steatohepatitis (NASH).

In certain embodiments, provided herein are methods for treating fatty liver disease in a subject comprising administering to the subject a compound described herein. In certain embodiments, the fatty liver disease is selected from non-alcoholic fatty liver disease (NAFLD), alcoholic fatty liver disease, alcoholic steatohepatitis, and non-alcoholic steatohepatitis (NASH). In certain embodiments, the fatty liver disease is selected from non-alcoholic fatty liver disease (NAFLD) and non-alcoholic steatohepatitis (NASH). In certain embodiments, provided herein are methods for treating a subject having NAFLD and type 2 diabetes. In certain embodiments, provided herein are methods for treating a subject having NASH and type 2 diabetes.

In certain embodiments, provided herein are methods of reducing liver triglycerides comprising administering to the subject a compound described herein. In some embodiments, the subject has fatty liver disease. In certain embodiments, the fatty liver disease is selected from non-alcoholic fatty liver disease (NAFLD), alcoholic fatty liver disease, alcoholic steatohepatitis, and non-alcoholic steatohepatitis (NASH). In certain embodiments, the fatty liver disease is selected from non-alcoholic fatty liver disease (NAFLD) and non-alcoholic steatohepatitis (NASH).

In certain embodiments, provided herein are methods for preventing the onset of a metabolic disorder in a subject comprising administering to the subject a compound described herein. In certain embodiments, the subject is at risk for developing a metabolic disorder. In certain embodiments, the subject is identified being at risk for developing a metabolic disorder. In certain embodiments, a metabolic disorder is prediabetes, diabetes (including Type 1 or Type 2 diabetes), metabolic syndrome, obesity, or diabetic dyslipidemia, hyperglycemia, hypoglycemia, hyperinsulinemia, ketoacidosis and celiac disease.

In certain embodiments, provided herein are methods for delaying the onset of a metabolic disorder in a subject comprising administering to the subject a compound described herein. In certain embodiments, the subject is at risk for developing a metabolic disorder. In certain embodiments, the subject is identified being at risk for developing a metabolic disorder. In certain embodiments, a metabolic disorder includes, without limitation, prediabetes, diabetes (including Type 1 or Type 2 diabetes), metabolic syndrome, obesity, or diabetic dyslipidemia, hyperglycemia, hypoglycemia, and hyperinsulinemia.

In certain embodiments, a subject has one or more metabolic disorders. In certain embodiments, a subject has been diagnosed with one or more metabolic disorders. A subject may be diagnosed with a metabolic disorder following the administration of medical tests well-known to those in the medical profession.

A subject's response to treatment may be evaluated by tests similar to those used to diagnosis the metabolic disorder, including blood glucose level tests, glucose tolerance tests, and HbA1c tests. Response to treatment may also be assessed by comparing post-treatment test results to pretreatment test results.

Fatty liver diseases may be associated with metabolic disorders. In certain embodiments, a fatty liver disease is non-alcoholic fatty liver disease (NAFLD). In certain embodiments, a fatty liver disease is alcoholic fatty liver disease. In certain embodiments, a fatty liver disease is alcoholic steatohepatitis. In certain embodiments, a fatty liver disease is non-alcoholic steatohepatitis (NASH).

In certain embodiments, provided herein are methods for treating fatty liver disease in a subject comprising administering to the subject a compound described herein.

In certain embodiments, provided herein are methods for preventing a fatty liver disease in a subject comprising administering to the subject a compound described herein. In certain such embodiments, the subject is at risk for developing a fatty liver disease.

In certain embodiments, provided herein are methods for delaying the onset of a fatty liver disease in a subject comprising administering to the subject a compound described herein. In certain such embodiments, the subject is at risk for developing a fatty liver disease.

Certain Compounds and Modified Oligonucleotides and Regions of Modified Oligonucleotides In some embodiments, a compound comprising a modified oligonucleotide having the structure:

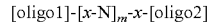

is provided. In some embodiments, a compound comprising a modified oligonucleotide consisting of the structure [oligo1][x-N]$_m$-x-[oligo2] is provided. In some embodiments, oligo1 consists of 7 to 15 linked nucleosides and has a nucleobase sequence that is complementary to the nucleobase sequence of miR-103 and/or miR-107 with no more than 1 mismatch; oligo2 consists of 7 to 15 linked nucleosides and has a nucleobase sequence that is complementary to the nucleobase sequence of miR-103 and/or miR-107 with no more than 1 mismatch; each x is independently selected from a phosphodiester bond and a phosphorothioate bond; each N is independently selected from a modified nucleoside and an unmodified nucleoside; m is an integer from 1 to 5; and at least one x is a phosphodiester bond. In some embodiments, the modified oligonucleotide consists of 15 to 32, 15 to 30, 15 to 28, 15 to 26, 15 to 24, or 15 to 22, or 15 to 20 nucleosides. In some embodiments, oligo1 has a nucleobase sequence that is at least 80%, at least 90%, or 100% complementary to the nucleobase sequence of miR-103 and/or miR-107. In some embodiments, oligo1 has a nucleobase sequence that is at least 80%, at least 90%, or 100% complementary to the nucleobase sequence of miR-103 and miR-107. In some embodiments, oligo1 has a nucleobase sequence that is complementary to at least 6, at least 7, or 8 nucleotides of the seed region of miR-103 and/or miR-107. In some embodiments, oligo1 has a nucleobase sequence that is complementary to at least 6, at least 7, or 8 nucleotides of the seed region of miR-103 and miR-107. In some embodiments, oligo2 has a nucleobase sequence that is at least 80%, at least 90%, or 100% complementary to the nucleobase sequence of miR-103 and/or miR-107. In some embodiments, oligo2 has a nucleobase sequence that is at least 80%, at least 90%, or 100% complementary to the nucleobase sequence of miR-103 and miR-107. In some embodiments, oligo2 has a nucleobase sequence that is complementary to at least 6, at least 7, or 8 nucleotides of the seed region of miR-103 and/or miR-107. In some embodiments, oligo2 has a nucleobase sequence that is complementary to at least 6, at least 7, or 8 nucleotides of the seed region of miR-103 and miR-107.

In some embodiments, at least 2 x are phosphodiester bonds. In some embodiments, each x is a phosphodiester bond. In some embodiments, at least one N is an unmodified nucleoside. In some embodiments, at least one N is an unmodified deoxyribonucleoside. In some embodiments, at least one N is an unmodified ribonucleoside. In some embodiments, each N is an unmodified nucleoside. In some embodiments, each N is an unmodified deoxyribonucleoside. In some embodiments, each N is an unmodified ribonucleoside. In some embodiments, m is 1, 2, 3, 4, or 5. In some embodiments, m is 1, 2, or 3. In some embodiments, m is 1, N is an unmodified deoxyribonucleoside, and each x is a phosphodiester bond. In some embodiments, m is 2, each N is an unmodified deoxyribonucleoside, and each x is a phosphodiester bond.

In some embodiments, oligo1 and oligo2 have the same nucleobase sequence. In such embodiments, the pattern and/or number of nucleoside modifications in oligo1 and oligo2 may be the same or different. In some embodiments, oligo1 and oligo2 have different nucleobase sequences. In some such embodiments, oligo1 and oligo2 may target overlapping or non-overlapping regions of the microRNAs.

In some embodiments, a compound comprising a modified oligonucleotide having the structure:

is provided. In some embodiments, a compound comprising a modified oligonucleotide consisting of the structure: [oligo1]-[x-N]$_m$-x-[oligo2]-[x-N]$_m$-x-[oligo3] is provided. In some embodiments, oligo1 consists of 7 to 15 linked nucleosides and has a nucleobase sequence that is complementary to the nucleobase sequence of miR-103 and/or miR-107 with no more than 1 mismatch; oligo2 consists of 7 to 15 linked nucleosides and has a nucleobase sequence that is complementary to the nucleobase sequence of miR-103 and/or miR-107 with no more than 1 mismatch; oligo3 consists of 7 to 15 linked nucleosides and has a nucleobase sequence that is complementary to the nucleobase sequence of a third microRNA with no more than 1 mismatch; each x is independently selected from a phosphodiester bond and a phosphorothioate bond; each N is independently selected from a modified nucleoside and an unmodified nucleoside; each m is independently an integer from 1 to 5; and at least one x is a phosphodiester bond. In some embodiments, the third microRNA is miR-103 and/or miR-107.

In some embodiments, at least one x between oligo1 and oligo2 is a phosphodiester bond and at least one x between oligo2 and oligo3 is a phosphodiester bond. In some embodiments, each x is a phosphodiester bond. In some embodiments, the modified oligonucleotide consists of 23 to 55, 23 to 50, 23 to 45, 23 to 40, 23 to 35, 23 to 30, or 23 to 26 nucleosides. In some embodiments, oligo1 has a nucleobase sequence that is at least 80%, at least 90% or 100% complementary to the nucleobase sequence of miR-103 and/or miR-107. In some embodiments, oligo1 has a nucleobase sequence that is complementary to at least 6, at least 7, or 8 nucleotides of the seed region of miR-103 and/or miR-107. In some embodiments, oligo2 has a nucleobase sequence that is at least 80%, at least 90% or 100% complementary to the nucleobase sequence of miR-103 and/or miR-107. In some embodiments, oligo2 has a nucleobase sequence that is complementary to at least 6, at least 7, or 8 nucleotides of the seed region of miR-103 and/or miR-107. In some embodiments, oligo3 has a nucleobase sequence that is at least 80%, at least 90% or 100% complementary to the nucleobase sequence of the third microRNA. In some embodiments, oligo3 has a nucleobase sequence that is complementary to at least 6, at least 7, or 8 nucleotides of the seed region of the third microRNA.

In some embodiments, at least 4 x are phosphodiester bonds. In some embodiments, at least 2 x between oligo1 and oligo2 are phosphodiester bonds and at least 2 x between oligo2 and oligo3 are phosphodiester bonds. In some embodiments, each x is a phosphodiester bond. In some embodiments, at least one N is an unmodified nucleoside. In some embodiments, at least one N between oligo1 is an unmodified nucleoside, and at least one N between oligo2 and oligo3 is an unmodified nucleoside. In some embodiments, each N is an unmodified nucleoside. In some embodiments, each m is independently selected from 1, 2, 3, 4, and 5. In some embodiments, each m is independently selected from 1, 2, or 3. In some embodiments, each m is 1, each N is an unmodified deoxyribonucleoside, and each x is a phosphodiester bond. In some embodiments, one or both m is 2, each N is an unmodified deoxyribonucleoside, and each x is a phosphodiester bond.

In some embodiments, at least two or all three of the first microRNA, the second microRNA, and the third microRNA are the same. In some embodiments, the first microRNA, the second microRNA, and the third microRNA are each different from one another. In some embodiments when at least two of the microRNA are the same, the corresponding oligos have the same nucleobase sequence. In such embodiments, the pattern and/or number of nucleoside modifications in the oligos with the same nucleobase sequence may be the same or different. In some embodiments when at least two microRNAs are the same, the corresponding oligos have different nucleobase sequences. In some such embodiments, the oligos targeted to the same microRNA may target overlapping or non-overlapping regions of the microRNA.

In some embodiments, oligo1 consists of 7 to 15 linked nucleosides, 7 to 14 linked nucleosides, 7 to 13 linked nucleosides, 7 to 12 linked nucleosides, 7 to 11 linked nucleosides, 7 to 10 linked nucleosides, 8 to 15 linked nucleosides, 8 to 14 linked nucleosides, 8 to 13 linked nucleosides, 8 to 12 linked nucleosides, 8 to 11 linked nucleosides, or 8 to 10 linked nucleosides. In some embodiments, oligo1 consists of 9 linked nucleosides. In some embodiments, oligo1 consists of 10 linked nucleosides.

In some embodiments, oligo1 comprises at least one nucleoside with a modified sugar moiety. In some embodiments, oligo1 comprises at least one nucleoside with an unmodified sugar moiety. In some embodiments, oligo1 comprises a plurality of nucleosides with a modified sugar moiety, and a plurality of nucleosides with an unmodified sugar moiety. In some embodiments, at least 4, at least 5, at least 6, at least 7, or at least 8 nucleosides of oligo1 have a modified sugar moiety. In some embodiments, each nucleoside of oligo1 has a modified sugar moiety. In some embodiments, each modified nucleoside is independently selected from a 2'-O-methyl sugar moiety, a 2'-O-methoxyethyl sugar moiety, a 2'-fluoro sugar moiety, and a bicyclic sugar moiety. In some embodiments, each bicyclic sugar moiety is independently selected from a cEt sugar moiety and an LNA sugar moiety. In some embodiments, each unmodified sugar moiety is independently selected from a β-D-deoxyribose and a β-D-ribose. In some embodiments, oligo1 comprises at least at least 4, at least 5, at least 6, at least 7, or at least 8 bicyclic nucleosides. In some embodiments, oligo1 comprises at least 4, at least 5, at least 6, at least 7, or at least 8 cEts. In some embodiments, oligo1 comprises at least 4, at least 5, at least 6, at least 7, or at least 8 LNAs. In some embodiments, oligo1 consists of 10 linked bicyclic nucleosides. In some such embodiments, each bicyclic nucleoside is independently selected from cEt and LNA. In some embodiments, each bicyclic nucleoside is cEt.

In some embodiments, oligo2 consists of 7 to 15 linked nucleosides, 7 to 14 linked nucleosides, 7 to 13 linked nucleosides, 7 to 12 linked nucleosides, 7 to 11 linked nucleosides, 7 to 10 linked nucleosides, 8 to 15 linked nucleosides, 8 to 14 linked nucleosides, 8 to 13 linked nucleosides, 8 to 12 linked nucleosides, 8 to 11 linked nucleosides, or 8 to 10 linked nucleosides. In some embodiments, oligo2 consists of 9 linked nucleosides. In some embodiments, oligo2 consists of 10 linked nucleosides.

In some embodiments, oligo2 comprises at least one nucleoside with a modified sugar moiety. In some embodiments, oligo2 comprises at least one nucleoside with an unmodified sugar moiety. In some embodiments, oligo2 comprises a plurality of nucleosides with a modified sugar moiety, and a plurality of nucleosides with an unmodified sugar moiety. In some embodiments, at least 4, at least 5, at least 6, at least 7, or at least 8 nucleosides of oligo2 have a modified sugar moiety. In some embodiments, each nucleoside of oligo2 has a modified sugar moiety. In some embodiments, each modified nucleoside is independently selected from a 2'-O-methyl sugar moiety, a 2'-O-methoxyethyl sugar moiety, a 2'-fluoro sugar moiety, and a bicyclic sugar moiety. In some embodiments, each bicyclic sugar moiety is independently selected from a cEt sugar moiety and an LNA sugar moiety. In some embodiments, each unmodified sugar moiety is independently selected from a β-D-deoxyribose and a β-D-ribose. In some embodiments, oligo2 comprises at least at least 4, at least 5, at least 6, at least 7, or at least 8 bicyclic nucleosides. In some embodiments, oligo2 comprises at least at least 4, at least 5, at least 6, at least 7, or at least 8 cEts. In some embodiments, oligo2 comprises at least at least 4, at least 5, at least 6, at least 7, or at least 8 LNAs. In some embodiments, oligo2 consists of 10 linked bicyclic nucleosides. In some such embodiments, each bicyclic nucleoside is independently selected from cEt and LNA. In some embodiments, each bicyclic nucleoside is cEt. In some embodiments, oligo1 and oligo2 have the same nucleobase sequence and each consists of 10 linked cEt nucleosides.

In some embodiments, oligo3 consists of 7 to 15 linked nucleosides, 7 to 14 linked nucleosides, 7 to 13 linked nucleosides, 7 to 12 linked nucleosides, 7 to 11 linked nucleosides, 7 to 10 linked nucleosides, 8 to 15 linked nucleosides, 8 to 14 linked nucleosides, 8 to 13 linked nucleosides, 8 to 12 linked nucleosides, 8 to 11 linked nucleosides, or 8 to 10 linked nucleosides.

In some embodiments, oligo3 comprises at least one nucleoside with a modified sugar moiety. In some embodiments, oligo3 comprises at least one nucleoside with an unmodified sugar moiety. In some embodiments, oligo3 comprises a plurality of nucleosides with a modified sugar moiety, and a plurality of nucleosides with an unmodified sugar moiety. In some embodiments, at least 4, at least 5, at least 6, at least 7, or at least 8 nucleosides of oligo3 have a modified sugar moiety. In some embodiments, each nucleoside of oligo3 has a modified sugar moiety. In some embodiments, each modified nucleoside is independently selected from a 2'-O-methyl sugar moiety, a 2'-O-methoxyethyl sugar moiety, a 2'-fluoro sugar moiety, and a bicyclic sugar moiety. In some embodiments, each bicyclic sugar moiety is independently selected from a cEt sugar moiety and an LNA sugar moiety. In some embodiments, each unmodified sugar moiety is independently selected from a β-D-deoxyribose and a β-D-ribose. In some embodiments, oligo3 comprises at least at least 4, at least 5, at least 6, at least 7, or at least 8 bicyclic nucleosides. In some embodiments, oligo3 comprises at least at least 4, at least 5, at least 6, at least 7, or at least 8 cEts. In some embodiments, oligo3 comprises at least at least 4, at least 5, at least 6, at least 7, or at least 8 LNAs.

In some embodiments, the first microRNA and second microRNA, and, when present, the third microRNA, are each miR-103/107. In some embodiments, oligo1 and/or oligo2 has the nucleobase sequence 5'-CAAUGCUGCA-3' (SEQ ID NO: 6). In some embodiments, oligo1 and oligo2 each has the nucleobase sequence 5'-CAAUGCUGCA-3' (SEQ ID NO: 6). In some embodiments, the compound comprises a modifiedoligonucleotide consisting of the sequence 5'-$C_SA_SA_SU_SG_SC_SU_SG_SC_SA_S$AAC$_SA_SA_SU_SG_SC_SU_SG_SC_SA_S$-3' (SEQ ID NO: 7), wherein oligo 1 is 5'-$C_SA_SA_SU_SG_SC_SU_SG_SC_SA_S$-3' (SEQ ID NO: 6), oligo 2 is 5'-$C_SA_SA_SU_SG_SC_SU_SG_SC_SA_S$-3' (SEQ ID NO: 6), and oligo1 and oligo2 are linked by AA, wherein each nucleoside followed by a subscript "S" is a S-cEt nucleoside and each nucleoside not followed by a subscript is a deoxynucleoside.

In some embodiments, oligo1 and/or oligo2 has the nucleobase sequence 5'-CAAUGCUGCC-3' (SEQ ID NO: 8). In some embodiments, oligo1 and oligo2 each has the nucleobase sequence 5'-CAAUGCUGCC' (SEQ ID NO: 8). In some embodiments, the compound comprises a modified oligonucleotide consisting of the sequence 5'-$C_SA_S$$A_SU_SG_SC_SU_SG_SC_SC_S$AAC$_SA_SA_SU_SG_SC_SU_SG_SC_SC_S$-3' (SEQ ID NO: 9), wherein oligo 1 is 5'-$C_SA_SA_SU_S$$G_SC_SU_SG_SC_SC_S$-3' (SEQ ID NO: 8), oligo 2 is 5'-$C_S$$A_SA_SU_SG_SC_SU_SG_SC_SC_S$-3' (SEQ ID NO: 8), and oligo1 and oligo2 are linked by AA, wherein each nucleoside followed by a subscript "S" is a S-cEt nucleoside and each nucleoside not followed by a subscript is a deoxynucleoside. In some embodiments, oligo1 and/or oligo2 has the nucleobase sequence 5'-CAAUGCUGCG-3' (SEQ ID NO: 10). In some embodiments, oligo1 and oligo2 each has the nucleobase sequence 5'-CAAUGCUGCAG-3' (SEQ ID NO: 10). In some embodiments, the compound comprises a modified oligonucleotide consisting of the sequence 5'-$C_SA_S$ $A_SU_SG_SC_SU_SG_SC_SC_SG_S$AAC$_SA_SA_SU_SG_SC_SU_SG_SC_SG_S$-3' (SEQ ID NO: 11), wherein oligo 1 is 5'-$C_SA_SA_SU_SG_S$ $C_SU_SG_SC_SG_S$-3' (SEQ ID NO: 10), oligo 2 is 5'-$C_SA_S$ $A_SU_SG_SC_SU_SG_SC_SG_S$-3' (SEQ ID NO: 10), and oligo1 and oligo2 are linked by AA, wherein each nucleoside followed by a subscript "S" is a S-cEt nucleoside and each nucleoside not followed by a subscript is a deoxynucleoside.

In some embodiments, the internucleoside linkages between the 3' end of oligo1 and the AA linker and between the AA linker and the 5' end of oligo2 are phosphodiester internucleoside linkages. In some embodiments, the internucleoside linkage between the As of the AA linker is also a phosphodiester internucleoside linkage. In some embodiments, all of the internucleoside linkages between nucleosides within oligo1 and oligo2 are phosphorothioate linkages (i.e., all of the internucleoside linkages between two S-cEt nucleosides are phosphorothioate linkages). In some embodiments, the 3' end of oligo2 is attached to a conjugate moiety through a linker. In some embodiments, the conjugate moiety is GalNAc. In some embodiments, the linker is an AA linker, wherein each A is a deoxyadenosine and the internucleoside linkages between oligo2 and the linker, and between the A's of the AA linker, and between the linker and the conjugate moiety, are phosphodiester linkages.

In certain embodiments, the nucleobase sequence of a region (i.e., oligo1, oligo2, or oligo3 in the structures shown herein) of a modified oligonucleotide is at least 80%, at least 85%, at least 90%, at least 91%, at least 92%, at least 95%, at least 96%, or 100% complementary to the nucleobase sequence of the target RNA. In certain embodiments, a region (i.e., oligo1, oligo2, or oligo3 in the structures shown herein) of a modified oligonucleotide is at least 90%, at least 93%, at least 94%, at least 95%, or 100% complementary to a target RNA.

In certain embodiments, a region (i.e., oligo1, oligo2, or oligo3 in the structures shown herein) of a modified oligonucleotide comprises at least one nucleoside with a modified sugar moiety. In certain embodiments, a region (i.e., oligo1, oligo2, or oligo3 in the structures shown herein) of a modified oligonucleotide comprises a plurality of non-bicyclic nucleosides and a plurality of bicyclic nucleosides.

In certain embodiments, at least 70% of the nucleosides of a region (i.e., oligo1, oligo2, or oligo3 in the structures shown herein) of a modified oligonucleotide comprise a modified sugar moiety. In certain embodiments, at least 80% of the nucleosides of a region (i.e., oligo1, oligo2, or oligo3 in the structures shown herein) of a modified oligonucleotide comprise a modified sugar moiety. In certain embodiments, at least 90% of the nucleosides of a region (i.e., oligo1, oligo2, or oligo3 in the structures shown herein) of a modified oligonucleotide comprise a modified sugar moiety. In certain embodiments, at least 95% of the nucleosides of a region (i.e., oligo1, oligo2, or oligo3 in the structures shown herein) of a modified oligonucleotide comprise a modified sugar moiety. In some embodiments, 100% of the nucleosides of a region (i.e., oligo1, oligo2, or oligo3 in the structures shown herein) of a modified oligonucleotide comprise a modified sugar moiety. In some embodiments, 100% of the nucleosides of a region (i.e., oligo1, oligo2, or oligo3 in the structures shown herein) of a modified oligonucleotide are bicyclic nucleosides. In some embodiments, 100% of the nucleosides of a region (i.e., oligo1, oligo2, or oligo3 in the structures shown herein) of a modified oligonucleotide are cEt nucleosides.

In certain embodiments, at least two bicyclic nucleosides comprise sugar moieties that are different from one another. In certain embodiments, each bicyclic nucleoside has the same type of sugar moiety. In certain embodiments, at least two non-bicyclic nucleosides comprise sugar moieties that are different from one another. In certain embodiments, each non-bicyclic nucleoside has the same type of sugar moiety.

In certain embodiments, each non-bicyclic nucleoside is independently selected from a β-D-deoxyribonucleoside, a β-D-ribonucleoside, 2'-O-methyl nucleoside, a 2'-O-methoxyethyl nucleoside, and a 2'-fluoronucleoside. In certain embodiments, each non-bicyclic nucleoside is independently selected from a β-D-deoxyribonucleoside, and a 2'-O-methoxyethyl nucleoside. In certain embodiments, each non-bicyclic nucleoside is a β-D-deoxyribonucleoside.

In certain embodiments, the bicyclic nucleoside is selected from a cEt nucleoside, and LNA nucleoside, and an ENA nucleoside. In certain embodiments, the cEt nucleoside is an S-cEt nucleoside. In certain embodiments, the cEt nucleoside is an R-cEt nucleoside.

In certain embodiments, a region (i.e., oligo1, oligo2, or oligo3 in the structures shown herein) of the modified oligonucleotide comprises a plurality of modified nucleosides and a plurality of β-D-deoxyribonucleoside, wherein each β-D-deoxyribonucleoside may comprise a modified or unmodified nucleobase. In certain embodiments, a region (i.e., oligo1, oligo2, or oligo3 in the structures shown herein) of the modified oligonucleotide is a gapmer. In certain embodiments, the sugar moiety of each nucleoside is a modified sugar moiety. In certain embodiments, a modified nucleoside is a 2'-O-methoxyethyl nucleoside. In certain embodiments, a modified nucleoside is an S-cEt nucleoside.

In certain embodiments, a modified oligonucleotide comprising two regions (i.e., comprising oligo1 and oligo2 in the structures shown herein) consists of 15, 16, 17, 18, 19, 20, 21, 22, 23, 24, 25, 26, 27, 28, 29, 30, 31, or 32 linked nucleosides. In some embodiments, the modified oligonucleotide consists of 15 to 32 linked nucleosides. In some embodiments, the modified oligonucleotide consists of 15 to 30 linked nucleosides. In some embodiments, the modified oligonucleotide consists of 15 to 28 linked nucleosides. In some embodiments, the modified oligonucleotide consists of 15 to 26 linked nucleosides. In some embodiments, the modified oligonucleotide consists of 15 to 24 linked nucleosides. In some embodiments, the modified oligonucleotide consists of 15 to 22 linked nucleosides. In some embodiments, the modified oligonucleotide consists of 15 to 20 linked nucleosides. In some embodiments, the modified oligonucleotide consists of 22 linked nucleosides. In some embodiments, the modified oligonucleotide consists of 24 linked nucleosides.

In certain embodiments, a modified oligonucleotide comprising three regions (i.e., comprising oligo1, oligo2, and oligo3 in the structures shown herein) consists of 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 linked nucleosides. In some embodiments, the modified oligonucleotide consists of 23 to 55 linked nucleosides. In some embodiments, the modified oligonucleotide consists of 23 to 50 linked nucleosides. In some embodiments, the modified oligonucleotide consists of 24 to 45 linked nucleosides. In some embodiments, the modified oligonucleotide consists of 23 to 40 linked nucleosides. In some embodiments, the modified oligonucleotide consists of 23 to 35 linked nucleosides. In some embodiments, the modified oligonucleotide consists of 23 to 30 linked nucleosides. In some embodiments, the modified oligonucleotide consists of 23 to 26 linked nucleosides.

In certain embodiments, a region (i.e., oligo1, oligo2, or oligo3 in the structures shown herein) of a modified oligonucleotide consists of 7 to 15 linked nucleosides. In certain embodiments, a region of a modified oligonucleotide consists of 7 to 14 linked nucleosides. In certain embodiments, a region of a modified oligonucleotide consists of 7 to 13 linked nucleosides. In certain embodiments, a region of a modified oligonucleotide consists of 7 to 12 linked nucleosides. In certain embodiments, a region of a modified oligonucleotide consists of 7 to 11 linked nucleosides. In certain embodiments, a region of a modified oligonucleotide consists of 7 to 10 linked nucleosides. In certain embodiments, a region of a modified oligonucleotide consists of 8 to 15 linked nucleosides. In certain embodiments, a region of a modified oligonucleotide consists of 8 to 14 linked nucleosides. In certain embodiments, a region of a modified oligonucleotide consists of 8 to 13 linked nucleosides. In certain embodiments, a region of a modified oligonucleotide consists of 8 to 12 linked nucleosides. In certain embodiments, a region of a modified oligonucleotide consists of 8 to 11 linked nucleosides. In certain embodiments, a region of a modified oligonucleotide consists of 8 to 10 linked nucleosides. In certain embodiments, a region of a modified oligonucleotide consists of 7 linked nucleosides. In certain embodiments, a region of a modified oligonucleotide consists of 8 linked nucleosides. In certain embodiments, a region of a modified oligonucleotide consists of 9 linked nucleosides. In certain embodiments, a region of a modified oligonucleotide consists of 10 linked nucleosides. In certain embodiments, a region of a modified oligonucleotide consists of 11 linked nucleosides. In certain embodiments, a region of a modified oligonucleotide consists of 12 linked nucleosides. In certain embodiments, a region of a modified oligonucleotide consists of 13 linked nucleosides. In certain embodiments, a region of a modified oligonucleotide consists of 14 linked nucleosides. In certain embodiments, a region of a modified oligonucleotide consists of 15 linked nucleosides.

In certain embodiments, at least one internucleoside linkage of a region (i.e., oligo1, oligo2, and/or oligo3) of a modified oligonucleotide is a modified internucleoside linkage. In certain embodiments, each internucleoside linkage of a region (i.e., oligo1, oligo2, and/or oligo3) of a modified oligonucleotide is a modified internucleoside linkage. In certain embodiments, the modified internucleoside linkage is a phosphorothioate internucleoside linkage. In certain embodiments, at least one nucleoside of a modified oligonucleotide comprises a modified nucleobase. In certain embodiments, at least one pyrimidine of the modified oligonucleotide comprises a 5-methyl group. In certain embodiments, at least one nucleoside of a modified oligonucleotide comprises a 5-methylcytosine. In certain embodiments, each cytosine of a modified oligonucleotide is a 5-methylcytosine.

In certain embodiments, where a region (i.e., oligo1, oligo2, and/or oligo3 of the structures shown herein) of a modified oligonucleotide is between 7 and 12 linked nucleosides in length, each nucleoside of the modified oligonucleotide comprises a modified sugar moiety. In certain embodiments, where a region of modified oligonucleotide is between 7 and 10 linked nucleosides in length, each nucleoside of the modified oligonucleotide comprises a modified sugar moiety. In certain embodiments, where a region of a modified oligonucleotide is between 8 and 12 linked nucleosides, each nucleoside of the modified oligonucleotide comprises a modified sugar moiety.

In certain embodiments, a region of modified oligonucleotide consists of 7 linked nucleosides, wherein each nucleoside of the region comprises a modified sugar moiety. In certain embodiments, a region of a modified oligonucleotide consists of 8 linked nucleosides, wherein each nucleoside of the region comprises a modified sugar moiety. In certain embodiments, a region of a modified oligonucleotide consists of 9 linked nucleosides, wherein each nucleoside of the region comprises a modified sugar moiety. In certain embodiments, a region of a modified oligonucleotide consists of 10 linked nucleosides, wherein each nucleoside of the region comprises a modified sugar moiety. In certain embodiments, a region of a modified oligonucleotide consists of 11 linked nucleosides, wherein each nucleoside of the region comprises a modified sugar moiety. In certain embodiments, a region of a modified oligonucleotide consists of 12 linked nucleosides, wherein each nucleoside of the region comprises a modified sugar moiety. In certain embodiments, each nucleoside of the region comprises a bicyclic sugar moiety. In certain embodiments, the bicyclic sugar moiety is a cEt sugar moiety. In certain embodiments, the cEt sugar moiety is an S-cEt sugar moiety. In certain embodiments, the bicyclic sugar moiety is an LNA sugar moiety.

In certain embodiments, a region of a modified oligonucleotide is fully modified. In certain embodiments, a fully modified region of an oligonucleotides comprise a sugar modification at each nucleoside. In certain embodiments, a fully modified region of an oligonucleotide comprises at least one modified internucleoside linkage. In certain embodiments, a fully modified region of an oligonucleotide comprises a sugar modification at each nucleoside, and each internucleoside linkage is a modified internucleoside linkage. In certain embodiments, a fully modified region of an oligonucleotide comprises a sugar modification at each nucleoside, and comprise at least one phosphorothioate internucleoside linkage. In certain embodiments, a fully modified region of an oligonucleotide comprises a sugar modification at each nucleoside, and each internucleoside linkage is a phosphorothioate internucleoside linkage. In certain embodiments, each nucleoside of a fully modified region of an oligonucleotide comprises the same modified sugar moiety.

In certain embodiments, a region of a modified oligonucleotide is a uniformly modified oligonucleotide. In certain embodiments, each nucleoside of a uniformly modified region of an oligonucleotide comprises the same sugar modified moiety. In certain embodiments, each internucleoside linkage of a uniformly modified region of an oligonucleotide comprises the same modified internucleoside linkage.

In certain embodiments, a region of a modified oligonucleotide is a gapmer.

In certain embodiments, provided herein are compounds comprising a modified oligonucleotide consisting of a single region of 8 to 25 linked nucleosides, wherein the nucleobase sequence of the single region is complementary to miR-103 and/or miR-107, and wherein the compound comprises a conjugate moiety linked to the 5' terminus or the 3' terminus of the modified oligonucleotide, and wherein the conjugate moiety comprises a ligand that improves cellular uptake in a liver cell. In certain embodiments, provided herein are compounds comprising a modified oligonucleotide consisting of 8 to 25 linked nucleosides, wherein the nucleobase sequence of the modified oligonucleotide is complementary to miR-103 and/or miR-107, and wherein the compound comprises a conjugate moiety linked to the 5' terminus or the 3' terminus of the modified oligonucleotide, and wherein the conjugate moiety comprises a ligand that improves cellular uptake in a liver cell. In certain embodiments, the conjugate moiety comprises a ligand having affinity for the asialyglycoprotein receptor. In certain embodiments, the ligand is selected from N-acetylgalactosamine, galactose, galactosamine, N-formylgalactosamine, N-propionyl-galactosamine, N-n-butanoylgalactosamine, and N-iso-butanoylgalactosamine. In certain embodiments, a modified oligonucleotide consists of 8 to 25 linked nucleosides. In certain embodiments, a modified oligonucleotide consists of 12 to 25 linked nucleosides. In certain embodiments, a modified oligonucleotide consists of 15 to 30 linked nucleosides. In certain embodiments, a modified oligonucleotide consists of 15 to 25 linked nucleosides. In certain embodiments, a modified oligonucleotide consists of 15 to 19 linked nucleosides. In certain embodiments, a modified oligonucleotide consists of 15 to 16 linked nucleosides. In certain embodiments, a modified oligonucleotide consists of 19 to 24 linked nucleosides. In certain embodiments, a modified oligonucleotide consists of 21 to 24 linked nucleosides.

In certain embodiments, the nucleobase sequence of the single region has at least 90%, at least 95%, or has 100% complementarity to the nucleobase sequence of miR-103 and/or miR-107. In certain embodiments, the nucleobase sequence of the modified oligonucleotide has at least 90%, at least 95%, or has 100% complementarity to the nucleobase sequence of miR-103 and/or miR-107.

In certain embodiments, the modified oligonucleotide consisting of a single region has at least one modified sugar moiety, at least one modified internucleoside linkage, and/or at least one modified nucleobase, each of which may be selected from any of those described herein. In certain embodiments, the modified oligonucleotide has at least one modified sugar moiety, at least one modified internucleoside linkage, and/or at least one modified nucleobase, each of which may be selected from any of those described herein. The conjugate moiety may be selected from any of the structures described herein.

Certain Conjugated Compounds

In certain embodiments, a compound provided herein comprises a conjugate moiety linked to the 5' terminus or the 3' terminus of a modified oligonucleotide. In certain embodiments, the compound comprises a conjugate moiety linked to the 3' terminus of a modified oligonucleotide. In certain embodiments, the compound comprises a conjugate moiety linked to the 5' terminus of a modified oligonucleotide. In certain embodiments, the compound comprises a first conjugate moiety linked to a 3' terminus of the modified oligonucleotide and a second conjugate moiety linked to the 5' terminus of a modified oligonucleotide.

In certain embodiments, a conjugate moiety comprises at least one ligand selected from a carbohydrate, cholesterol, a lipid, a phospholipid, an antibody, a lipoprotein, a hormone, a peptide, a vitamin, a steroid, or a cationic lipid.

Ligands may be covalently attached to a modified oligonucleotide by any suitable linker Various linkers are known in the art, and certain nonlimiting exemplary linkers are described, e.g., in PCT Publication No. WO 2013/033230 and U.S. Pat. No. 8,106,022 B2. In some embodiments, a linker may be selected that is resistant to enzymatic cleavage in vivo. In some embodiments, a linker may be selected that is resistant to hydrolytic cleavage in vivo. In some embodiments, a linker may be selected that will undergo enzymatic cleavage in vivo. In some embodiments, a linker may be selected that will undergo hydrolytic cleavage in vivo.

In certain embodiments, a compound comprising a conjugated modified oligonucleotide described herein has the structure:

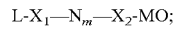

wherein each L is a ligand; each N of $N_m$ is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage. In certain embodiments, m is 1 and $X_1$ and $X_2$ are each phosphodiester.

In certain embodiments, a compound comprising a conjugated modified oligonucleotide described herein has Structure A:

$L_n$-linker-MO;

wherein each L is, independently, a ligand and n is from 1 to 10; and MO is a modified oligonucleotide.

In certain embodiments, a compound comprising a conjugated modified oligonucleotide described herein has Structure B:

$L_n$-linker-$X_1$—$N_m$—$X_2$-MO;

wherein each L is, independently, a ligand and n is from 1 to 10; each N of $N_m$ is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprising a conjugated modified oligonucleotide described herein has Structure C:

$L_n$-linker-X—$N_m$—Y-MO;

wherein each L is, independently, a ligand and n is from 1 to 10; each N of $N_m$ is, independently, a modified or unmodified nucleoside and m is from 1 to 5; X is a phosphodiester linkage or a phosphorothioate linkage; Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprising a conjugated modified oligonucleotide described herein has Structure D:

$L_n$-linker-Y—$N_m$—Y-MO;

wherein each L is, independently, a ligand and n is from 1 to 10; each N of $N_m$ is, independently, a modified or unmodified nucleoside and m is from 1 to 5; each Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, when n is greater than 1, the linker comprises a scaffold capable of linking more than one L to the remainder of the compound (i.e., to the modified oligonucleotide (MO), to $X_1$—$N_m$—$X_2$-MO, to X—$N_m$—Y-MO, etc.). In some such embodiments, the $L_n$-linker portion of the compound (such as a compound of Structure A, B, C, or D) comprises Structure E:

$$(L-Q')_n-S-Q''-$$

wherein each L is, independently, a ligand; n is from 1 to 10; S is a scaffold; and Q' and Q" are, independently, linking groups.

In some embodiments, each Q' and Q" is independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

In some embodiments, a scaffold is capable of linking 2, 3, 4, or 5 ligands to a modified oligonucleotide. In some embodiments, a scaffold is capable of linking 3 ligands to a modified oligonucleotide.

A nonlimiting exemplary Structure E is Structure E(i):

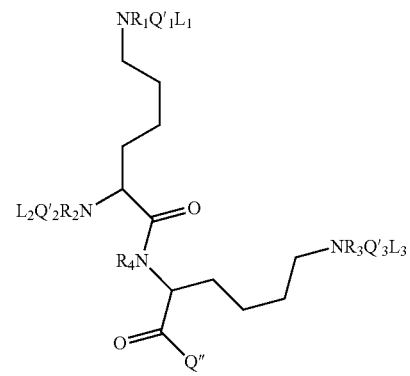

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments, $R_1$, $R_2$, $R_3$, and $R_4$ are each selected from H and methyl.

A further nonlimiting exemplary Structure E is Structure E(ii):

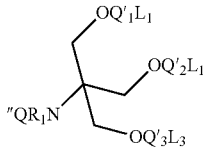

wherein $L_1$, $L_2$, and $L_3$ are each, independently, a ligand; $Q'_1$, $Q'_2$, $Q'_3$, and $Q''$ are each, independently, a linking group; and $R_1$ is selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$ is selected from H, methyl, ethyl, propyl, isopropyl, and butyl. In some embodiments, $R_1$ is H or methyl.

A further nonlimiting exemplary Structure E is Structure E(iii):

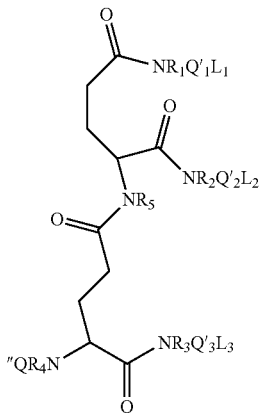

wherein $L_1$, $L_2$, and $L_3$ are each, independently, a ligand; $Q'_1$, $Q'_2$, $Q'_3$, and $Q''$ are each, independently, a linking group; and $R_1$, $R_2$, $R_3$, $R_4$, and $R_5$ are each, independently, selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, $R_4$, and $R_5$ are each, independently, selected from H, methyl, ethyl, propyl, isopropyl, and butyl. In some embodiments $R_1$, $R_2$, $R_3$, $R_4$, and $R_5$ are each selected from H and methyl.

A further nonlimiting exemplary Structure E is Structure E(iv):

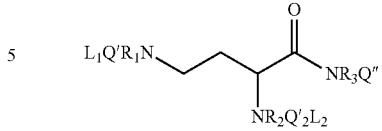

wherein $L_1$ and $L_2$ are each, independently, a ligand; $Q'_1$, $Q'_2$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(v):

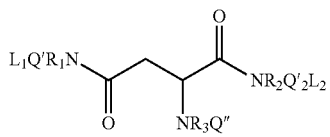

wherein $L_1$ and $L_2$ are each, independently, a ligand; $Q'_1$, $Q'_2$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vi):

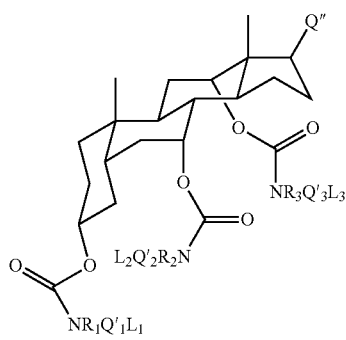

wherein $L_1$, $L_2$, and $L_3$ are each, independently, a ligand; $Q'_1$, $Q'_2$, $Q'3$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, $Q'3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vii):

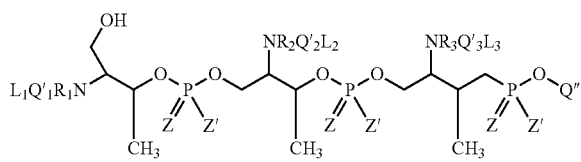

wherein $L_1$, $L_2$, and $L_3$ are each, independently, a ligand; $Q'_1$, $Q'_2$, $Q'3$, and $Q''$ are each, independently, a linking group; $R_1$, $R_2$, and $R_3$ are each, independently, selected from H, $C_1$-$C_6$ alkyl, and substituted $C_1$-$C_6$ alkyl; and Z and Z' are each independently selected from O and S.

In some embodiments, $Q'_1$, $Q'_2$, $Q'3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl. In some embodiments, Z or Z' on at least one P atom is S, and the other Z or Z' is O (i.e., a phosphorothioate linkage). In some embodiments, each —OP(Z)(Z')O— is a phosphorothioate linkage. In some embodiments, Z and Z' are both 0 on at least one P atom (i.e., a phosphodiester linkage). In some embodiments, each —OP(Z)(Z')O— is a phosphodiester linkage.

A further nonlimiting exemplary Structure E is Structure E(viii):

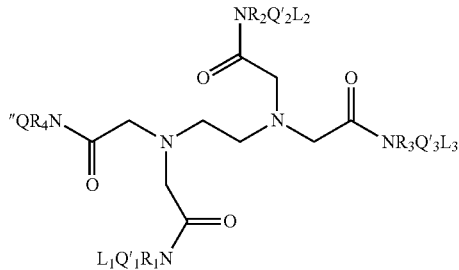

wherein $L_1$, $L_2$, and $L_3$ are each, independently, a ligand; $Q'_1$, $Q'_2$, $Q'3$, and $Q''$ are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments $R_1$, $R_2$, $R_3$, and $R_4$ are each selected from H and methyl.

Nonlimiting exemplary scaffolds and/or linkers comprising scaffolds, and synthesis thereof, are described, e.g., PCT Publication No. WO 2013/033230, U.S. Pat. No. 8,106,022 B2, U.S. Publication No. 2012/0157509 A1; U.S. Pat. No. 5,994,517; U.S. Pat. No. 7,491,805 B2; U.S. Pat. No. 8,313,772 B2; Manoharan, M., Chapter 16, Antisense Drug Technology, Crooke, S. T., Marcel Dekker, Inc., 2001, 391-469.

In some embodiments, the $L_n$-linker portion of the compound comprises Structure F:

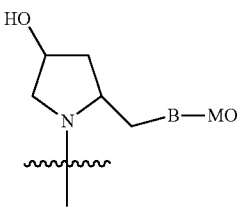

wherein:

B is selected from —O—, —S—, —N($R^N$)—, —Z—P(Z')(Z'')O—, —Z—P(Z')(Z'')O—$N_m$—X—, and —Z—P(Z')(Z'')O—$N_m$—Y—;

MO is a modified oligonucleotide;

$R^N$ is selected from H, methyl, ethyl, propyl, isopropyl, butyl, and benzyl;

Z, Z', and Z'' are each independently selected from O and S;

each N of $N_m$ is, independently, a modified or unmodified nucleoside;

m is from 1 to 5;

X is selected from a phosphodiester linkage and a phosphorothioate linkage;

Y is a phosphodiester linkage; and the wavy line indicates the connection to the rest of the linker and ligand(s).

In certain embodiments, the wavy line indicates a connection to Structure E, above.

In certain embodiments, n is from 1 to 5, 1 to 4, 1 to 3, or 1 to 2. In certain embodiments, n is 1. In certain embodiments, n is 2. In certain embodiments, n is 3. In certain embodiments, n is 4. In certain embodiments, n is 5.

In some embodiments, the $L_n$-linker portion of the compound comprises Structure G:

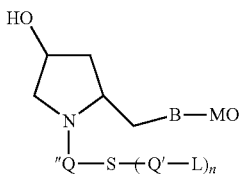

wherein:
B is selected from —O—, —S—, —N(R$^N$)—, —Z—P(Z')(Z")O—, —Z—P(Z')(Z")O—N$_m$—X—, and —Z—P(Z')(Z")O—N$_m$—Y—;

MO is a modified oligonucleotide;

R$^N$ is selected from H, methyl, ethyl, propyl, isopropyl, butyl, and benzyl;

Z, Z', and Z" are each independently selected from O and S;

each N of N$_m$ is, independently, a modified or unmodified nucleoside;

m is from 1 to 5;

X is selected from a phosphodiester linkage and a phosphorothioate linkage;

Y is a phosphodiester linkage;

each L is, independently, a ligand; n is from 1 to 10; S is a scaffold; and Q' and Q" are, independently, linking groups.

In some embodiments, each Q' and Q" are independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

A nonlimiting exemplary $L_n$-linker portion (e.g., of Structure F or G) of a compound is shown in Structure H below:

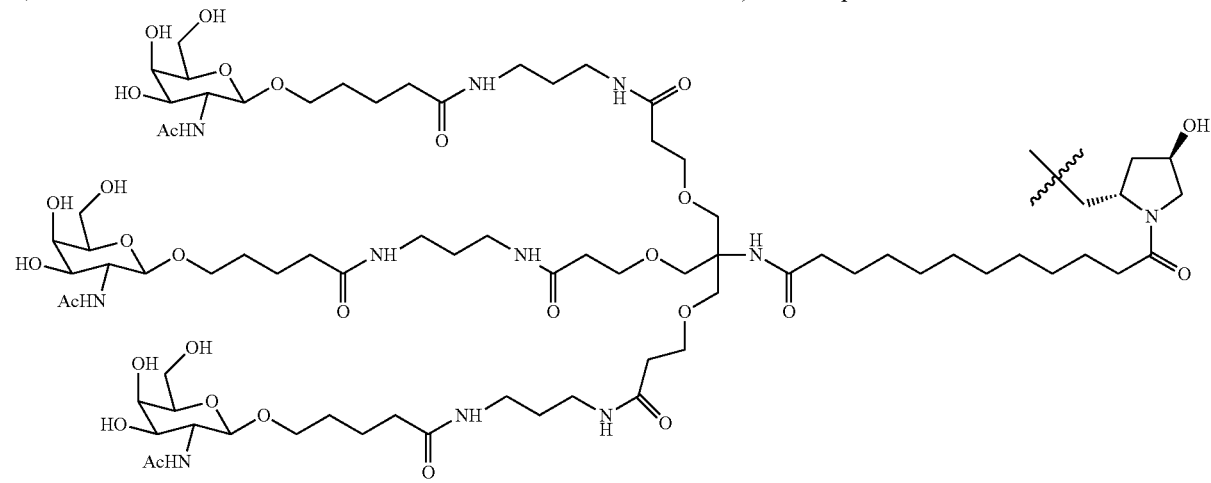

wherein the wavy line indicates attachment to the modified oligonucleotide (MO), to $X_1$, e.g. in Structure B, or to X or Y, e.g., in Structure C, or D.

Additional nonlimiting exemplary $L_n$-linker portion of a compound are illustrated in the structures below, wherein the wavy bond indicates attachment to the modified oligonucleotide (MO), e.g., in Structure A; to $X_1$, e.g. in Structure B; to X, e.g., in Structure C; or to Y, e.g., in Structure D.

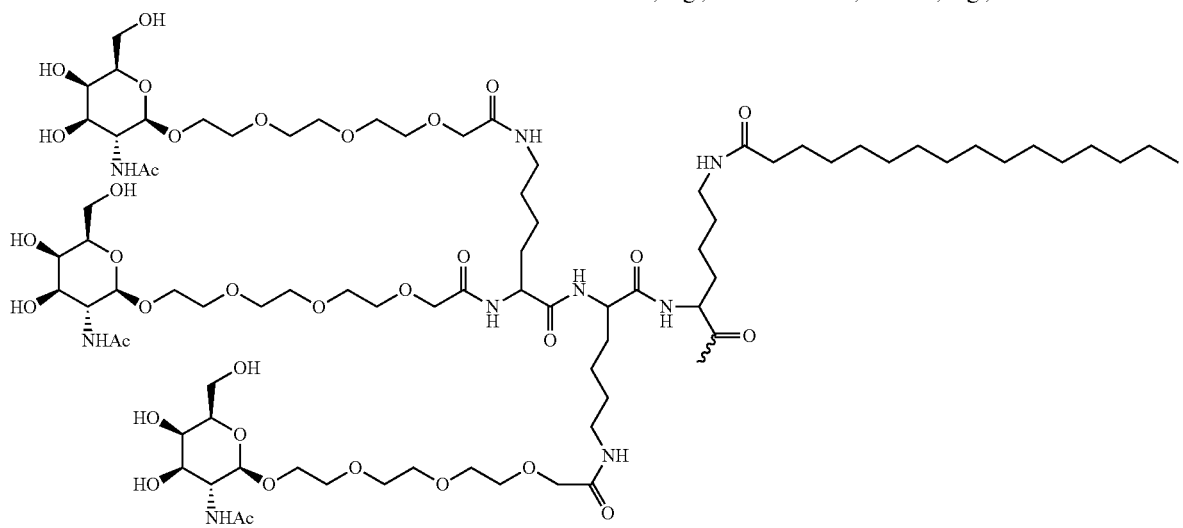

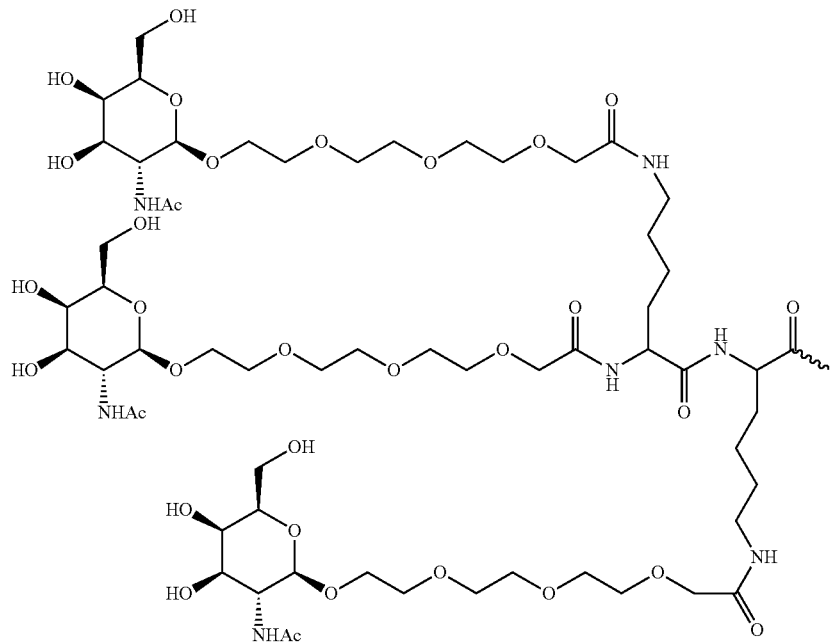
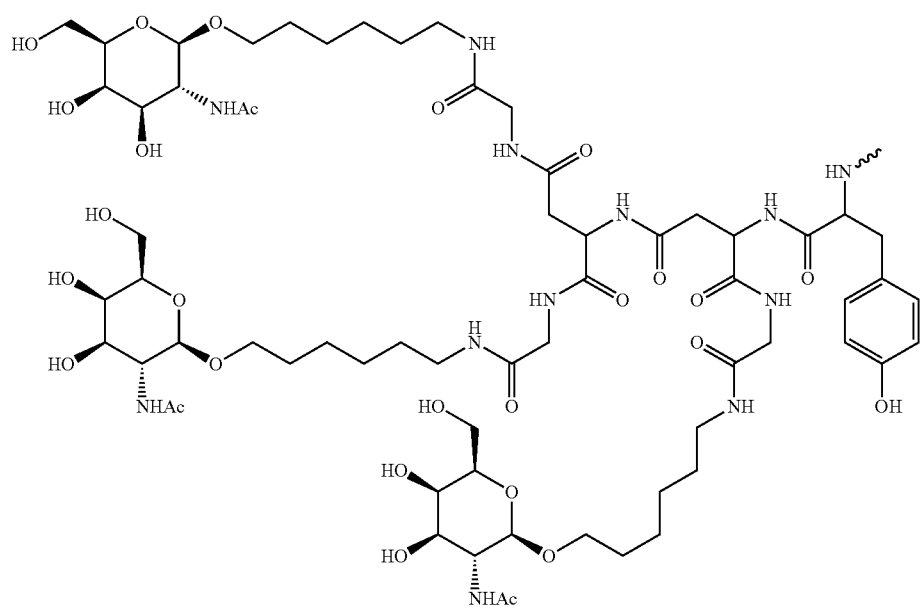

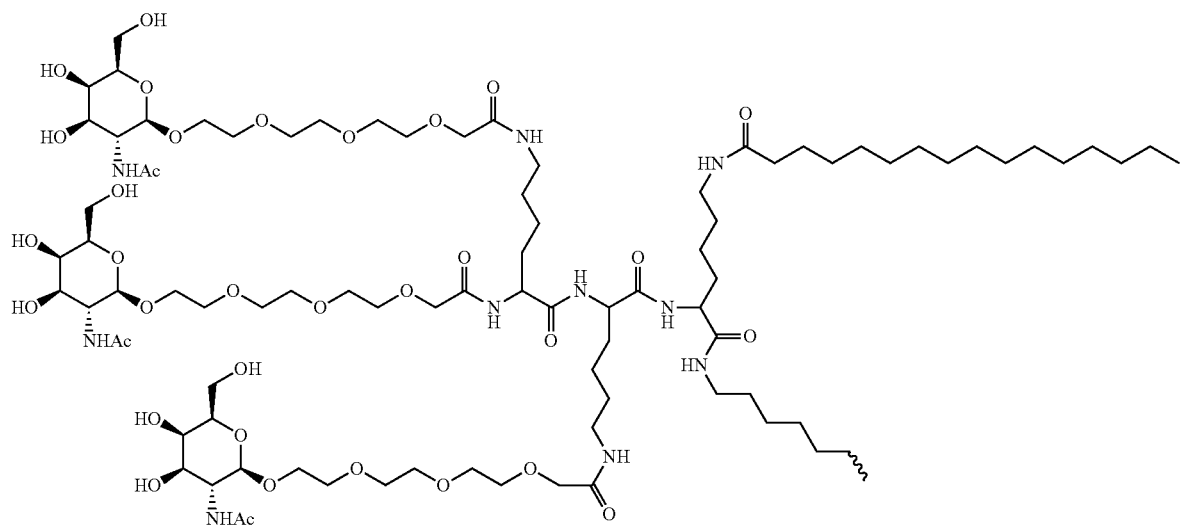
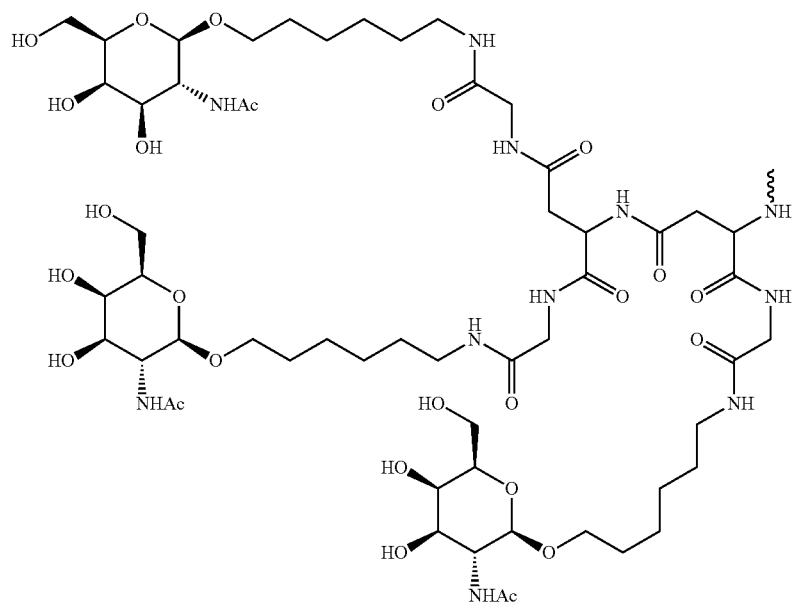

-continued
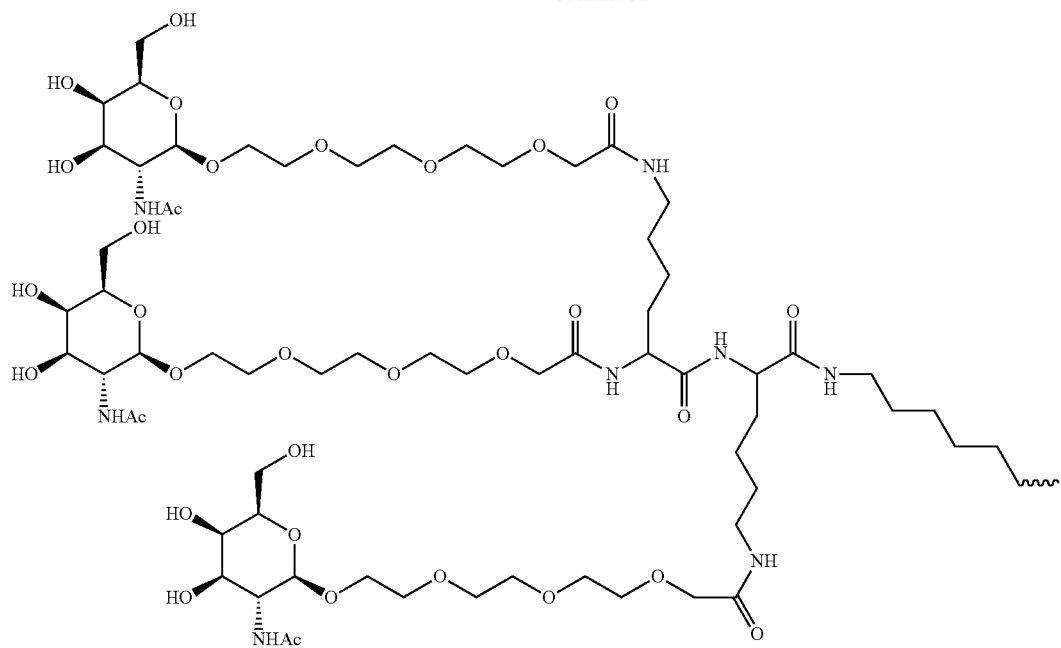
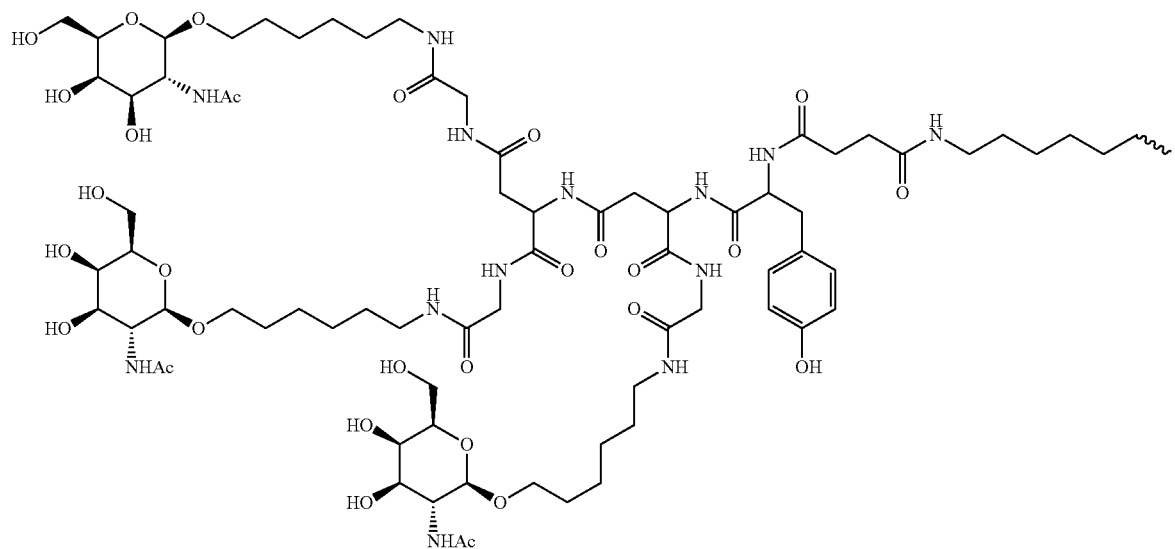

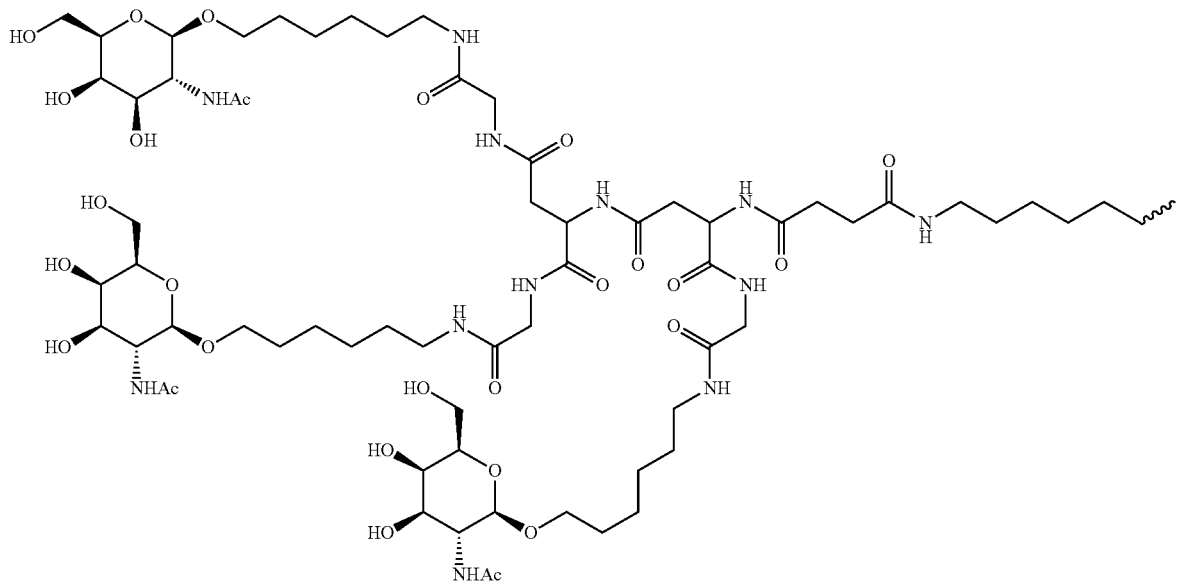

In certain embodiments, each ligand is a carbohydrate. A compound comprising a carbohydrate-conjugated modified oligonucleotide, when recognized by a cell surface lectin, is transported across the cell membrane into the cell. In certain embodiments, a cell surface lectin is a C-type lectin. In certain embodiments, the C-type lectin is present on a Kuppfer cell. In certain embodiments, a C-type lectin is present on a macrophage. In certain embodiments, a C-type lectin is present on an endothelial cell. In certain embodiments, a C-type lectin is present on a monocyte. In certain embodiments, a C-type lectin is present on a leukocyte. In certain embodiments, a C-type lectin is present on a dendritic cell. In certain embodiments, a C-type lectin is present on a B cell. A conjugate may facilitate uptake of an anti-miR-122 compound into any cell type that expresses a C-type lectin.

In certain embodiments, a C-type lectin is the asialoglycoprotein receptor (ASGPR). In certain embodiments, a conjugate comprises one or more ligands having affinity for the ASGPR, including but not limited to galactose or a galactose derivative. In certain embodiments, a ligand having affinity for the ASGPR is N-acetylgalactosamine, galactose, galactosamine, N-formylgalactosamine, N-propionyl-galactosamine, N-n-butanoylgalactosamine, or N-iso-butanoyl-galactosamine. Such conjugates facilitate the uptake of compounds into cells that express the ASGPR, for example, hepatocytes and dendritic cells.

In certain embodiments, a ligand is a carbohydrate selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-mannofuranose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, and N-acetylgalactosamine.

In certain embodiments, a ligand is selected from N-acetylgalactosamine, galactose, galactosamine, N-formylgalactosamine, N-propionyl-galactosamine, N-n-butanoylgalactosamine, and N-iso-butanoyl-galactosamine.

In certain embodiments, a ligand is N-acetylgalactosamine.

In certain embodiments, a compound comprises the structure:

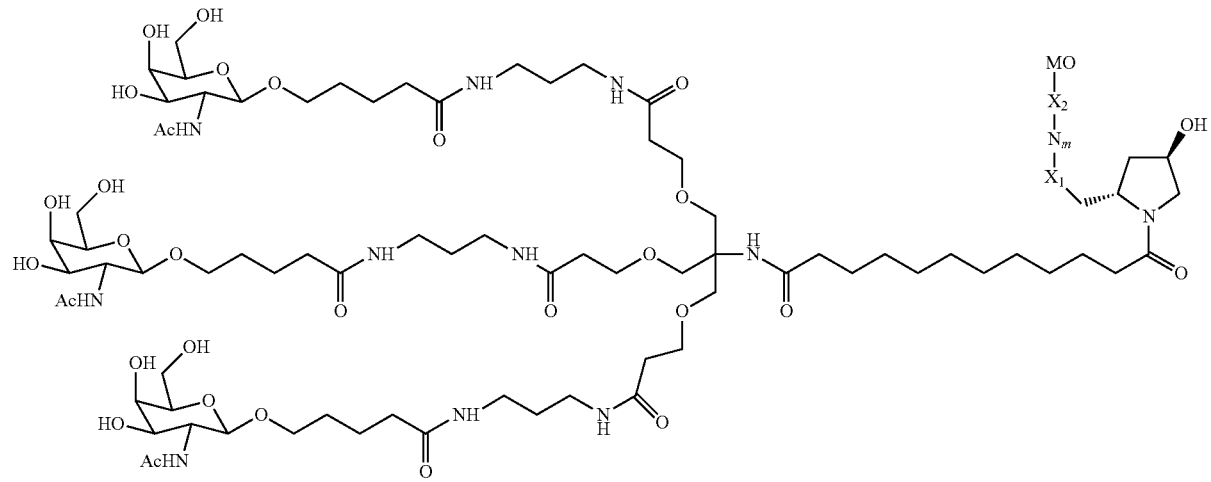 [SMILES: *C[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

(I)

wherein each N of $N_m$ is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprises the structure:

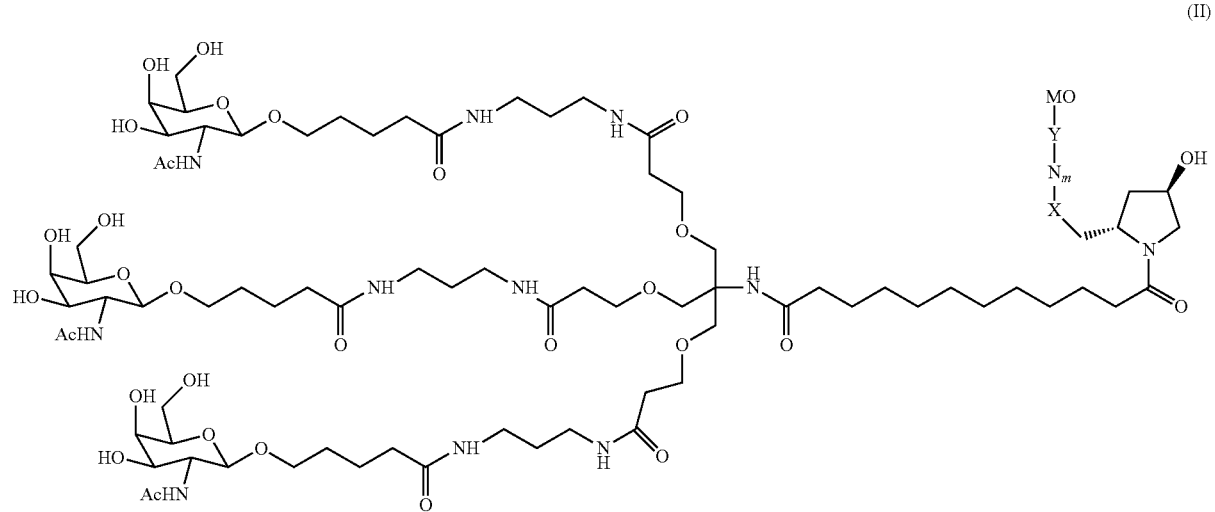

(II)

wherein X is a phosphodiester linkage or a phosphorothioate linkage; each N of $N_m$ is, independently, a modified or unmodified nucleoside and m is from 1 to 5; Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprises the structure:

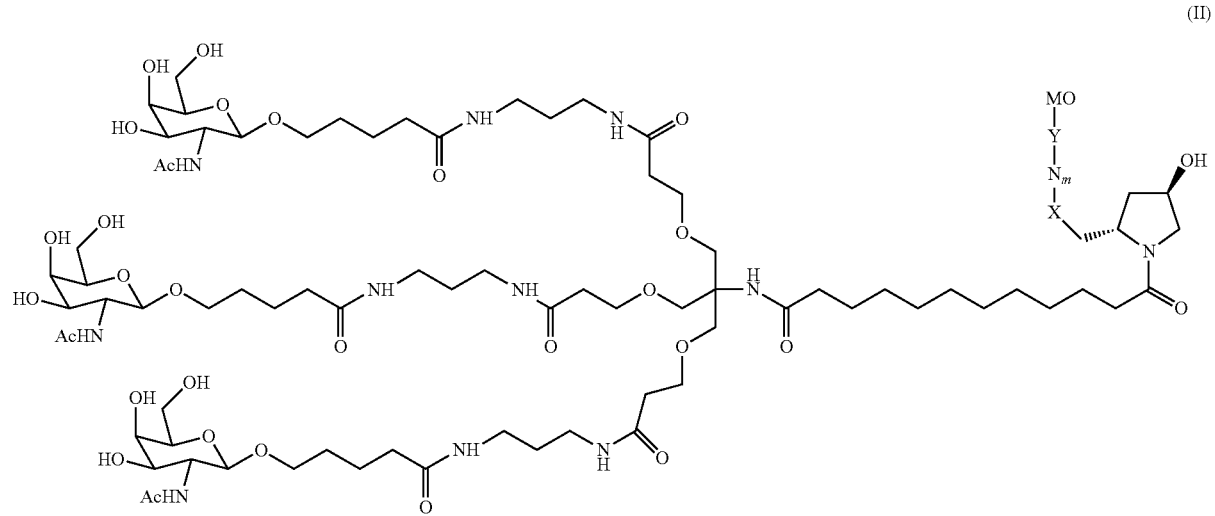

(II)

wherein X is a phosphodiester linkage; each N of $N_m$ is, independently, a modified or unmodified nucleoside and m is from 1 to 5; Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In some embodiments, a compound comprises the structure:

wherein X is a phosphodiester linkage; each N of $N_m$ is a deoxyadenosine (A); m is 2; Y is a phosphodiester linkage; and MO is 5'-$C_S A_S A_S U_S G_S C_S U_S G_S C_S A_S A_S C_S A_S A_S U_S G_S C_S U_S G_S C_S A_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages. In some embodiments, Y is linked to the 3' terminus of MO.

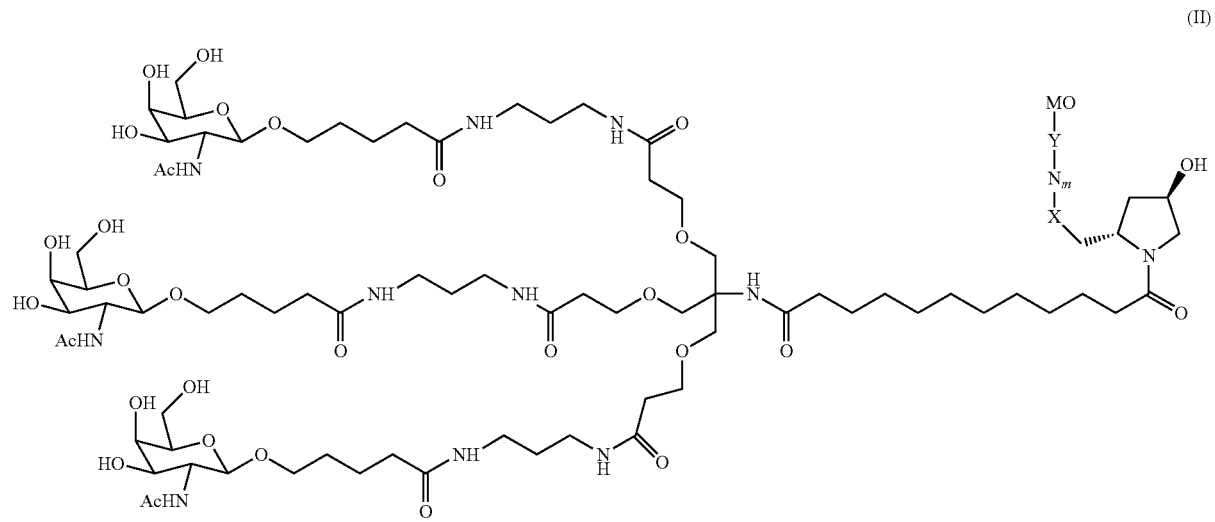

(II)

In some embodiments, a compound comprises the structure:

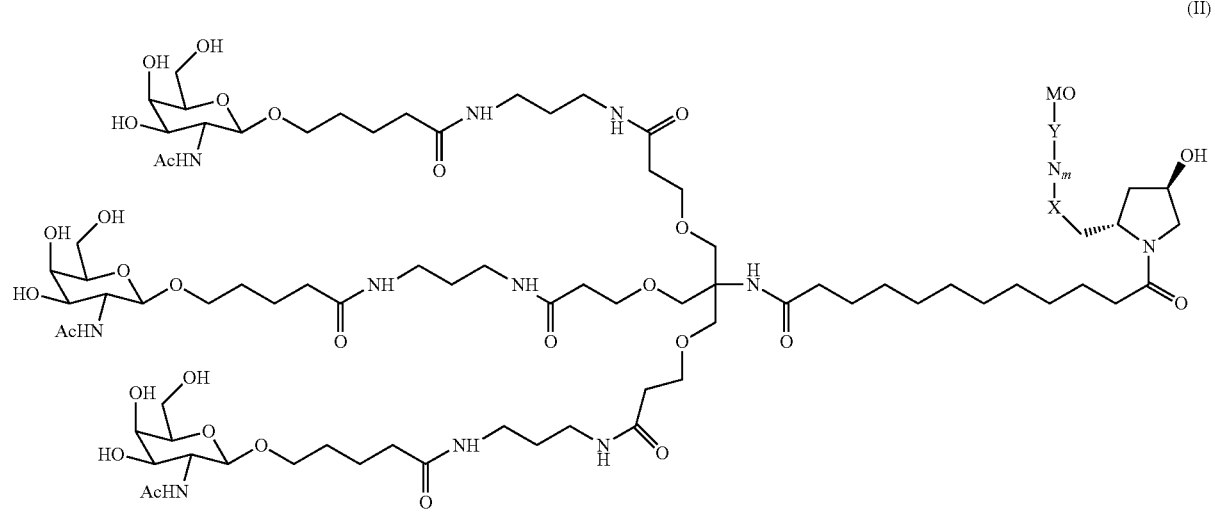

(II)

wherein X is a phosphodiester linkage; each N of $N_m$ is a deoxyadenosine (A); m is 2; Y is a phosphodiester linkage; and MO is 5'-$C_SA_SA_SU_SG_SC_SU_SG_SC_SA_SA_SC_SA_SA_SU_SG_S C_SU_SG_SC_SA_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages; and wherein Y is linked to the 3' terminus of MO.

In some embodiments, a compound consists of the structure:

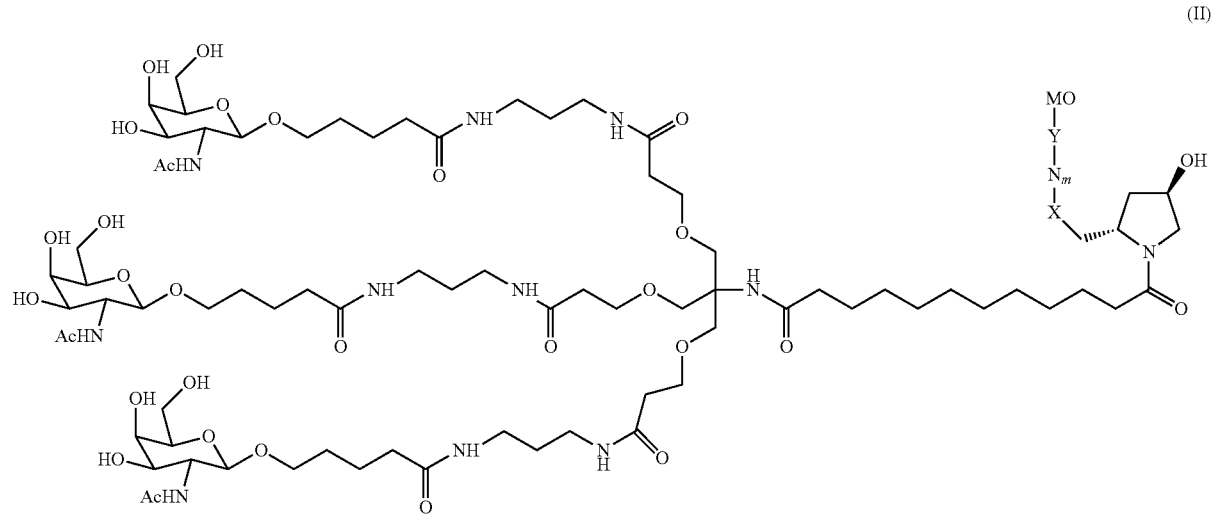

(II)

wherein X is a phosphodiester linkage; each N of $N_m$ is a deoxyadenosine (A); m is 2; Y is a phosphodiester linkage; and MO is 5'-$C_SA_SA_SU_SG_SC_SU_SG_SC_SA_SA_SC_SA_SA_SU_SG_S C_SU_SG_SC_SA_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages; and wherein Y is linked to the 3' terminus of MO; or a pharmaceutically acceptable salt thereof.

In some embodiments, a compound has the structure:

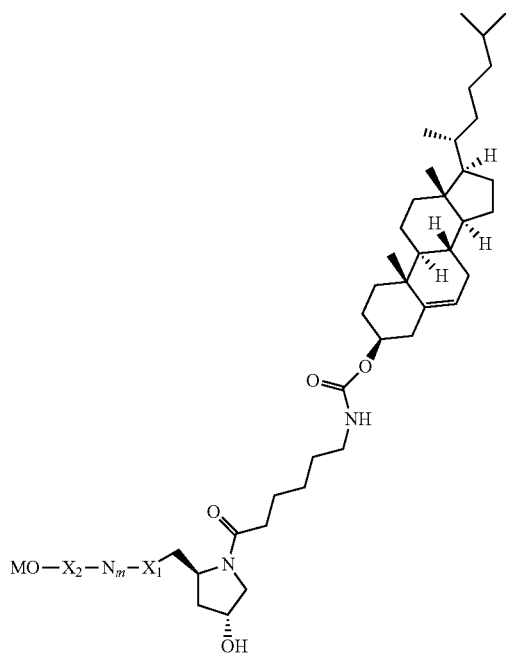

wherein each N of $N_m$ is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, at least one of $X_1$ and $X_2$ is a phosphodiester linkage. In certain embodiments, each of $X_1$ and $X_2$ is a phosphodiester linkage.

In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage. In certain embodiments, when m is 2, the nucleosides of $N_m$ are linked by a phosphodiester internucleoside linkage.

In any of the embodiments described herein, $N_m$ may be $N'_p N''$, where each N' is, independently, a modified or unmodified nucleoside and p is from 0 to 4; and N" is a nucleoside comprising an unmodified sugar moiety.

In certain embodiments, p is 0. In certain embodiments, p is 1, 2, 3, or 4. In certain embodiments, when p is 1, 2, 3, or 4, each N' comprises an unmodified sugar moiety.

In certain embodiments, an unmodified sugar moiety is a β-D-ribose or a β-D-deoxyribose.

In certain embodiments, where p is 1, 2, 3, or 4, N' comprises a purine nucleobase. In certain embodiments, N" comprises a purine nucleobase. In certain embodiments, a purine nucleobase is selected from adenine, guanine, hypoxanthine, xanthine, and 7-methylguanine. In certain embodiments, N is a β-D-deoxyriboadenosine or a β-D-deoxyriboguanosine. In certain embodiments, N" is a β-D-deoxyriboadenosine or a β-D-deoxyriboguanosine. In some embodiments, p is 1 and N' and N" are each a β-D-deoxyriboadenosine.

In certain embodiments, where p is 1, 2, 3, or 4, N' comprises a pyrimidine nucleobase. In certain embodiments, N" comprises a pyrimidine nucleobase. In certain embodiments, a pyrimidine nucleobase is selected from cytosine, 5-methylcytosine, thymine, uracil, and 5,6-dihydrouracil.

In any of the embodiments described herein, the sugar moiety of each N is independently selected from a β-D-ribose, a β-D-deoxyribose, a 2'-O-methoxy sugar, a 2'-O-methyl sugar, a 2'-fluoro sugar, and a bicyclic sugar moiety. In certain embodiments, each bicyclic sugar moiety is independently selected from a cEt sugar moiety, an LNA sugar moiety, and an ENA sugar moiety. In certain embodiments, the cEt sugar moiety is an S-cEt sugar moiety. In certain embodiments, the cEt sugar moiety is an R-cEt sugar moiety. In any embodiments described herein, the sugar moiety of each N may be independently selected from β-D-ribose, a β-D-deoxyribose, and a 2'-fluoro sugar.

In certain embodiments, a compound comprises the structure:

(II)

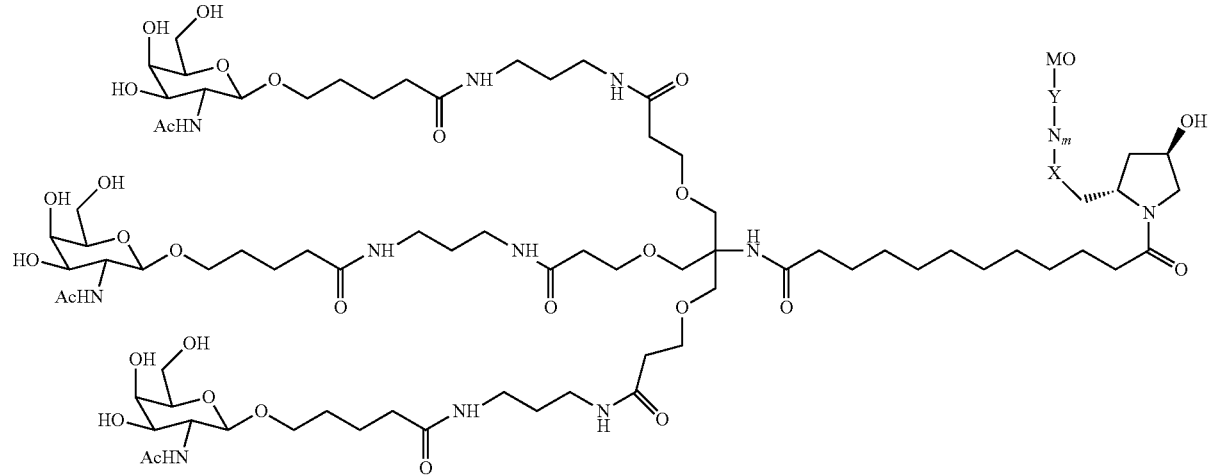

wherein X is a phosphodiester linkage; m is 1; N of $N_m$ is a β-D-deoxyriboadenosine; Y is a phosphodiester linkage; and MO is a modified oligonucleotide.

In certain embodiments, a compound comprises the structure:

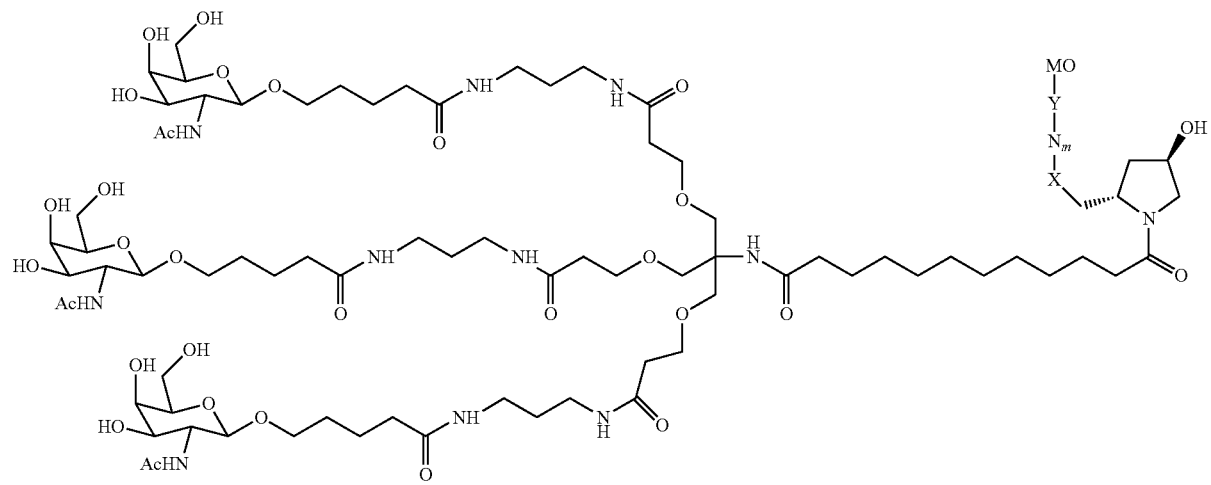

(II)

wherein X is a phosphodiester linkage; m is 2; each N of $N_m$ is a β-D-deoxyriboadenosine; the nucleosides of N are linked by a phosphodiester internucleoside linkage; Y is a phosphodiester linkage; and MO is a modified oligonucleotide.

Additional moieties for conjugation to a modified oligonucleotide include phenazine, phenanthridine, anthraquinone, acridine, fluoresceins, rhodamines, coumarins, and dyes. In certain embodiments, a conjugate group is attached directly to a modified oligonucleotide.

Certain Metabolic Products

Upon exposure to exonucleases and/or endonucleases in vitro or in vivo, compounds may undergo cleavage at various positions throughout the compound. The products of such cleavage may retain some degree of the activity of the parent compound, and as such are considered active metabolites. As such, a metabolic product of a compound may be used in the methods described herein. In certain embodiments, a modified oligonucleotide (unconjugated or conjugated) undergoes cleavage at the 5' end and/or the 3' end, resulting in a metabolic product that has 1, 2, or 3 fewer nucleotides at the 5' end and/or the 3' end, relative to the parent modified oligonucleotide. In certain embodiments, a modified oligonucleotide undergoes cleavage at the 5' end, releasing the 5'-terminal nucleotide and resulting in a metabolic product that has 1 less nucleotide at the 5' end, relative to the parent modified oligonucleotide. In certain embodiments, a modified oligonucleotide undergoes cleavage at the 5' end, releasing two 5'-terminal nucleosides and resulting in a metabolic product that has two fewer nucleotides at the 5' end, relative to the parent modified oligonucleotide. In certain embodiments, a modified oligonucleotide undergoes cleavage at the 3' end, releasing the 3'-terminal nucleotide and resulting in a metabolic product that has one less nucleotide at the 3' end, relative to the parent modified oligonucleotide. In certain embodiments, a modified oligonucleotide undergoes cleavage at the 3' end, releasing two 3'-terminal nucleosides and resulting in a metabolic product that has two fewer nucleotides at the 3' end, relative to the parent modified oligonucleotide.

In some embodiments, the modified oligonucleotides described herein undergo cleavage between the regions (i.e., oligo1, oligo2, and/or oligo3 in the structures described herein) such that the regions are separated from one another. For example, where a modified oligonucleotide has the structure [oligo 1]-[x-N]$_m$-x-[oligo2], in some embodiments, cleavage yields the oligo1 and oligo2, wherein one or both oligos may comprise one or more nucleotides of [x-N]$_m$, or one or both oligos may not comprise any nucleotides of [x-N]$_m$. Similarly, where a modified oligonucleotide has the structure [oligo 1]-[x-N]$_m$-x-[oligo2]-[x-N]$_m$-x-[oligo3], in some embodiments, cleavage yields the oligo1, oligo2, and oligo3, wherein one or more of the oligos may comprise one or more nucleotides of [x-N]$_m$, or one or more oligos may not comprise any nucleotides of [x-N]$_m$. In some embodiments, cleavage may be partial, and yield [oligo1]-[x-N]$_m$-x-[oligo2] and oligo3, or oligo1 and -[oligo2]-[x-N]$_m$-x-[oligo3], again where one or both portions may comprise one or more nucleotides of [x-N]$_m$. In some embodiments, the cleavage occurs in a target tissue. In some embodiments, each region of the modified oligonucleotide is more stable than the modified nucleotide as a whole.

Compounds comprising modified oligonucleotide linked to a conjugate moiety may also undergo cleavage at a site within the linker between the modified oligonucleotide and the ligand. In certain embodiments, cleavage yields the parent modified oligonucleotide comprising a portion of the conjugate moiety. In certain embodiments, cleavage yields the parent modified oligonucleotide comprising one or more subunits of the linker between the modified oligonucleotide and the ligand. For example, where a compound has the structure $L_n$-linker-$N_m$—P-MO, in some embodiments, cleavage yields the parent modified oligonucleotide comprising one or more nucleotides of $N_m$. In some embodiments, cleavage of a conjugated modified oligonucleotide yields the parent modified oligonucleotide. In some such embodiments, for example, where a compound has the structure $L_n$-linker-$N_m$—P-MO, in some embodiments, cleavage yields the parent modified oligonucleotide without any of the nucleotides of $N_m$.

Certain MicroRNA Targets

In certain embodiments, each nucleobase of a region of a modified oligonucleotide targeted to a microRNA is capable of undergoing base-pairing with a nucleobase at each corresponding position in the nucleobase sequence of the microRNA, or a precursor thereof. In certain embodiments the nucleobase sequence of a region of a modified oligonucleotide may have one or more mismatched basepairs with respect to its target microRNA or precursor sequence, and remains capable of hybridizing to its target sequence.

In certain embodiments, a region of a modified oligonucleotide has a nucleobase sequence that is complementary to the nucleobase sequence of a microRNA precursor, such as a microRNA stem-loop sequence. As a mature microRNA is contained within a microRNA precursor sequence, a region of a modified oligonucleotide having a nucleobase sequence complementary to a microRNA is also complementary to a region of a the corresponding microRNA precursor.

In certain embodiments, the number of linked nucleosides of a region of a modified oligonucleotide is less than the length of a microRNA, or a precursor thereof. In certain embodiments, the region of the modified oligonucleotide has a nucleobase sequence that is complementary to a region of the microRNA, or the precursor thereof. A region of a modified oligonucleotide having a number of linked nucleosides that is less than the length of the microRNA, wherein each nucleobase of a modified oligonucleotide is complementary to each nucleobase at a corresponding position in a microRNA nucleobase sequence, is considered to have a nucleobase sequence that is fully complementary to a region of a microRNA nucleobase sequence. For example, a region of a modified oligonucleotide consisting of 12 linked nucleosides, where the nucleobases of nucleosides 1 through 12 are each complementary to a corresponding position of a microRNA that is 23 nucleobases in length, is fully complementary to a 12 nucleobase region of the nucleobase sequence of the microRNA. Such a region of a modified oligonucleotide has a nucleobase sequence that is 100% complementarity to a 22 nucleobase portion of the microRNA. Further, such a region of a modified oligonucleotide is considered to be 100% complementary to the microRNA.

In certain embodiments, a region of the nucleobase sequence of a modified oligonucleotide is fully complementary to a region of the nucleobase sequence of a microRNA. In certain embodiments, 8 contiguous nucleobases of a modified oligonucleotide are each complementary to 8 contiguous nucleobases of a microRNA. In certain embodiments, 9 contiguous nucleobases of a modified oligonucleotide are each complementary to 9 contiguous nucleobases of a microRNA. In certain embodiments, 10 contiguous nucleobases of a modified oligonucleotide are each complementary to 10 contiguous nucleobases of a microRNA. In certain embodiments, 11 contiguous nucleobases of a modified oligonucleotide are each complementary to 11 contiguous nucleobases of a microRNA. In certain embodiments, 12 contiguous nucleobases of a modified oligonucleotide are each complementary to 12 contiguous nucleobases of a microRNA. In certain embodiments, 13 contiguous nucleobases of a modified oligonucleotide are each complementary to 13 contiguous nucleobases of a microRNA. In certain embodiments, 14 contiguous nucleobases of a modified oligonucleotide are each complementary to 14 contiguous nucleobases of a microRNA. In certain embodiments, 15 contiguous nucleobases of a modified oligonucleotide are each complementary to 15 contiguous nucleobases of a microRNA.

In certain embodiments, a region of a modified oligonucleotide comprises a nucleobase sequence that is complementary to a seed sequence, i.e. the region comprises a seed-match sequence. In certain embodiments, a seed sequence is a hexamer seed sequence. In certain embodiments, a hexamer seed sequence is nucleobases 1-6 of a microRNA. In certain embodiments, a hexamer seed sequence is nucleobases 2-7 of a microRNA. In certain embodiments, a hexamer seed sequence is nucleobases 3-8 of a microRNA. In certain embodiments, a seed sequence is a heptamer seed sequence. In certain embodiments, a heptamer seed sequence is nucleobases 1-7 of a microRNA. In certain embodiments, a heptamer seed sequence is nucleobases 2-8 of a microRNA. In certain embodiments, the seed sequence is an octamer seed sequence. In certain embodiments, an octamer seed sequence is nucleobases 1-8 of a microRNA. In certain embodiments, an octamer seed sequence is nucleobases 2-9 of a microRNA.

In certain embodiments, a nucleobase sequence of a region of a modified oligonucleotide is 100% complementary to a microRNA nucleobase sequence listed herein, or a precursor thereof. In certain embodiments, a region of a modified oligonucleotide has a nucleobase sequence having one mismatch with respect to the nucleobase sequence of a microRNA, or a precursor thereof. In certain embodiments, a region of a modified oligonucleotide has a nucleobase sequence having two mismatches with respect to the nucleobase sequence of a microRNA, or a precursor thereof. In certain embodiments, a region of a modified oligonucleotide has a nucleobase sequence having no more than two mismatches with respect to the nucleobase sequence of a microRNA, or a precursor thereof. In certain embodiments, the mismatched nucleobases are contiguous. In certain embodiments, the mismatched nucleobases are not contiguous.

Certain Nucleobase Sequences

Any nucleobase sequences set forth herein, including but not limited to those found in the Examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "ATmeCGAUCG," wherein $^{me}C$ indicates a cytosine base comprising a methyl group at the 5-position.

Certain Synthesis Methods

Modified oligonucleotides may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite triester with an oxidizing or sulfurizing agent), and capping (acetylation of unreacted 5'-hydroxyl groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exchange resin.

GalNAc-conjugated modified oligonucleotides may be made with automated solid phase synthesis, similar to the solid phase synthesis that produced unconjugated oligonucleotides. During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example in U.S. Pat. No. 8,106,022, which is herein incorporated by reference in its entirety for the description of the synthesis of carbohydrate-containing conjugates, including conjugates comprising one or more GalNAc moieties, and of the synthesis of conjugate covalently linked to solid support.

Provided herein are processes of making a GalNAc-conjugated modified oligonucleotide having the structure shown in formula (I):

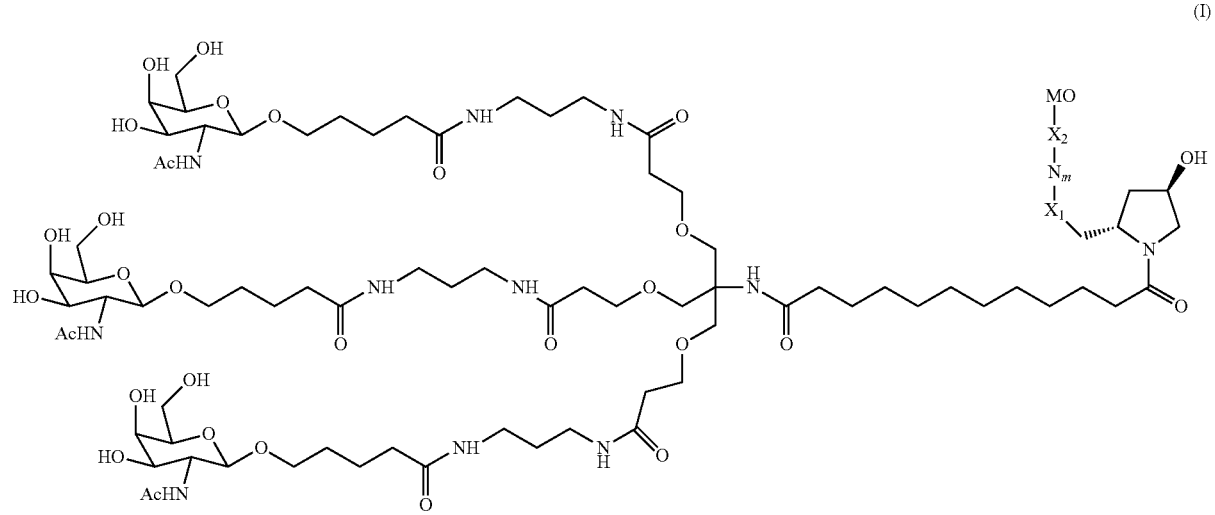

(I)

wherein each N of $N_m$ is, independently, a modified or unmodified nucleoside and m is from 1 to 5; $X_1$ and $X_2$ are each, independently, a phosphodiester linkage or a phosphorothioate linkage; and MO is a modified oligonucleotide; comprising the steps of:
providing a solid support comprising a conjugate as shown in formula IV;
deprotecting the DMT group under conditions effective to produce a reactive hydroxyl;

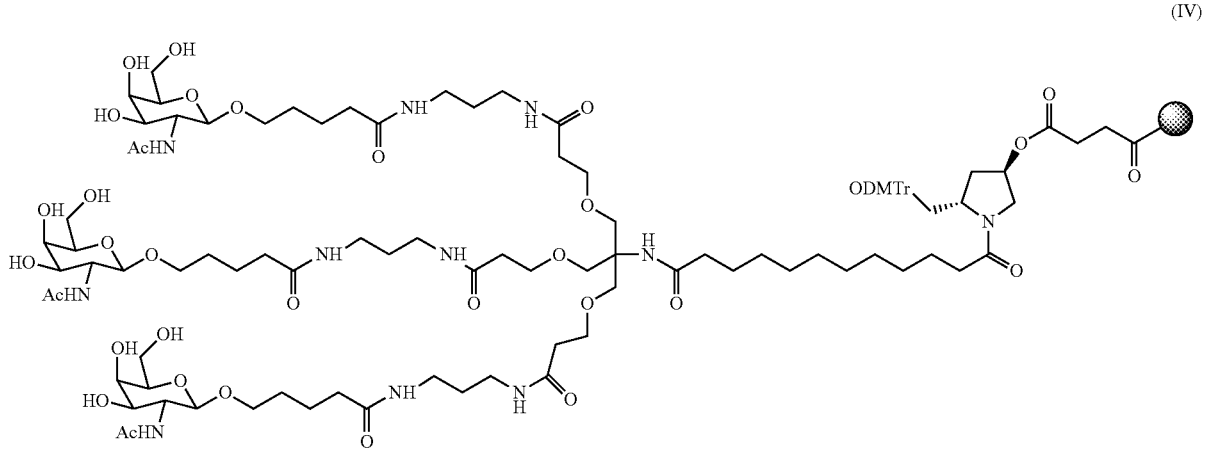

(IV)

performing sequential phosphoramidite coupling steps to form $N_m$;

performing sequential phosphoramidite coupling steps to form MO;

and releasing the conjugated modified oligonucleotide from the solid support.

Certain Modifications

Provided herein are compounds comprising modified oligonucleotides having the structure [oligo1]-[x-N]$_m$-x-[oligo2] or [oligo1]-[x-N]$_m$-x-[oligo2]-[x-N]$_m$-x-[oligo3]. Also provided herein are compounds comprising a modified oligonucleotide consisting of the structure [oligo 1]-[x-N]$_m$-x-[oligo2] or [oligo1]-[x-N]$_m$-x-[oligo2]-[x-N]$_m$-x-[oligo3]. In some embodiments, the modified oligonucleotide is attached to a conjugate moiety. A modified oligonucleotide may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain embodiments, a modified nucleoside is a stabilizing nucleoside. An example of a stabilizing nucleoside is a sugar-modified nucleoside.

In certain embodiments, a modified nucleoside comprises a modified sugar moiety. In certain embodiments, a modified nucleoside comprising a modified sugar moiety comprises an unmodified nucleobase. In certain embodiments, a modified sugar comprises a modified nucleobase. In certain embodiments, a modified nucleoside is a 2'-modified nucleoside.

In certain embodiments, a 2'-modified nucleoside comprises a bicyclic sugar moiety. In certain embodiments, the bicyclic sugar moiety is a D sugar in the alpha configuration. In certain embodiments, the bicyclic sugar moiety is a D sugar in the beta configuration. In certain embodiments, the bicyclic sugar moiety is an L sugar in the alpha configuration. In certain embodiments, the bicyclic sugar moiety is an L sugar in the beta configuration.

In certain embodiments, the bicyclic sugar moiety comprises a bridge group between the 2' and the 4'-carbon atoms. In certain embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2'; 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., J. Org. Chem., 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. In certain embodiments, bicyclic nucleosides include, but are not limited to, (A) α-L-Methyleneoxy (4'-CH$_2$—O-2') BNA; (B) β-D-Methyleneoxy (4'-CH$_2$—O-2') BNA; (C) Ethyleneoxy (4'-(CH$_2$)$_2$—O-2') BNA; (D) Aminooxy (4'-CH$_2$—O—N(R)-2') BNA; (E) Oxyamino (4'-CH$_2$—N(R)—O-2') BNA; (F) Methyl(methyleneoxy) (4'-CH(CH$_3$)—O-2') BNA (also referred to as constrained ethyl or cEt); (G) methylene-thio (4'-CH$_2$—S-2') BNA; (H) methylene-amino (4'-CH$_2$—N(R)-2') BNA; (I) methyl carbocyclic (4'-CH$_2$—CH(CH$_3$)-2') BNA; (J) c-MOE (4'-CH$_2$—OMe-2') BNA and (K) propylene carbocyclic (4'-(CH$_2$)$_3$-2') BNA as depicted below.

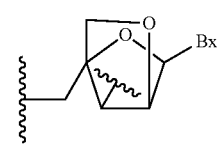

(A)

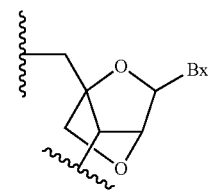

(B)

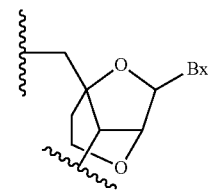

(C)

(D)
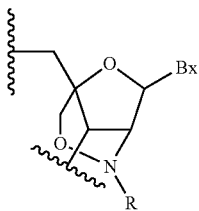

(E)
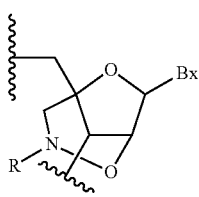

(F)
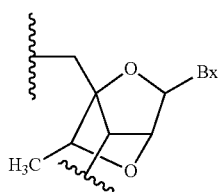

(G)
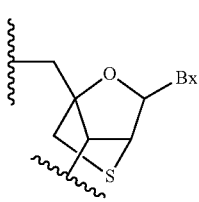

(H)
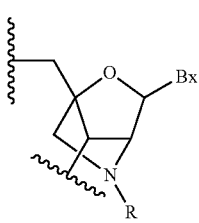

(I)
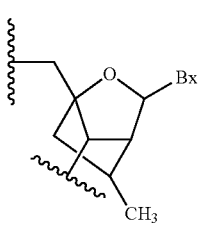

(J)
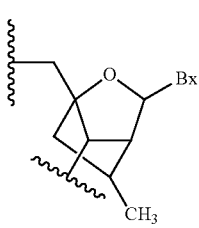

(K)
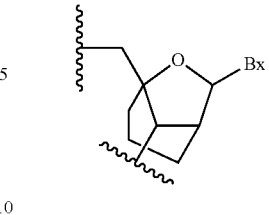

wherein Bx is a nucleobase moiety and R is, independently, H, a protecting group, or $C_1$-$C_{12}$ alkyl.

In certain embodiments, a 2'-modified nucleoside comprises a 2'-substituent group selected from halo, allyl, amino, azido, SH, CN, OCN, $CF_3$, $OCF_3$, O-, S-, or $N(R_m)$-alkyl; O-, S-, or $N(R_m)$-alkenyl; O-, S- or $N(R_m)$-alkynyl; O-alkylenyl-O-alkyl, alkynyl, alkaryl, aralkyl, O-alkaryl, O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, —$O(CH_2)_2O(CH_2)_2N(CH_3)_2$, and N-substituted acetamide (O-$CH_2$—C(=O)—$N(R_m)$$(R_n)$ where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'-$O(CH_2)_2SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a nucleoside comprising a modified sugar moiety is a 4'-thio modified nucleoside. In certain embodiments, a nucleoside comprising a modified sugar moiety is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—$(CH_2)_2$—$OCH_3$, and 2'-F.

In certain embodiments, a modified oligonucleotide (or a region of a modified oligonucleotide) comprises one or more internucleoside modifications. In certain embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a region of a modified oligonucleotide is a phosphorothioate internucleoside linkage.

In certain embodiments, a modified internucleoside linkage does not comprise a phosphorus atom. In certain embodiments, an internucleoside linkage is formed by a short chain alkyl internucleoside linkage. In certain embodiments, an internucleoside linkage is formed by a cycloalkyl internucleoside linkages. In certain embodiments, an internucleoside linkage is formed by a mixed heteroatom and alkyl internucleoside linkage. In certain embodiments, an internucleoside linkage is formed by a mixed heteroatom and cycloalkyl internucleoside linkages. In certain embodiments, an internucleoside linkage is formed by one or more short chain heteroatomic internucleoside linkages. In certain embodiments, an internucleoside linkage is formed by one or more heterocyclic internucleoside linkages. In certain embodiments, an internucleoside linkage has an amide backbone. In certain embodiments, an internucleoside linkage has mixed N, O, S and $CH_2$ component parts.

In certain embodiments, a modified oligonucleotide comprises one or more modified nucleobases.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and 0-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

In certain embodiments, a modified oligonucleotide comprises one or more stabilizing groups that are attached to one or both termini of an oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Pharmaceutical Compositions

Any of the compounds provided herein may be prepared as a pharmaceutical composition. In some embodiments, the pharmaceutical composition is prepared using a pharmaceutically acceptable salt of the compound. Nonlimiting exemplary pharmaceutically acceptable salts include sodium and potassium. In some embodiments, a pharmaceutical composition comprises a compound provided herein (including a pharmaceutically acceptable salt thereof) and a pharmaceutically acceptable carrier or diluent. Nonlimiting exemplary diluents include, for example, sterile water and sterile saline, such as phosphate-buffered saline (PBS). In some embodiments, a pharmaceutical composition comprises a pharmaceutically acceptable salt of a compound provided herein formulated in sterile water.

In certain embodiments, a pharmaceutical composition is administered in the form of a dosage unit (e.g., tablet, capsule, bolus, etc.). In some embodiments, a pharmaceutical composition comprises a compound provided herein at a dose within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. In certain embodiments, such pharmaceutical compositions comprise a compound provided herein present at a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose compound provided herein selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical composition comprising a compound provided herein is administered at a dose of 10 mg/kg or less, 9 mg/kg or less, 8 mg/kg or less, 7.5 mg/kg or less, 7 mg/kg or less, 6.5 mg/kg or less, 6 mg/kg or less, 5.5 mg/kg or less, 5 mg/kg or less, 4.5 mg/kg or less, 4 mg/kg or less, 3.5 mg/kg or less, 3 mg/kg or less, 2.5 mg/kg or less, 2 mg/kg or less, 1.5 mg/kg or less, 1 mg/kg or less, 0.75 mg/kg or less, 0.5 mg/kg or less, or 0.25 mg/kg or less.

In certain embodiments, a pharmaceutical agent is sterile lyophilized compound that is reconstituted with a suitable diluent, e.g., sterile water for injection or sterile saline for injection. The reconstituted product is administered as a subcutaneous injection or as an intravenous infusion after dilution into saline. The lyophilized drug product consists of a compound which has been prepared in water for injection, or in saline for injection, adjusted to pH 7.0-9.0 with acid or base during preparation, and then lyophilized. The lyophilized compound may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. Further, in some embodiments, the lyophilized compound is present in an amount that ranges from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, or 400 mg to 600 mg. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, a pharmaceutical composition provided herein comprises a compound in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprises a polyamine compound or a lipid moiety complexed with a nucleic acid. Such preparations are described in PCT publication WO/2008/042973, which is herein incorporated by reference in its entirety for the disclosure of lipid preparations. Certain additional preparations are described in Akinc et al., Nature Biotechnology 26, 561-569 (1 May 2008), which is herein incorporated by reference in its entirety for the disclosure of lipid preparations.

In certain embodiments, pharmaceutical compositions provided herein comprise one or more compounds and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more compounds provided herein to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a composition is provided comprising a compound as described herein, wherein the viscosity level is less than 60 cP. In certain embodiments, the composition has a viscosity level less than 50 cP. In certain embodiments, the composition has a viscosity level less than 40 cP. In certain embodiments, the composition has a viscosity level less than 30 cP. In certain embodiments, the composition has a viscosity level less than 20 cP. In certain embodiments, a viscosity level less than 20 cP allows for a compound concentration of about 200 mg/mL, which, in some embodiments, is suitable for subcutaneous injection.

In certain embodiments, one or more compounds provided herein is administered as a prodrug. In certain embodiments, upon in vivo administration, a prodrug is chemically or enzymatically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain embodiments, prodrugs possess superior transmittal across cell membranes. In certain embodiments, a prodrug facilitates delivery of a modified oligonucleotide to the desired cell type, tissue, or organ. In certain embodiments, a prodrug is a compound comprising a conjugated modified oligonucleotide. In certain instances, a prodrug may have improved solubility compared to the corresponding active form. In certain embodiments, prodrugs are less water soluble than the corresponding active form. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug, and/or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). In certain embodiments, a prodrug is a compound comprising a modified oligonucleotide is linked to a conjugated moiety in such a way as to allow for cleavage of the conjugate moiety and regeneration of the modified oligonucleotide upon in vivo administration. A compound comprising a modified oligonucleotide linked to a cleavable conjugate moiety, such as, for example, a compound of structure B, C, D, (I), or (II) described herein, may release the modified oligonucleotide in its unconjugated form, upon in vivo administration.

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administering to a subject comprises intraarterial, pulmonary, oral, rectal, transmucosal, intestinal, enteral, topical, transdermal, suppository, intrathecal, intraventricular, intraperitoneal, intranasal, intraocular, intramuscular, intramedullary, and intratumoral administration.

Certain Additional Therapies

Treatments for metabolic disorders may comprise more than one therapy. As such, in certain embodiments the present invention provides methods for treating metabolic disorders comprising administering to a subject in need thereof a compound comprising at least one region complementary to miR-103 and/or miR-107, or a precursor thereof, and further comprising administering at least one additional pharmaceutical agent.

In certain embodiments, the additional pharmaceutical agent is a glucose-lowering agent.

In certain embodiments, the glucose-lowering agent is a PPAR agonist (gamma, dual, or pan), a dipeptidyl peptidase (IV) inhibitor, a GLP-I analog (such as albiglutide (Eperzan®, GSK)), insulin or an insulin analog, an insulin secretagogue, a SGLT2 inhibitor, a human amylin analog, a biguanide, an alpha-glucosidase inhibitor, a meglitinide, a thiazolidinedione, or a sulfonylurea.

In certain embodiments, the glucose-lowering agent is a long-acting insulin, such as insulin glargine (Lantus®, Sanofi-Aventis) or insulin detemir (Levemir®, Novo Nordisk). In certain embodiments, an additional therapy comprises an insulin pump.

In certain embodiments, the glucose-lowering agent is a GLP-I analog. In certain embodiments, the GLP-I analog is exendin-4 or liraglutide.

In certain embodiments, the glucose-lowering agent is a sulfonylurea. In certain embodiments, the sulfonylurea is acetohexamide, chlorpropamide, tolbutamide, tolazamide, glimepiride, a glipizide, a glyburide, or a gliclazide.

In certain embodiments, the glucose-lowering agent is a biguanide. In certain embodiments, the biguanide is metformin. In certain embodiments, blood glucose levels are decreased without increased lactic acidosis as compared to the lactic acidosis observed after treatment with metformin alone.

In certain embodiments, the glucose-lowering agent is a meglitinide. In certain embodiments, the meglitinide is nateglinide or repaglinide.

In certain embodiments, the glucose-lowering agent is a thiazolidinedione. In certain embodiments, the thiazolidinedione is pioglitazone, rosiglitazone, or troglitazone. In certain embodiments, blood glucose levels are decreased without greater weight gain than observed with rosiglitazone treatment alone.

In certain embodiments, the glucose-lowering agent is an alpha-glucosidase inhibitor. In certain embodiments, the alpha-glucosidase inhibitor is acarbose or miglitol.

In certain embodiments, the glucose-lowering agent is an antisense oligonucleotide targeted to PTP1B. In certain embodiments, the glucose-lowering agent is an antisense oligonucleotide targeted to SGLT2.

In certain embodiments, an additional therapy is an anti-obesity agent. In certain embodiments, an anti-obesity agent is Orlistat, Sibutramine, or Rimonabant.

In a certain embodiment, the additional therapy is therapeutic lifestyle change. In certain embodiments, the therapeutic lifestyle change includes an exercise regimen and/or diet.

In certain embodiments the dose of an additional pharmaceutical agent is the same as the dose that would be administered if the additional pharmaceutical agent was administered alone.

In certain embodiments the dose of an additional pharmaceutical agent is lower than the dose that would be administered if the additional pharmaceutical agent was administered alone. In certain embodiments the dose of an additional pharmaceutical agent is greater than the dose that would be administered if the additional pharmaceutical agent was administered alone.

Further examples of additional pharmaceutical agents include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-I inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, an additional therapy is a lipid-lowering therapy. In certain such embodiments, a lipid-lowering therapy is therapeutic lifestyle change. In certain such embodiments, a lipid-lowering therapy is LDL apheresis.

Certain Kits

Any compound provided herein can be present in a kit. The kit can also contain instructions for using a compound provided herein. In some embodiments, a compound provided herein can be present within a vial. A plurality of vials, such as 10, can be present in, for example, dispensing packs. In some embodiments, the vial is manufactured so as to be accessible with a syringe.

In some embodiments, the kits may be used for administration a compound provided herein to a subject. In such instances, in addition to a compound provided herein, the kit can further comprise one or more of the following: syringe, alcohol swab, cotton ball, and/or gauze pad. In some embodiments, the compounds can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds.

Certain Experimental Models

In certain embodiments, the present invention provides methods of using and/or testing compounds of the present invention in an experimental model. Those having skill in the art are able to select and modify the protocols for such experimental models to evaluate a pharmaceutical agent of the invention.

Generally, compounds are first tested in cultured cells. Suitable cell types include those that are related to the cell type to which delivery of a compound is desired in vivo. For example, suitable cell types for the study of the methods described herein include primary hepatocytes, primary adipocytes, preadipocytes, differentiated adipocytes, HepG2 cells, Huh7 cells, Hep3b, SNU449, 3T3L1 cells, and C2C12 cells (murine myoblasts).

In certain embodiments, the extent to which a compound interferes with the activity of a miRNA is assessed in cultured cells. In certain embodiments, inhibition of miRNA activity may be assessed by measuring the levels of the miRNA. Alternatively, the level of a predicted or validated miRNA target may be measured. An inhibition of miRNA activity may result in the increase in the mRNA and/or protein of a miRNA target. Further, in certain embodiments, certain phenotypic outcomes may be measured. For example, suitable phenotypic outcomes include insulin signaling.

Suitable experimental animal models for the testing of the methods described herein include: ob/ob mice (a model for diabetes, obesity and insulin resistance), db/db mice (a model for diabetes, obesity and insulin resistance), high-fat fed C57B16/J mice, KKay mice, NZO-based mouse models, chemically-induced diabetic mouse models, Zucker diabetic rats, and aP2-SREBP transgenic mice.

Certain Quantitation Assays

The effects of a compound on the activity of its target RNA(s) may be assessed by a variety of methods known in the art. In certain embodiments, these methods are be used to quantitate microRNA levels in cells or tissues in vitro or in vivo.

In certain embodiments, changes in target levels and/or activity are measured by microarray analysis. In certain embodiments, changes in target levels and/or activity are measured by one of several commercially available PCR assays, such as the TaqMan® MicroRNA Assay (Applied Biosystems).

In vitro activity of anti-miR compounds may be assessed using a luciferase cell culture assay. In this assay, a microRNA luciferase sensor construct is engineered to contain one or more binding sites of the microRNA of interest, and a luciferase gene. When the microRNA binds to its cognate site in the luciferase sensor construct, luciferase expression is suppressed. When the appropriate anti-miR is introduced into the cells, it binds to the target microRNA and relieves suppression of luciferase expression. Thus, in this assay anti-miRs that are effective inhibitors of the anti-miR of interest will cause an increase in luciferase expression.

Activity of anti-miR compounds may be assessed by measuring the mRNA and/or protein level of a target of a microRNA. A microRNA binds to its cognate site within one or more target RNAs, leading to suppression of a target RNA, thus inhibition of the microRNA results in the increase in the level of mRNA and/or protein of a target of the microRNA (i.e., derepression). The derepression of one or more target RNAs may be measured in vivo or in vitro.

EXAMPLES

The following examples are presented in order to more fully illustrate some embodiments of the invention. They should, in no way be construed, however, as limiting the broad scope of the invention.

Those of ordinary skill in the art will readily adopt the underlying principles of this discovery to design various compounds without departing from the spirit of the current invention.

Where provided, statistical significance is defined as follows: **=p value of <0.0001; *=p value of 0.0001 to 0.001; **=p value of 0.001 to 0.01; *=p value of 0.01 to 0.05.

Throughout the examples, unless otherwise indicated, dosages or concentrations of conjugated compounds refer to the amount of the entire compound, and not a portion thereof. For example, a 5 mg/kg dose means 5 mg of the conjugated modified oligonucleotide, per kg body weight.

Example 1

Anti-miR-103/107 Compound Screening

Previous studies have tested a cholesterol-conjugated, 2'-OMe modified anti-miR-103/107 compound in mouse models of impaired insulin sensitivity and glucose tolerance. While efficacy was observed following treatment with this compound, the required dose to achieve efficacy was high, and also required intravenous administration, which is potentially inconvenient for the treatment of a chronic disease such as diabetes. Additional studies have tested a 2'-MOE/2'-fluoro modified anti-miR-103/107 compound, however compounds comprising 2'-fluoro modifications may cause immune stimulation when administered to animals. In view of the need for a therapeutic agent to be efficacious, convenient to administer, and safe, a screen was performed for anti-miR-103/107 compounds that are candidate therapeutic agents. A number of properties were evaluated, including efficacy in models of insulin resistance and diabetes, cross-reactivity with microRNAs of related sequence, stimulation of inflammation, viscosity, and pharmacokinetic profile.

Hundreds of compounds were designed, having varying lengths and chemical composition. The compounds are tested in a number of assays, to evaluate in vitro inhibitory activity, in vitro cell viability, metabolic stability (i.e. resistance to endonucleoase activity in a liver lysate), in vivo immunostimulatory activity (as measured by in vivo induction of IFIT and/or OASL), viscosity, efficacy in relevant disease models, safety, and pharmacokinetics. Of the hundreds of compounds that were designed, only a few compounds met the selection criteria for all properties evaluated.

Example 2

Cross-Reactivity of Anti-miR-103 Compounds within miR-15 Family

One criteria for selecting a potential therapeutic candidate was a lack of cross-reactivity with microRNAs having similar nucleobase sequence. Nucleobases 1-6 of miR-103 and miR-107 are identical to nucleobases 2-7 of members of the miR-15 family, which includes miR-15a, miR-15b, miR-16, miR-195, miR-497, miR-503, miR-424, and miR-646 (see Table below). Although there is little sequence similarity outside the seed region, due to the importance of targeting the seed region, the ability of anti-miR-103/107 compounds to also inhibit a miR-15 family member was evaluated, to ensure that anti-miR-103/107 compounds would not also inhibit a miR-15 family member. Because miR-15 family members are proposed to act as tumor suppressors, it is preferable to avoid inadvertent inhibition of a miR-15 family member.

TABLE A

| miR/anti-miR | Sequence | SEQ ID NO |
|---|---|---|
| miR-16 (3' to 5') | 3'-GCGGUUAUAAAUGCACGACGAU-5' | 14 |
| miR-103 (3' to 5') | 3'-AGUAUCGGGACAUGUUACGACGA-5' | 1 |
| anti-miR-103/107 (5' to 3') U at 3' end | 5'-ATAGCCCTGTACAATGCTGCU-3' | 20 |
| anti-miR-103/107 (5' to 3') A at 3' end | 5'-ATAGCCCTGTACAATGCTGCA-3' | 21 |
| Anti-miR-103/107 (5' to 3') C at 3' end | 5'-ATAGCCCTGTACAATGCTGCC-3' | 22 |

When the nucleobase at this position was changed from a U to an A, it was observed that the anti-miR no longer hybridized to miR-16. This mismatch did not significantly affect the ability of the compound to inhibit the activity of miR-103/107. Thus, an anti-miR nucleobase sequence was identified that inhibited miR-103/107, with minimal to no cross-reactivity with a miR-15 family member. The elimination of cross-reactivity was observed for a number of anti-miR-103/107 compounds of varying lengths and nucleoside sugar composition (cEt, 2'-MOE, 2'-OMe, and DNA), suggesting that the effect of the nucleobase change is independent of the chemical modifications in the anti-miR. An exception was observed with 2'-F/2'-MOE modified compounds, which retained cross-reactivity despite having a mismatch at the 3' terminus of the compound.

```
                    *           #
hsa-miR-107         A G C A G C A U U G U A C A G G G C U A U C A    SEQ ID NO: 2
hsa-miR-103         A G C A G C A U U G U A C A G G G C U A U G A    SEQ ID NO: 1
hsa-miR-15a    U    A G C A G C A C A U A A U G G U U U G U G        SEQ ID NO: 12
hsa-miR-15b    U    A G C A G C A C A U C A U G G U U U A C A        SEQ ID NO: 13
hsa-miR-16     U    A G C A G C A C G U A A A U A U U G G C G        SEQ ID NO: 14
hsa-miR-195    U    A G C A G C A C A G A A A U A U U G G C C        SEQ ID NO: 15
hsa-miR-497    C    A G C A G C A C A C U G U G G U U U G U          SEQ ID NO: 16
hsa-miR-503    U    A G C A G C G G G A A C A G U U C U G C A G      SEQ ID NO: 17
hsa-miR-424    C    A G C A G C A A U U C A U G U U U U G A A        SEQ ID NO: 18
hsa-miR-646    A    A G C A G C U G C C U C U G A G G C              SEQ ID NO: 19
```

Compounds were tested for the ability to inhibit miR-16 in a luciferase assay, and/or to hybridize to miR-16 (via a biochemical assay that measures the ability of an anti-miR to associate with the target miR in the Ago complex). miR-16 was selected a representative member of the miR-15 family.

Through testing the ability of the compounds to hybridize to miR-16, it was observed that compounds with complete complementarity to nucleotides 1-6 of miR-107 and miR-103 were able to hybridize to miR-16. Changes to the anti-miR-103/107 sequence were tested to determine whether introduction of a mismatch at the position complementary to position 1 of miR-103/107 (which corresponds to position 2 of miR-16 and its related family members) could reduce binding to miR-16. The relevant nucleobase positions are underscored in Table A below.

Similarly, when the nucleobase at the 3' terminus was changed from a U to a C, it was observed that the anti-miR no longer hybridized to miR-16, yet the mismatch did not significantly impact the ability of the compound to inhibit the activity of miR-103/107. Thus, the elimination of cross-reactivity, with simultaneous retention of potency, was observed for multiple nucleobase changes at the position opposite the 5' terminal position of miR-103/107.

Example 3

Efficacy in Models of Insulin Resistance

To determine the effects of anti-miR-103/107 compounds on glucose and insulin levels, compounds are administered to high-fat fed obese mice (also called diet-induced obese mice or DIO mice), a model of impaired glucose tolerance and type 2 diabetes. Studies are conducted according to standard protocols for this model, as described below.

General Protocol for DIO Model

Mice on a high fat (60% of Kcal from fat—Research Diet RD12492) are randomized into treatment groups based on similar baseline bodyweight, blood glucose and insulin. The animals are then dosed once weekly via subcutaneous injection near the subscapular region with a volume of 4 mL/kg. Bodyweight is measured and monitored weekly.

Fasting blood glucose and fasting plasma insulin are measured weekly after a 4 to 6 hour fast. For example, for the first blood collection, 2 or 3 days after the second dose (week 1), the animals are fasted for 4 hours and blood glucose is measured via tail nick using a hand held glucometer (GE100). Final blood collection for glucose and insulin is 2 to 4 days after the final dose. In some studies, during week 3, an oral glucose tolerance test (OGTT) is performed. An oral glucose tolerance test (OGTT) determines how quickly glucose is cleared from the blood after glucose administration. After a 4 hour fast, blood is taken for measurements of fasting glucose and insulin. Next, 2 g/kg of dextrose is administered to each animal. 30 minutes after the oral dose of dextrose, blood is taken again for measurements of glucose and insulin. After four weeks of dosing (total of 5 doses), animals are sacrificed 72 to 96 hours after the last dose. Alternatively, animals may be dosed for a total of 6 or 7 doses.

Liver, kidney and adipose (epidydmal and subcutaneous depots) are collected for PK analysis.

Liver and adipose (epidydmal, subcutaneous and brown fat) are collected for target gene expression.

Liver is also collected for triglyceride levels. Blood is collected for serum analysis.

An insulin resistance score (HOMA-IR) can be calculated according to the following formula: fasting plasma glucose (mg/dl) times fasting serum insulin (ng/ml) divided by 16.34. Low HOMA-IR values indicate high insulin sensitivity, whereas high HOMA-IR values indicate low insulin sensitivity (insulin resistance).

Insulin sensitivity may be evaluated using a hyperinsulinemic euglycemic clamp assay. In this assay, catheterized mice receive an infusion of glucose and insulin. The insulin is infused at a constant high level (hyperinsulinemic), while the glucose is infused at a variable rate to maintain blood glucose at a constant, normal (euglycemic) level. The rate of glucose infusion indicates the sensitivity to insulin, e.g. an increased glucose infusion rate indicates an increased sensitivity to insulin. For a DIO mouse, fed a high fat diet for 20 weeks, a typical infusion rate is 5-10 mg/kg/min. For a normal mouse, fed a normal diet for 24 weeks, a typical infusion rate is 30-40 mg/kg/min.

Anti-miR-103/107 Compound Screening in DIO Model

A 2'-F/2'-MOE modified compound (compound 97243, below) had previously demonstrated efficacy in a mouse model of insulin resistance and diabetes, however this compound induces expression of the IFIT gene in an in vivo assay, and hybridizes to the miR-16 sequence, making the compound unsuitable as a potential therapeutic agent. However, due to its efficacy, this compound in the mouse models of insulin resistance was used as a benchmark for in vivo screening of compounds that were at least as efficacious, yet did not cause immune stimulation and are not cross-reactive with the miR-15 family.

Compound 97243 has the structure: $T_E G_E A_F U_F A_F G_F C_F C_F C_F U_F G_F U_F A_E {}^m C_E A_E A_F U_F G_F C_F U_F G_F {}^m C_E T_E$ (SEQ ID NO: 23) where subscript "F" E indicates a 2'-fluoro nucleoside, subscript "E" indicates a 2'-O-methoxyethyl nucleoside, all linkages are phosphorothioate and subscript "m" indicates 5-methylcytosine.

Compound 12743 (structure in Table B below) was designed, synthesized and tested in the in vitro luciferase and IFIT assays. As the compound performed well in these assays, it was further tested for efficacy. In this study, DIO mice (fed a high fat diet for ~15 weeks) were sorted into treatment groups based on body weight, fasting insulin and fasting glucose. Treatments were administered subcutaneously, once every 6 to 7 days, for a total of 5 treatments. On day 8 of the study, and once weekly thereafter, blood was collected after a 4 hour fast to measure glucose or insulin. Compound 12743 improved insulin sensitivity, as determined by HOMA-IR calculations in the DIO (for example, FIG. 3, 2 week data for compound 12743; FIG. 4, 3 week data for compound 12743) and db/db models, and as determined by hyperinsulinemic euglycemic clamp in the DIO model. Liver triyglycerides were also lowered following treatment with compound 12743.

Analysis of the expression levels of direct target genes of miR-103/107 following inhibition with compound 12743 revealed compound-mediated activity in both adipose and liver tissue. To identify compounds with further improved efficacy, and enhance delivery of anti-miR to the liver, GalNAc-conjugated anti-miR compounds were synthesized and tested. Conjugated anti-miR-103/107 compound was formed by conjugating a structure in FIG. 2 to the 3' end of the modified oligonucleotide. Compound structures are shown in the Table below, where subscript subscript "E" indicates a 2'-O-methoxyethyl nucleoside, subscript "S" indicates an S-cEt nucleoside, all linkages are phosphorothioate and subscript "m" indicates 5-methylcytosine.

TABLE B

Anti-miR-103/107 Compounds

Figure 1:
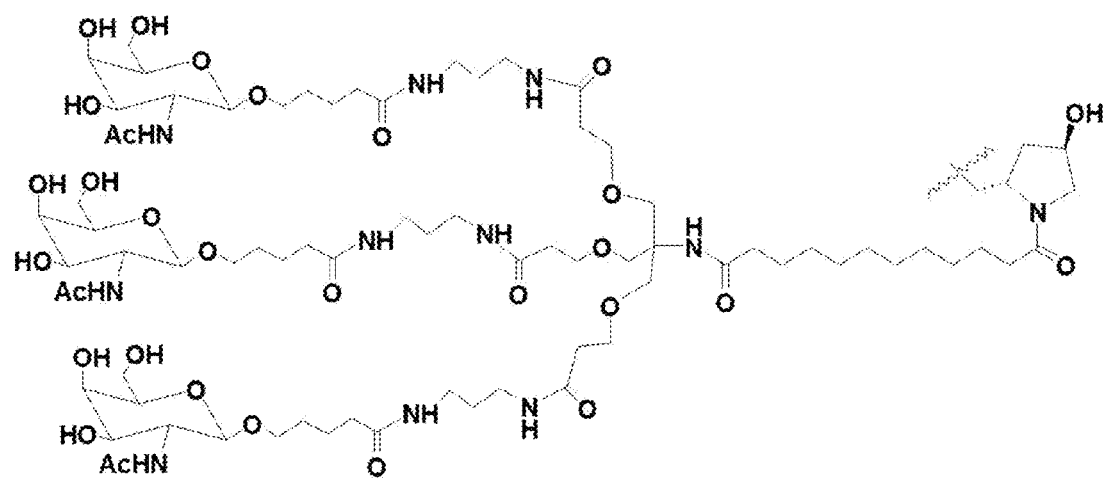
FIG. 1. Structure of conjugate moiety comprising three GalNAc ligands.
Figure 2A:
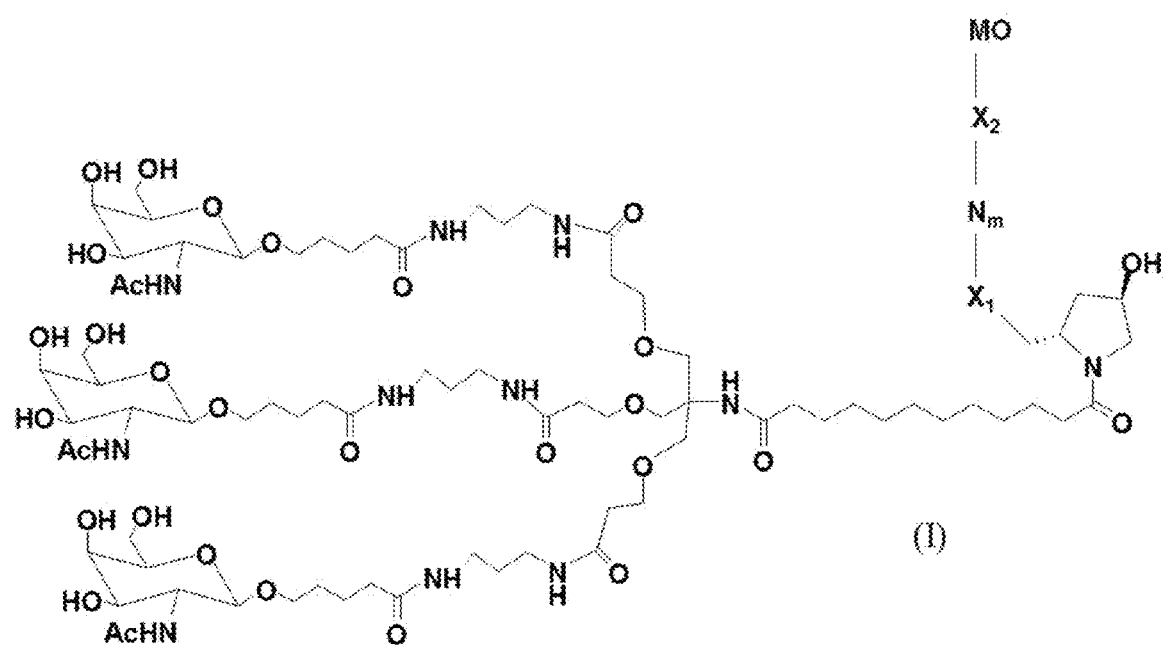
FIG. 2A-C. Conjugated modified oligonucleotide structures.
Figure 2B:
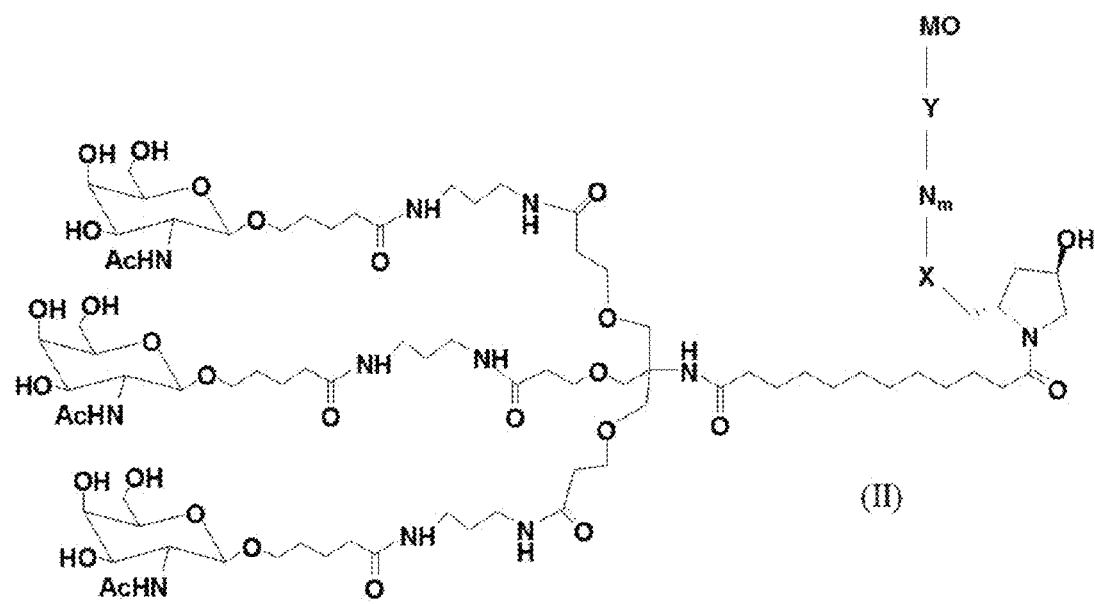
Figure 2C:
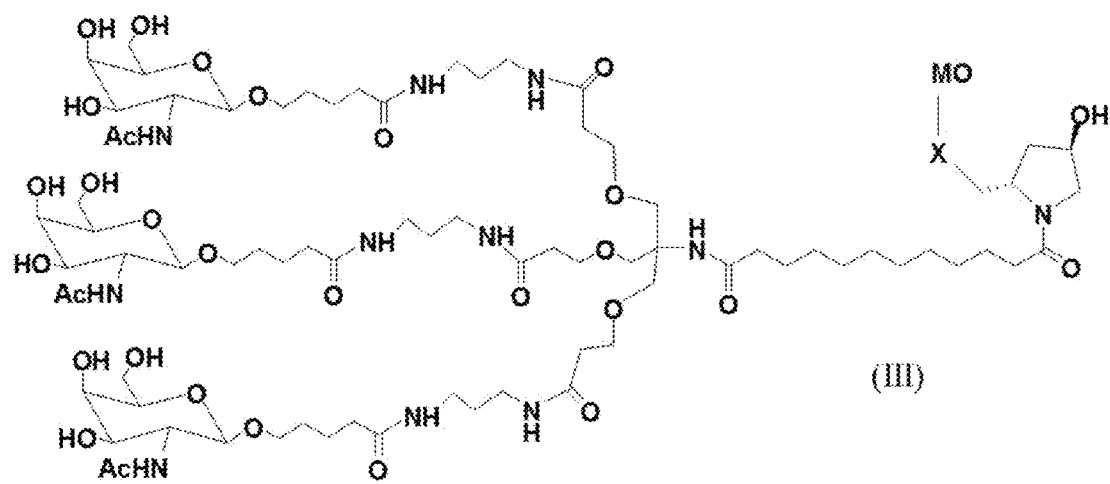

| Compound | Sequence and Chemistry (Modified Oligonucleotide or MO) | Structure |
|---|---|---|
| 12743 | $A_E T_E A_E G_E {}^m C_E {}^m C_E {}^m C_E T_E G_E T_E A_E {}^m C_E A_S ATG_S CTG_S C_S U_S$ (SEQ ID NO: 20) | Unconjugated |
| 19743 | $A_E T_E A_E G_E {}^m C_E {}^m C_E {}^m C_E T_E G_E T_E A_E {}^m C_E A_S ATG_S CTG_S C_S U_S$ (SEQ ID NO: 20) | Structure I of FIG. 2A, where $X_2$ is a phophodiester linkage, m is 1, $N_m$ is a β-D-deoxynucleoside (dA), $X_1$ is a phosphodiester linkage |

TABLE B-continued

Anti-miR-103/107 Compounds

| Compound | Sequence and Chemistry (Modified Oligonucleotide or MO) | Structure |
|---|---|---|
| 19843 | $A_E T_E A_E G_E{}^m C_E{}^m C_E{}^m C_E T_E G_E T_E A_E{}^m C_E A_S ATG_S CTG_S C_S U_S$ (SEQ ID NO: 20) | Structure I of FIG. 2A, where $X_2$ is a phophodiester linkage, m is 2, $N_m$ is a β-D-deoxynucleoside (dA), $X_1$ is a phosphodiester linkage |

The conjugated compounds were tested for the ability of the anti-miR to be released from the conjugate structure. Compound was administered to DIO mice, and metabolites in liver tissue were measured. Compound 19843 was efficiently metabolized to the unconjugated anti-miR. In contrast, compound 19743 was not efficiently metabolized to the unconjugated anti-miR, suggesting that a conjugate linked via two DNA A nucleosides is more efficiently metabolized than a conjugate linked via one DNA A nucleoside. Additional studies with different anti-miR-103/107 compounds were performed, and confirmed that for anti-miR-103/107 compounds, the presence of two DNA A nucleosides leads to more efficient cleavage than a single DNA A nucleoside.

The compounds were tested for efficacy in the DIO model. As noted above, compound 12743, an unconjugated anti-miR, resulted in improved insulin sensitivity in the DIO model. Compound 19843 is a GalNAc-conjugated version of compound 12743 (see Table above), and was tested in the same study as described above for compound 12743.

Previous studies (Trajkovski et al., Nature 2011) suggested that the improvements in insulin sensitivity following miR-103/107 inhibition were driven mainly by activity in adipocyte tissue, rather than in liver tissue. Further, miR-103 and miR-107 are most highly expressed in adipose tissue and brain tissue, with low levels found in liver tissue. As the GalNAc conjugation biases delivery of a compound to the liver tissue (e.g., hepatocytes), it was surprisingly observed that conjugation to GalNAc resulted in a 3-5 fold improvement in efficacy, as determined by improvement in insulin sensitivity (FIG. 3, 2 week data for compound 19843; FIG. 4, 3 week data for compound 19843). Liver triglycerides were also reduced in a statistically significant manner.

Metabolites of the GalNAc-conjugated compounds were measured, and a metabolite retaining a 3' A was observed. As the presence of a 3'A could result in a compound having a higher affinity towards a member of the miR-15 family, the metabolite containing the 3'A was tested for cross-reactivity, however was not cross-reactive.

To determine whether GalNAc conjugation of compound 97243 could improve the profile of the compound, the 2'-F/2-MOE modified anti-miR compound was conjugated to GalNAc at the 3' terminus as follows (Table C):

TABLE C

| Compound | Sequence and Chemistry (Modified Oligonucleotide or MO) | Structure |
|---|---|---|
| 47843 | $T_E G_E A_F U_F A_F G_F C_F C_F C_F U_F G_F U_F A_E{}^m C_E A_E A_F U_F G_F C_F U_F G_F{}^m C_E A_E$ (SEQ ID NO: 23) | Structure I of FIG. 2A, where $X_2$ is a phophodiester linkage, m is 2, $N_m$ is a β-D-deoxynucleoside (dA), $X_1$ is a phosphodiester linkage |

This compound also had an A in place of a U at the 3'-terminus, to determine whether introduction of this mismatch would reduce or eliminate cross-reactivity. Although the compound did exhibit efficacy in the DIO model, as measured by fasting blood glucose, fasting plasma insulin, and HOMA IR, the onset of efficacy was delayed relative to other compounds. Additionally, the compound induced expression of IFIT in an in vitro assay, and exhibited cross-reactivity with miR-16, despite the presence of the A nucleobase at the 3' terminus. Thus, this compound, like the unconjugated compound 97243, was not considered a suitable candidate for a therapeutic agent.

Compounds 12743 and 19843, which were efficacious in the DIO model, did exhibit cross-reactivity with miR-16. In view of this, additional compounds (as shown in Table D) were designed with an A in place of a U at the 3' terminus of the anti-miR. Due to this unexpected improvement in efficacy following conjugation to GalNAc, these additional compounds were also conjugated to GalNAc at the 3' terminus. The anti-miR portion of compound 45943 is a 9 nucleoside portion of compound 12743 and 19843, which was also conjugated to GalNAc.

TABLE D

| Compound | Sequence and Chemistry (Modified Oligonucleotide or MO) | Structure |
|---|---|---|
| 45943 | $^mC_EA_SATG_SCTG_SC_S$<br>(a 9 nucleoside portion of 12743)<br>(SEQ ID NO: 24) | Structure I of FIG. 2A, where $X_2$ is a phophodiester linkage, m is 1, $N_m$ is a β-D-deoxynucleoside (dA), $X_1$ is a phosphodiester linkage |
| 47043 | $C_SA_SA_SU_SG_SC_SU_SG_SC_SA_S{}^OA^OA^OC_SA_SA_SU_SG_SC_SU_SG_SC_SA_S$<br>(SEQ ID NO: 7) | Structure I of FIG. 2A, where $X_2$ is a phophodiester linkage, m is 2, $N_m$ is a β-D-deoxynucleoside (dA), $X_1$ is a phosphodiester linkage |
| 39243 | $C_SA_SA_SU_SG_SC_SU_SG_SC_SA_S$<br>(SEQ ID NO: 6) | Structure I of FIG. 2A, where $X_2$ is a phophodiester linkage, m is 2, $N_m$ is a β-D-deoxynucleoside (dA), $X_1$ is a phosphodiester linkage |

Compounds 45943 and 47043 were tested in the DIO model.

Figure 3:
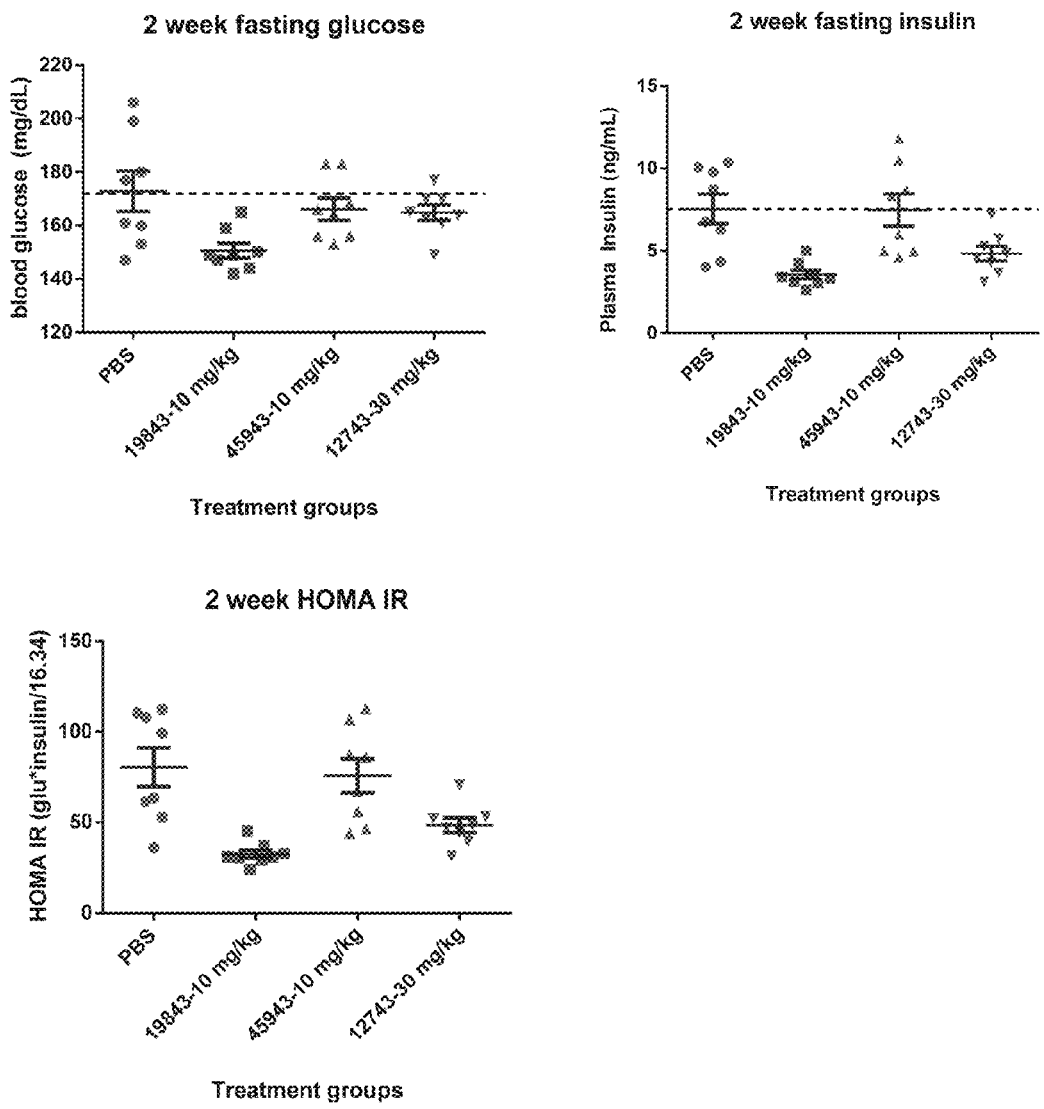
FIG. 3 shows fasting glucose, fasting insulin, and HOMA IR at 2 weeks in mice administered the indicated compound, as described in the Examples.
Figure 4:
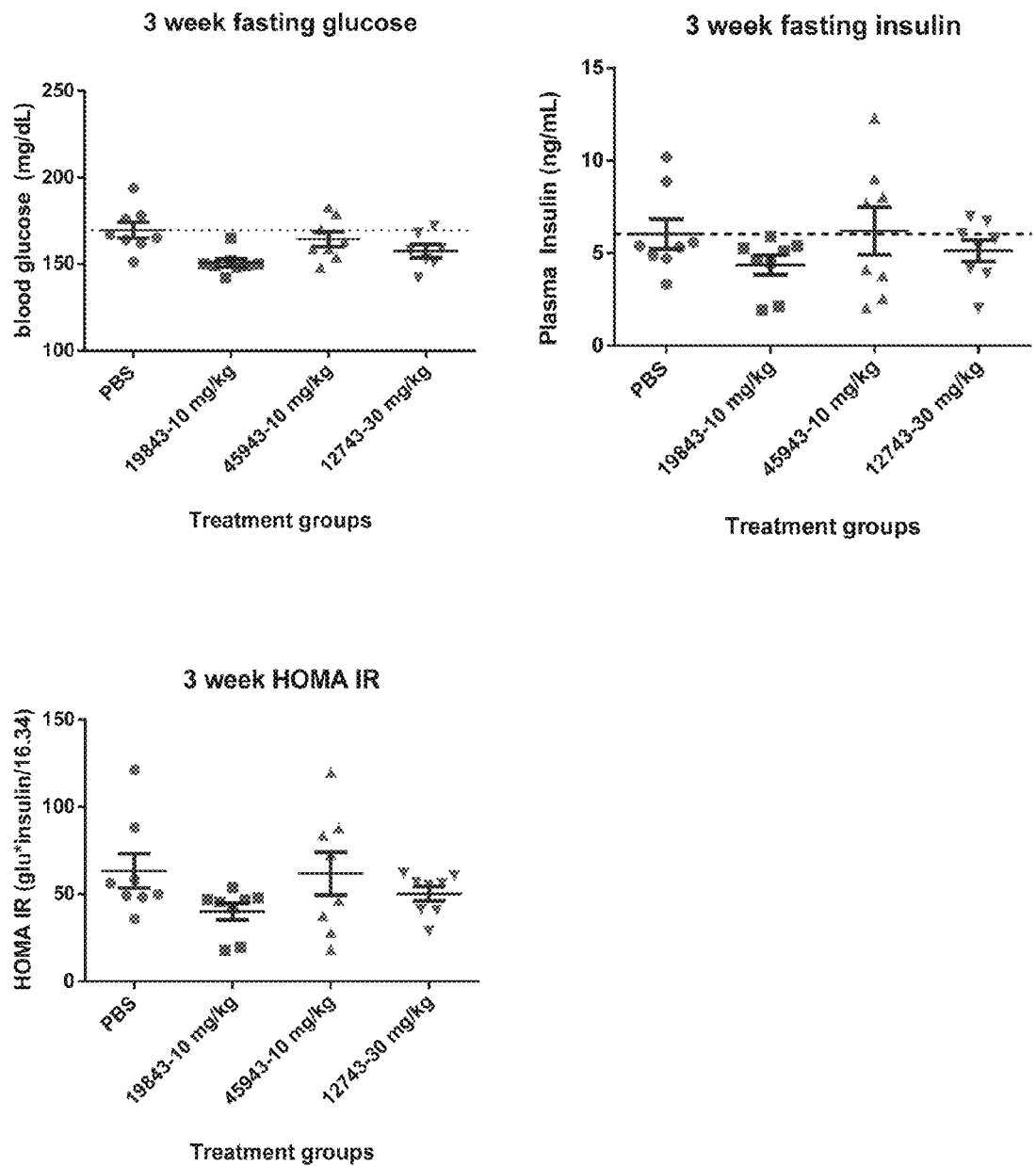
FIG. 4 shows fasting glucose, fasting insulin, and HOMA IR at 3 weeks in mice administered the indicated compound, as described in the Examples.

As shown in FIGS. 3 and 4 compound 45943 did not reduce fasting glucose, fasting insulin, or improve HOMA IR at 2 weeks or 3 weeks. Liver triglycerides were not reduced. Thus, this chemically modified, 9-nucleoside anti-miR conjugated to GalNAc was not efficacious in a mouse model of insulin resistance. Thus, a truncated version of the active compound 12743 did not retain activity.

Compound 47043 was tested as follows. C57BL/6 mice were fed a high-fat diet (60% kcal from fat) for ~15 weeks. Groups of 8 mice each were treated as follows: (1) PBS; (2) compound 47043 at 3 mg/kg; (3) compound 47043 at 10 mg/kg.

Figure 5:
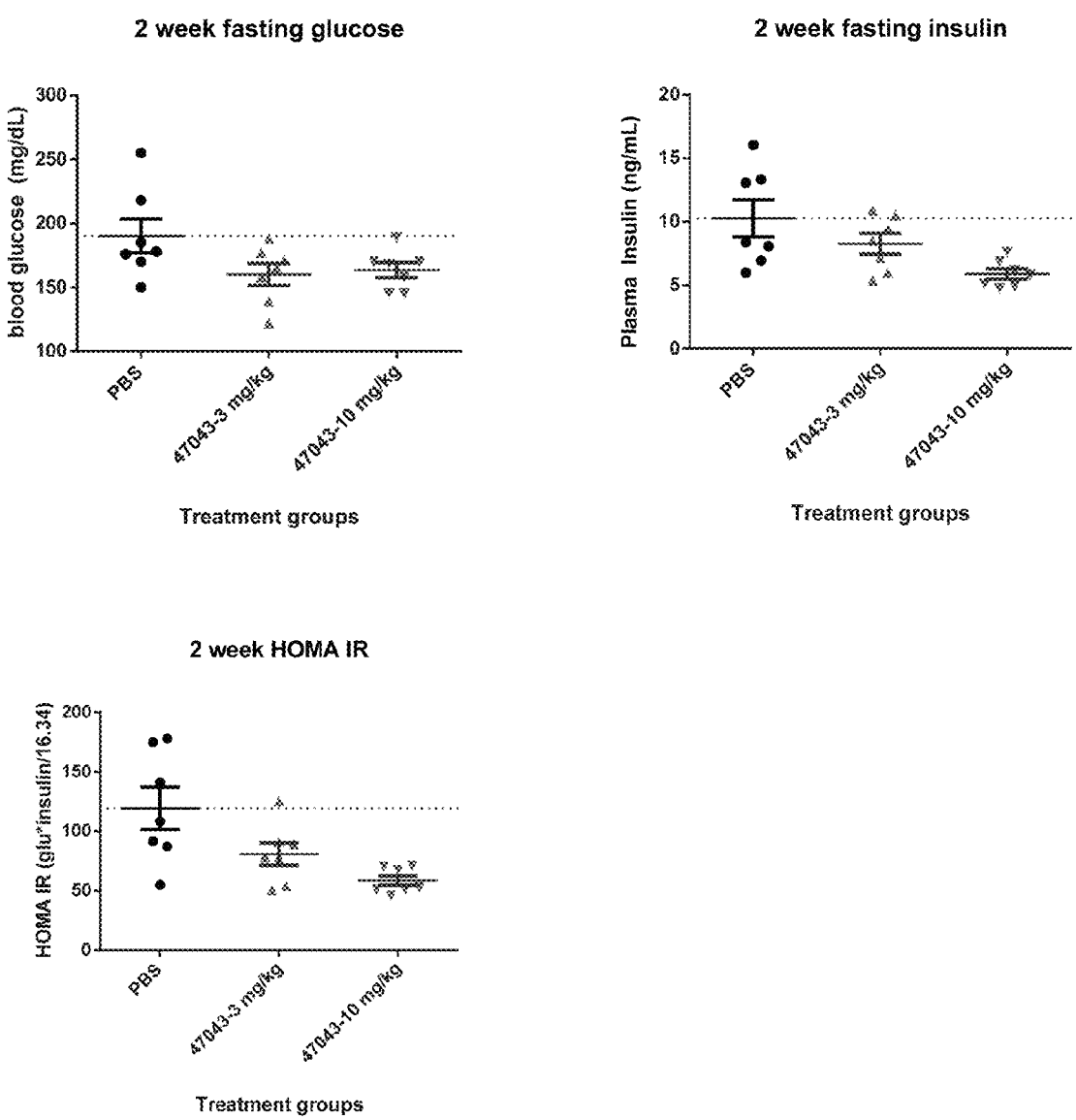
FIG. 5 shows fasting glucose, fasting insulin, and HOMA IR at 2 weeks in mice administered the indicated compound, as described in the Examples.
Figure 6:
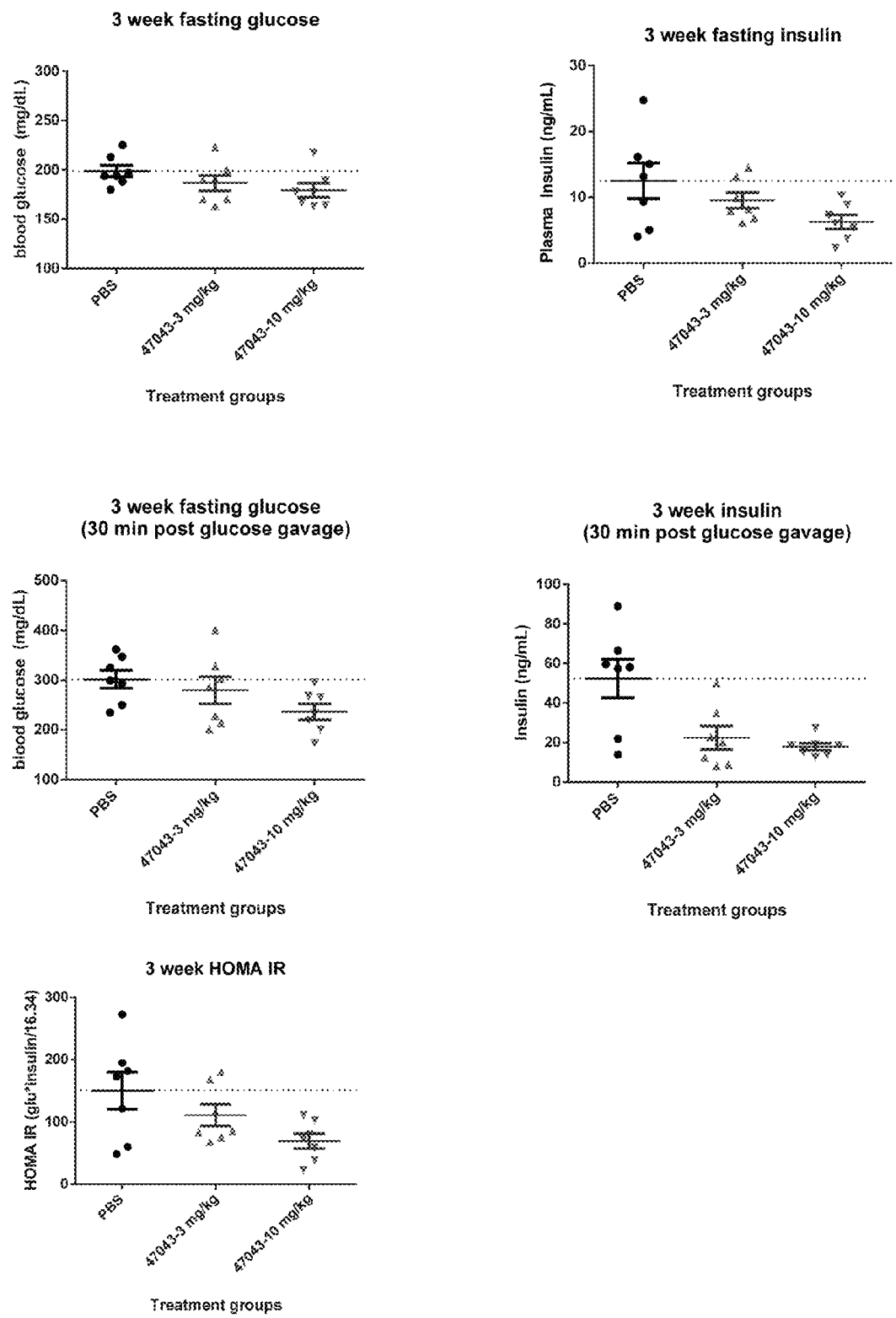
FIG. 6 shows fasting glucose, fasting insulin, and HOMA IR at 3 weeks in mice administered the indicated compound, as described in the Examples.
Figure 7:
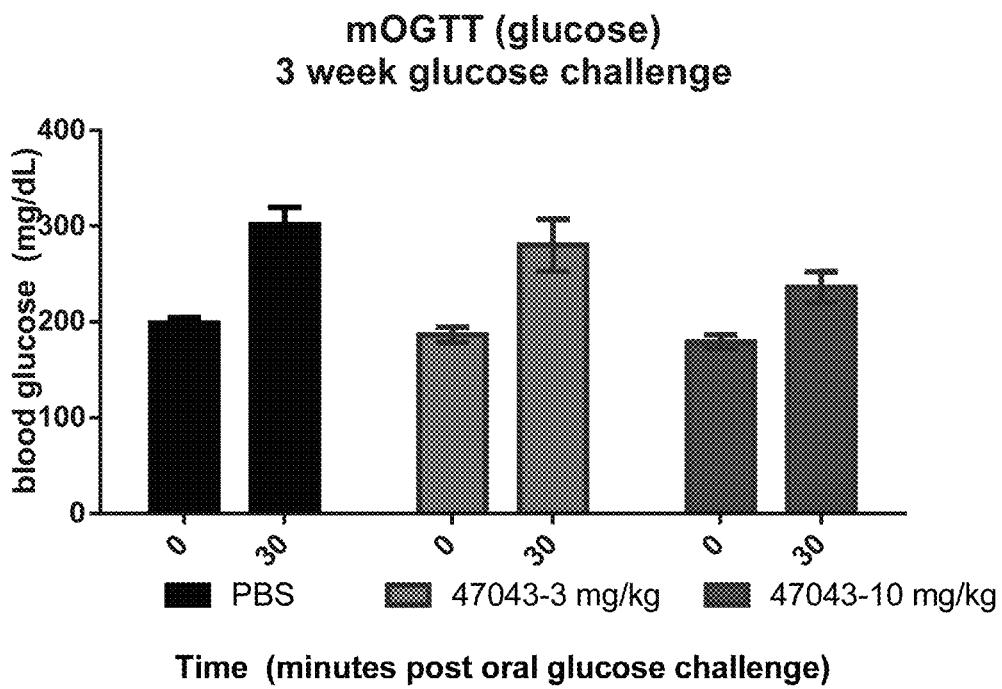
FIG. 7 shows blood glucose and plasma insulin following oral glucose challenge in mice administered the indicated compound, as described in the Examples.
Figure 7:
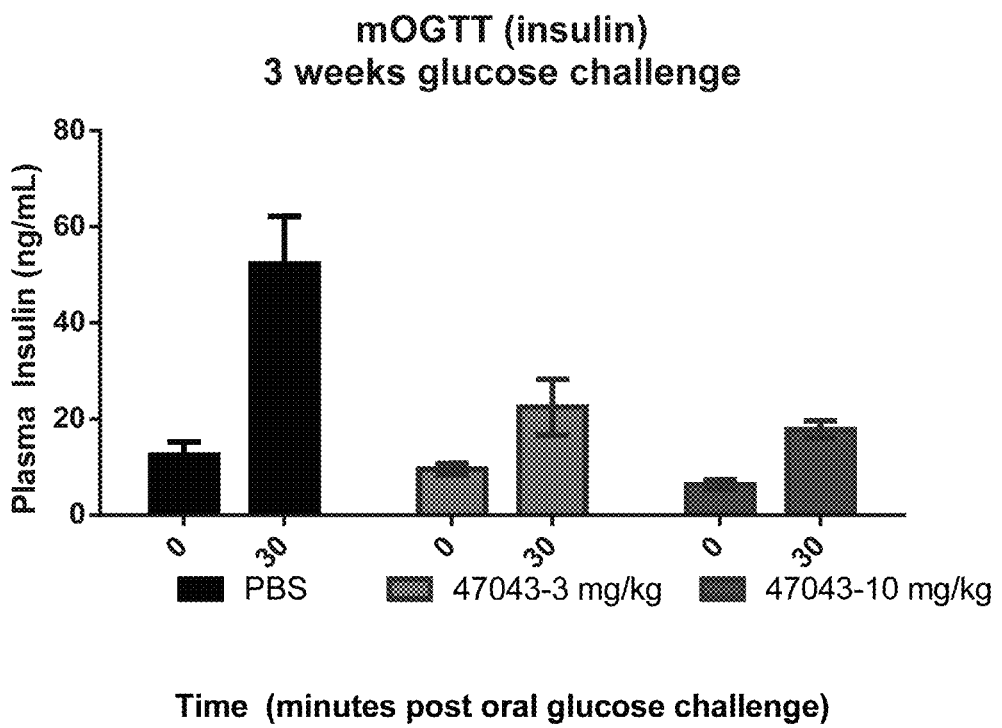

One day prior to treatment, blood was collected after a 4 hour fast, and animals were sorted into treatment groups. Treatments were administered once weekly, by subcutaneous injection, for a 7 treatments (days 0, 5, 13, 19, 26, 33, and 36 of the study, with day 0 being the day of the first treatment). Blood was collected weekly after a 4-6 hour fast on days 8, 15, 21, 28, and 32 of the study, for measurements of fasting glucose and fasting insulin. On day 21 (or the end of week 3) of the study, a oral glucose tolerance test (OGTT) was performed following a 4 hour fast, with blood collections just prior to and 30 minutes following administration of oral glucose Animals were sacrificed on day 39 of the study. As shown in FIGS. 5, 6, and 7, compound 47043 exhibited significant efficacy in the DIO model, at a dose as low as 3 mg/kg, as determined by reductions in fasting glucose, fasting insulin, and HOMA IR, which together indicate improved insulin sensitivity. Additionally, as shown in FIGS. 6 and 7, oral glucose tolerance was improved following treatment with compound 47043.

Figure 8:
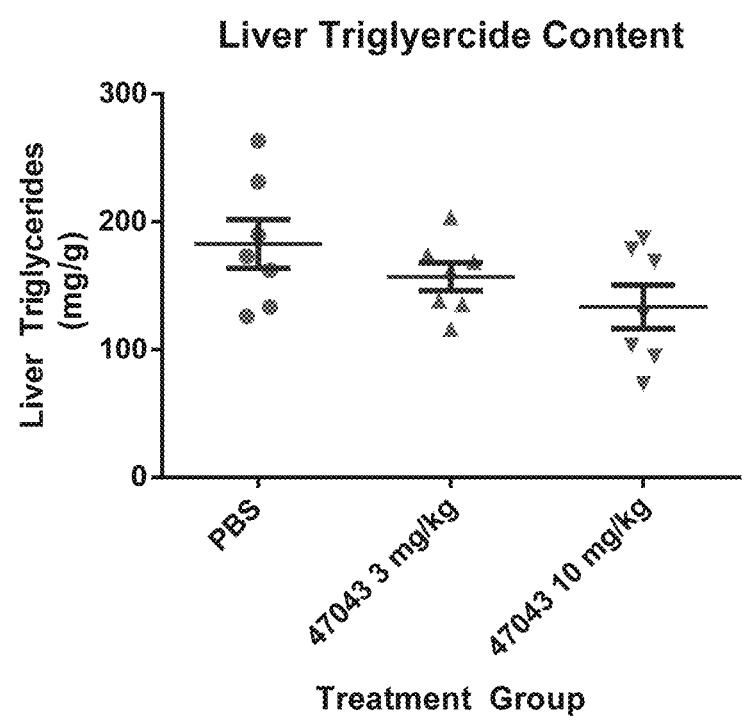
FIG. 8 shows liver triglyceride content in mice administered the indicated compound, as described in the Examples.

Liver triglyceride content was also measured in the DIO mice treated with 47043. Triglyceride was extracted from the liver with acetone, and measured by colorimetric assay (Infinity Triglyceride Liquid Reagent). As shown in FIG. 8, liver triglyceride content was reduced following treatment with compound 47043, relative to treatment with PBS.

As treatment with compound 47043 resulted in a significant improvement in insulin sensitivity, it was tested for cross-reactivity with miR-16. Consistent with the observation that an anti-miR with an A in place of a U at the 3' terminus is not cross-reactive, no cross-reactivity was observed between compound 47043 and miR-16.

Compound 47043 was further evaluated in a safety study. Wild-type mice were injected with a single, 300 mg/kg dose of compound. Three days after the injection, mice were sacrificed, and tissues and blood were collected. IFIT and OASL mRNA levels were measured in liver tissue. Spleen weight was measured for comparison to body weight. ALT levels in blood were measured. Compound 47043 did not exhibit increases in IFIT, OASL, spleen weight or ALT. Other compounds targeted to miR-103/107, with different anti-miR structures (e.g. number and placement of sugar modifications) did exhibit increases in these safety parameters.

The viscosity of compound 47043 was measured. Below a concentration of 230 mg/g, viscosity was below 20 cP, permitting a dosing solution concentration of approximately 200 mg/mL, which could be administered via a subcutaneous injection. Conversely, compounds with different anti-miR structures (e.g. number and placement of sugar modifications) were highly viscous, making it difficult for the compound to be administered via a subcutaneous injection. These data further demonstrate that the structure of the anti-miR (type, number and placement of sugar modifications) affects its viscosity, which is an important consideration in choosing a compound that can be administered via a subcutaneous injection.

The intended active metabolite of 47043 is the full cEt 10-mer ($C_SA_SA_SU_SG_SC_SU_SG_SC_SA_S$; SEQ ID NO: 6). The pharmacokinetic profile of compound 47043 was also evaluated in wild-type mice to determine (1) how efficiently the anti-miR is cleaved from the conjugate; (2) how efficiently the adjacent cEt 10-mers are released; (3) whether DNA A nucleosides remain attached to the full cEt 10-mer; and (4) the stability of the intended active metabolite. Seven days following subcutaneous administration of a single dose of compound 47043, liver and kidney tissues and plasma were collected for measurement of the parent compound and metabolites. It was observed that in the liver, 90% of the compound was metabolized to the cEt 10-mer (approximately 22%) or a cEt 10-mer with a DNA A (either at the 5' end or 3' end of the 10-mer; approximately 67%). In the kidney, approximately 50% of the compound was metabolized to the cEt 10-mer or cEt 10-mer with a DNA A (either at the 5' end or 3' end of the 10-mer). Oligonucleotides generally accumulate to the highest levels in kidney tissue, followed by liver tissue. For compound 47043, the kidney to liver ratio was 0.5. In contrast, compounds with different anti-miR structures exhibited different metabolic products, and in some cases a higher kidney to liver ratio. For example, an anti-miR that was 19 nucleosides in length, with cEt, 2'-MOE and DNA sugar moieties, was susceptible to metabolism in the middle of the compound, due to the presence of three DNA nucleosides. Cleavage at this position metabolized the intended active metabolite (the full 19-mer), resulting in reduced efficacy. This compound also exhibited a higher kidney to liver ratio of 1.5.

Based on the efficacy and safety data, compound 47043 was identified as a candidate agent for the improvement of insulin sensitivity and reduction of liver triglycerides.

Example 4

DIO Efficacy Studies

To further evaluate compound 47043, additional dosages of compound were tested in the DIO mouse model.

C57BL/6 mice were fed a high-fat diet (60% kcal from fat) for ~15 weeks. Groups of 8 mice each were treated as follows: (1) PBS; (2) compound 47043 at 1.7 mg/kg; (3) compound 47043 at 5 mg/kg; (4) compound 47043 at 15 mg/kg; and (5) compound 47043 at 45 mg/kg. A group of 4 normal (lean) mice was used as an additional control group.

Prior to initiation of dosing, blood was collected after a 4 hour fast, and animals were sorted into treatment groups based on fasting glucose, fasting insulin and body weight. Treatments were administered once weekly, by subcutaneous injection, for a total of 7 doses. 10 days following the first dose (after two doses), and weekly thereafter for the remainder of the study, blood was collected after a 4-6 hour fast for measurements of fasting glucose and fasting insulin Animals were sacrificed three days after the seventh and final dose of the study. Fasting glucose and fasting insulin were used to calculate HOMA-IR after 1, 2, 3, 4, and 5 weeks of treatment. An oral glucose tolerance test (OGTT) was performed at after 5 weeks of treatment. In this OGTT, blood was collected at a single timepoint, at 30 minutes after the oral glucose administration, rather than over multiple timepoints, to permit the measurement of insulin which requires a larger volume of blood. At the end of the study, liver tissue was collected for measurement of liver triglycerides.

Figure 9A:
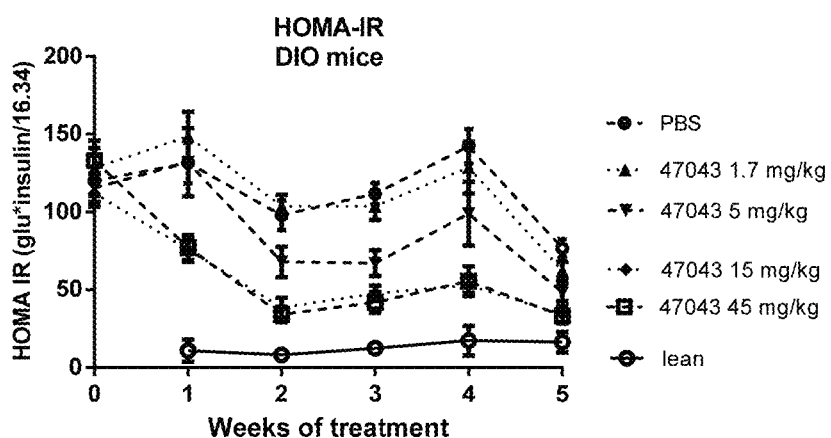
FIG. 9A-E shows improvements in insulin sensitivity, and triglyceride reductions in DIO mice administered the indicated compound, as described in the Examples.

As shown in FIG. 9A, as assessed by weekly HOMA-IR, compound 47043 improved insulin sensitivity in a dose-responsive manner.

Figure 9B:
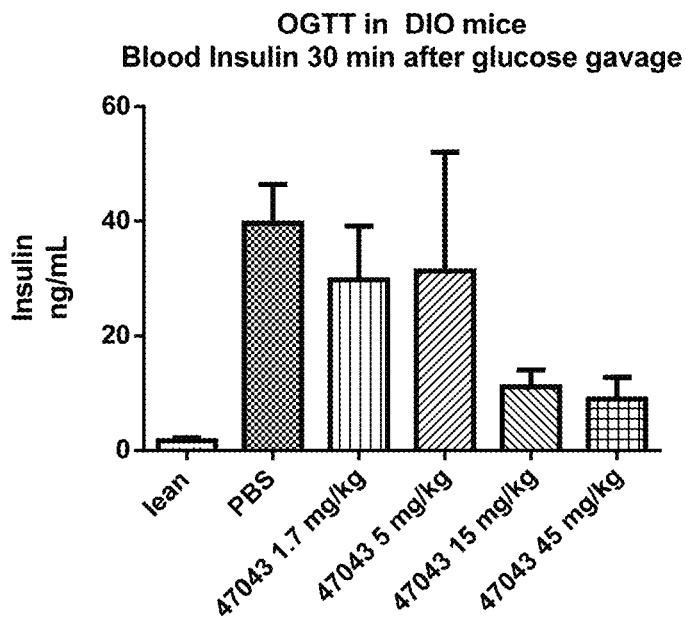
Figure 9C:
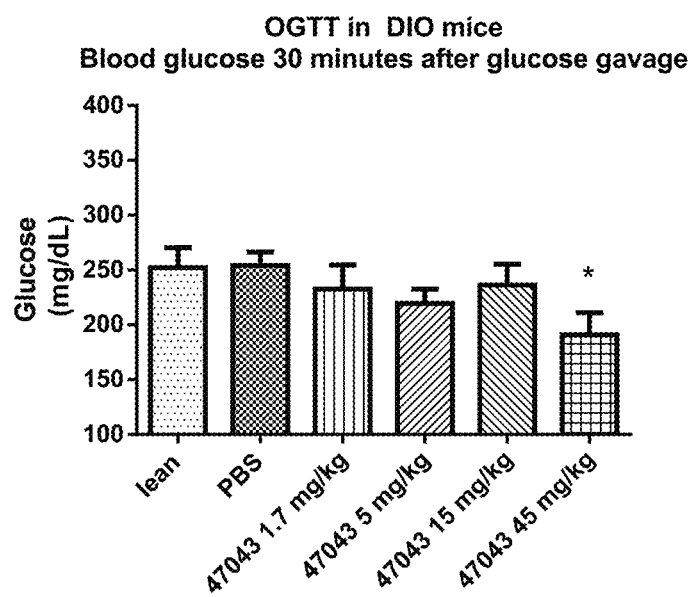

As shown in FIG. 9B, treatment with compound 47043 resulted in increased insulin sensitivity, as evidenced by the reduced amount of insulin secreted, particularly at the higher doses of compound, in response to the glucose challenge. A trend toward reduced blood glucose levels was observed, indicating an improvement in the ability of the body to clear glucose after the oral administration (FIG. 9C).

Figure 9D:
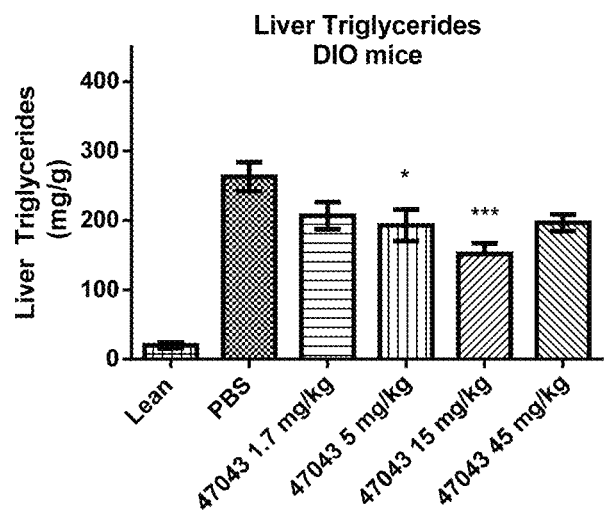

Liver triglyceride content was also measured. Triglyceride was extracted from the liver with acetone, and measured by colorimetric assay (Infinity Triglyceride Liquid Reagent). As shown in FIG. 9D, a trend towards reduced liver triglyceride content was observed following 5 weeks of treatment with compound 47043, relative to treatment with PBS.

Figure 9E:
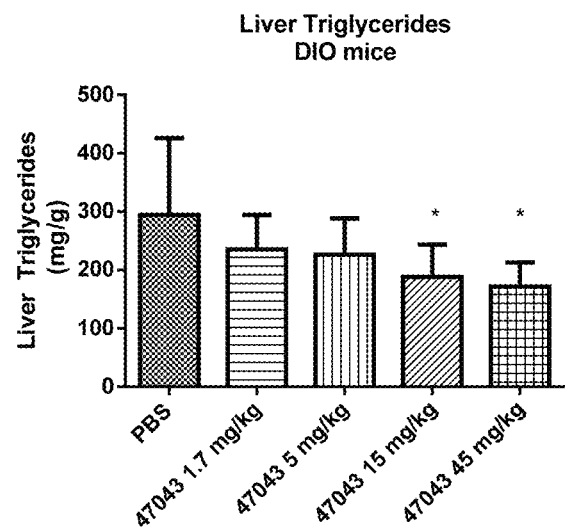

Liver triglycerides were also measured in an independent DIO study, and after 10 weeks of treatment a trend toward lowered triglycerides was observed in this study as well, with statistically significant reductions at the 15 mg/kg and 45 mg/kg doses (FIG. 9E).

To test the effects of a single dose of compound 47043, an additional study was performed in the DIO model, with mice treated as follows: (1) PBS; (2) compound 47043, 10 mg/kg; (3) compound 47043, 30 mg/kg; (4) compound 47043, 60 mg/kg; (5) compound 47043, 100 mg/kg. Mice were sorted into groups of 8 based on body weight, fasting glucose, fasting insulin and HOMA-IR. A single dose of PBS or compound was administered, and after one week blood was collected following a 4 hour fast. Fasting plasma insulin and fasting plasma glucose were used to calculate HOMA-IR.

Figure 10:
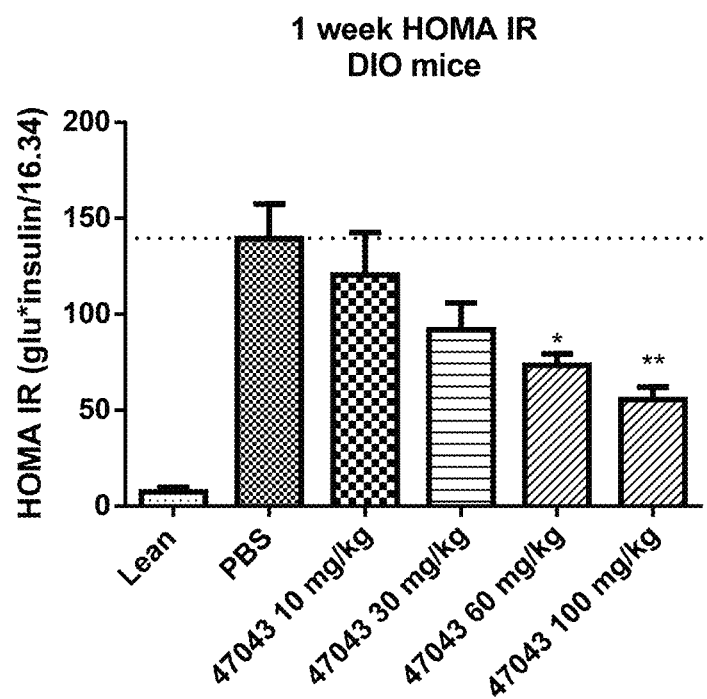
FIG. 10 shows HOMA IR at 1 week in mice administered the indicated compound, as described in the Examples.

As shown in FIG. 10, after a single dose of compound 47043, statistically significant reductions in HOMA-IR were observed.

Example 5

Db/Db Efficacy Study

The inhibition of miR-103/107 in the db/db model, a genetic model of obesity, diabetes, and dyslipidemia.

Compound 47043 was tested as follows. db/db mice (Jackson Laboratories) approximately 7 weeks of age were sorted into treatment groups based on bodyweight, fasting insulin and fasting glucose. Mice were fed a normal rodent chow diet throughout the study. Groups of 8 mice each were treated as follows: (1) PBS; (2) compound 47043 at 10 mg/kg twice weekly (3 or 4 days between doses); (3) compound 47043 at 30 mg/kg twice weekly (3 or 4 days between doses); (4) compound 47043 at 30 mg/kg once weekly. Treatment was continued for 9 weeks. Blood was collected for glucose measurements after a 4 hour fast on a weekly basis, beginning 1 week after the twice weekly treatment groups has received 2 doses and the once weekly treatment group had received 1 dose. In this study, insulin levels were not measured, as insulin levels are not a reliable indicator of improvements insulin sensitivity in the db/db model, due to the possibility of beta cell failure occurring in the animals. At the end of the study, liver tissue was collected for measurement of liver triglycerides.

Figure 11A:
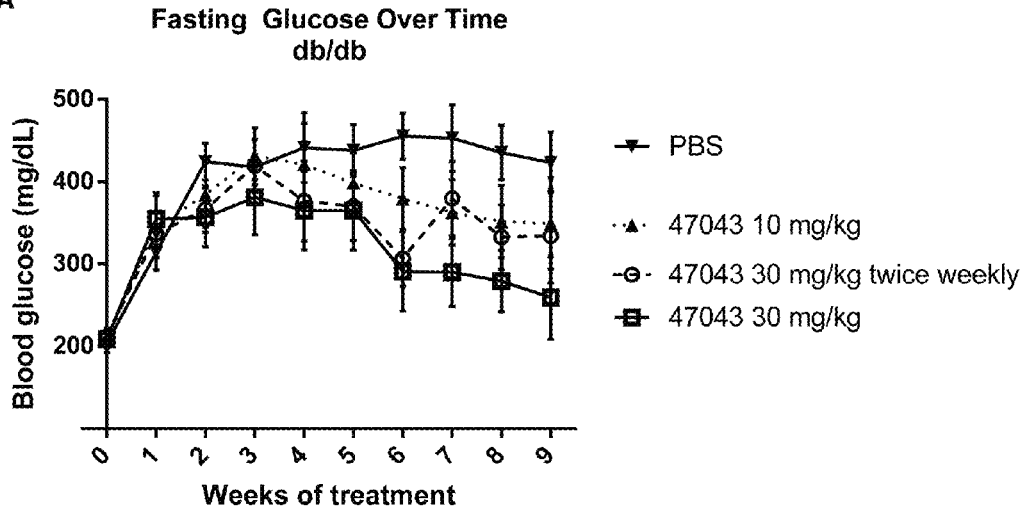
FIG. 11A-B shows fasting glucose and liver triglycerides in db/db mice administered the indicated compound, as described in the Examples.

As shown in FIG. 11A, as expected due to the increasing severity of disease over time in the db/db model, the PBS-treated mice exhibited increased fasting glucose levels throughout the course of the study. In contrast, fasting glucose levels in db/db mice treated with compound 47043 not only did not increase, the fasting glucose levels decreased during the study. Thus this study demonstrated that treatment with compound 47043 reversed the severe hyperglycemia that the db/db mice develop with age. Due to the rapid disease progression of this model, two treatment groups included twice weekly dosing. However, the 30 mg/kg dose showed similar efficacy for both weekly and twice weekly dosing.

Figure 11B:
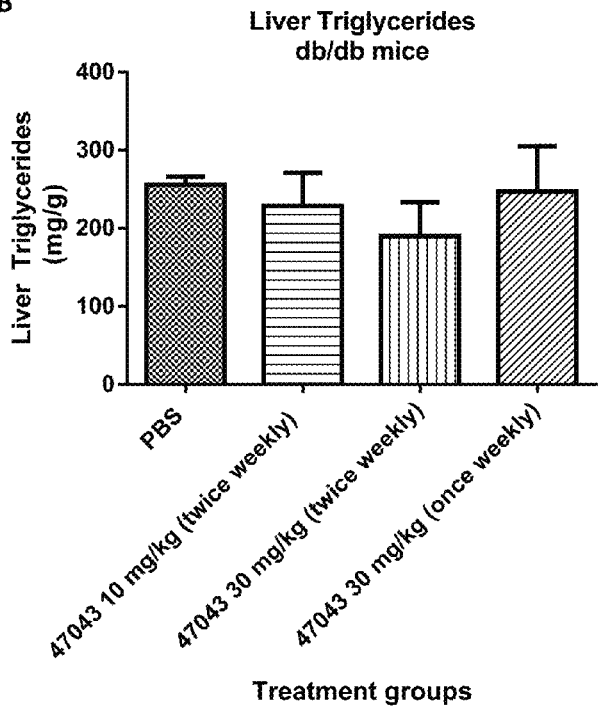

Liver triglyceride content was also measured. Triglyceride was extracted from the liver with acetone, and measured by colorimetric assay (Infinity Triglyceride Liquid Reagent). As shown in FIG. 11B, a trend towards reduced liver triglyceride content was observed following treatment with compound 47043, relative to treatment with PBS.

This study confirmed the efficacy of compound 47043 in a different model of diabetes, in addition to the DIO model.

Example 6

Hyperinsulinemic Euglycemic Clamp Assay in DIO Model

Insulin sensitivity may be evaluated using a hyperinsulinemic euglycemic clamp assay. In this assay, catheterized mice receive an infusion of glucose and insulin. The insulin is infused at a constant high level (hyperinsulinemic), while the glucose is infused at a variable rate to maintain blood glucose at a constant, normal (euglycemic) level. The rate of glucose infusion indicates the sensitivity to insulin, e.g. an increased glucose infusion rate indicates an increased sensitivity to insulin. For a DIO mouse, fed a high fat diet for 20 weeks, a typical infusion rate is 5-10 mg/kg/min. For a normal mouse, fed a normal diet for 24 weeks, a typical infusion rate is 30-40 mg/kg/min.

Figure 12A:
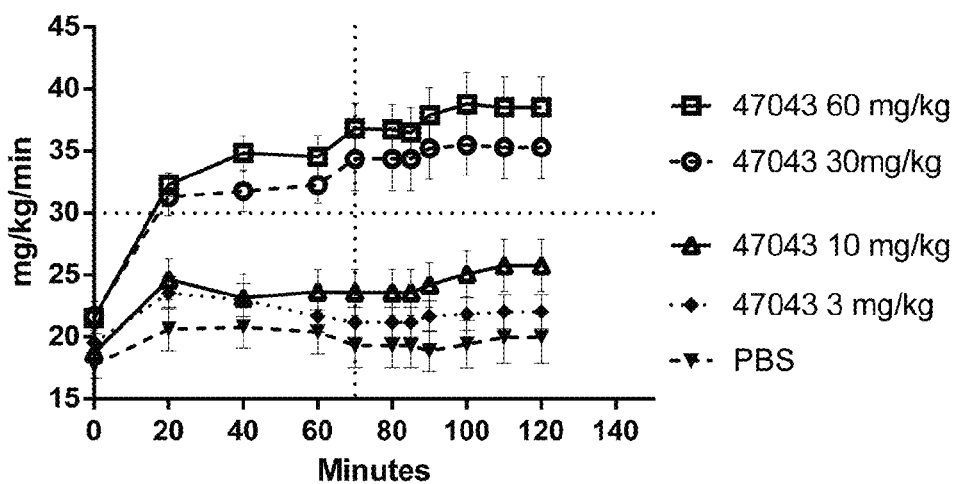
Figure 12B:
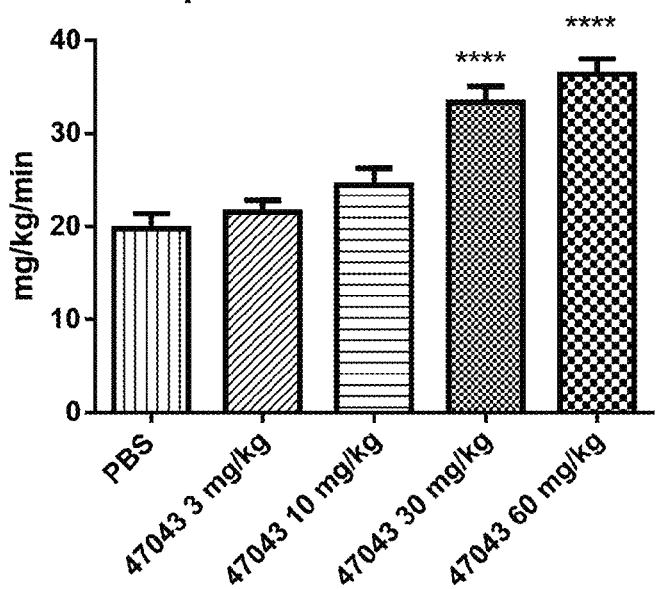
Figure 12C:
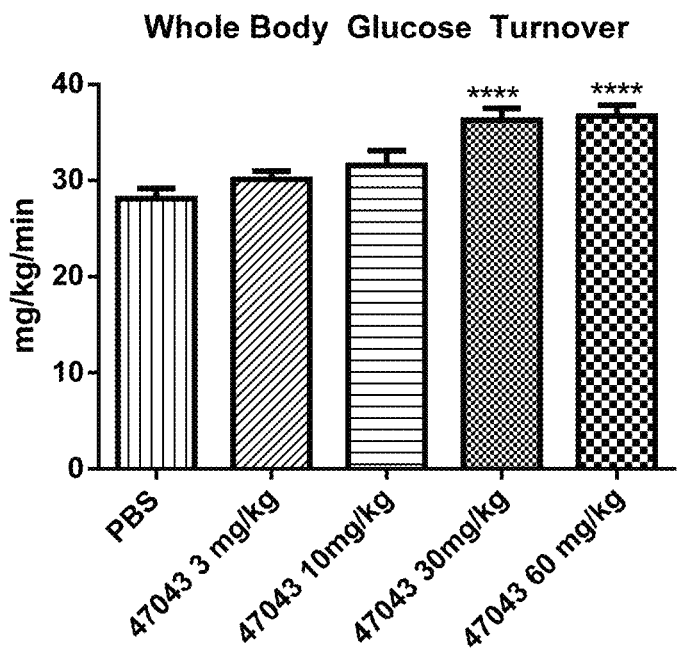
Figure 12D:
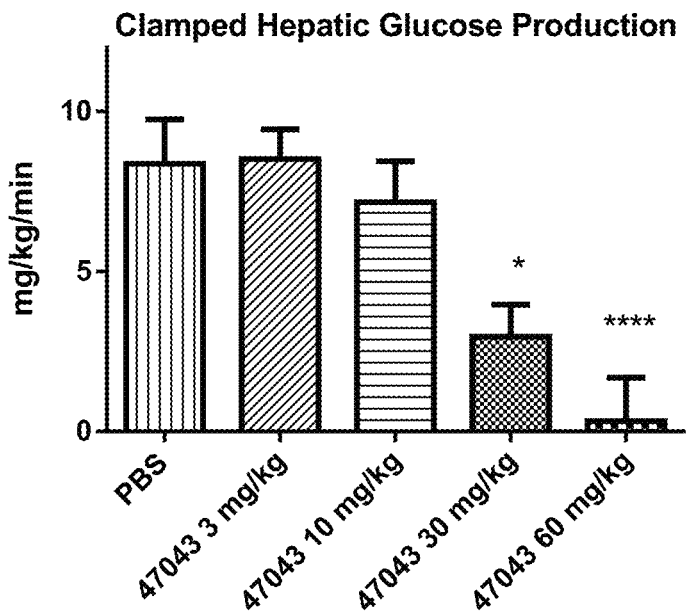
Figure 12E:
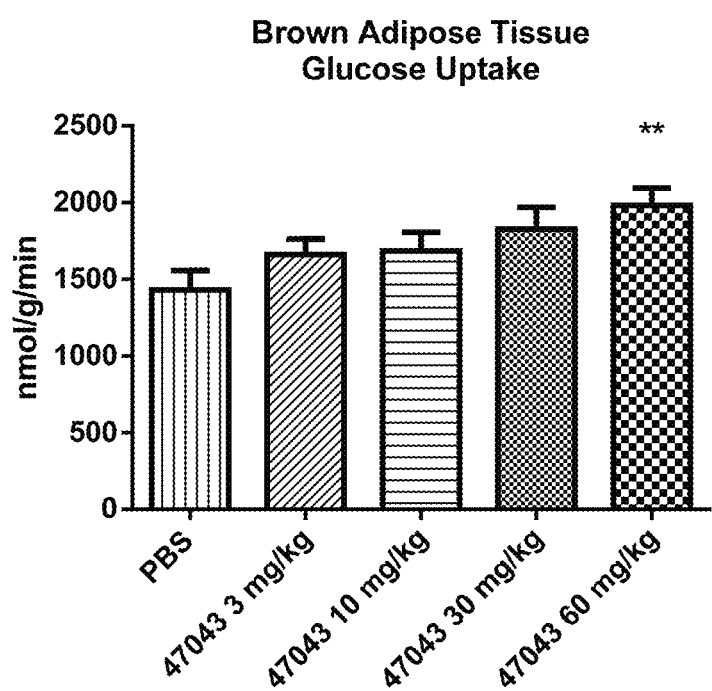

Compound 47043 was tested in the clamp assay, in DIO mice. Mice approximately 21 weeks of age were assessed for baseline fasting glucose, fasting insulin and body composition, after a 6 hour fast. Mice were placed into groups of 13 to 14 mice each, for treatment as follows: (1) PBS; (2) compound 47043, 3 mg/kg; (2) compound 47043, 10 mg/kg; (3) compound 47043, 30 mg/kg; compound 47043, 60 mg/kg. Treatments were administered subcutaneously, once per week for a total of 5 doses. The clamp procedure was performed 24 hours after the fifth and final dose, and after an overnight fast. Insulin was infused at a constant rate of 4 mU/kg/min. The parameters measured included glucose infusion rate at 20 minute intervals over the entire 120 minute infusion period (FIG. 12A); clamped glucose infusion rate, which is the average glucose infusion rate during the 'clamped' portion of the infusion period, when glucose infusion rate has stabilized, from the 70 minute to 120 minute timepoints (FIG. 12B); whole body glucose turnover (FIG. 12C); clamped hepatic glucose production, (FIG. 12D); and brown adipose glucose uptake (FIG. 12E).

As shown in FIG. 12, treatment with compound 47043 resulted in a dose-responsive improvement in glucose infusion rate, indicating an increase sensitivity to insulin (i.e., the body has a greater capacity to handle increased amounts of glucose). Additionally, whole body glucose turnover was improved. Hepatic glucose production was decreased, while brown adipose glucose uptake was increased, suggesting that the liver and peripheral tissues (e.g. adipose) contribute to the improvements in insulin sensitivity.

This results of this provide further evidence that compound 47043 is improving insulin sensitivity.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

---

What is claimed:

1. A compound comprising the structure:

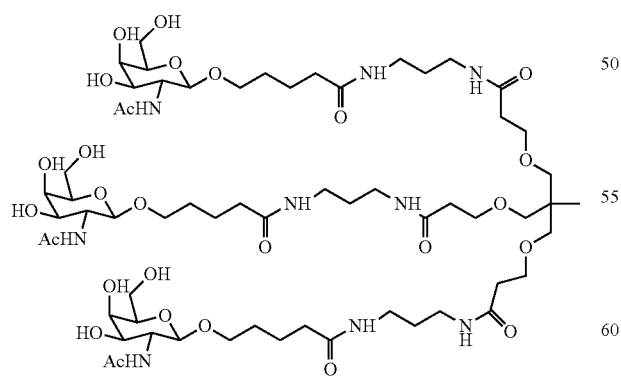

(II)

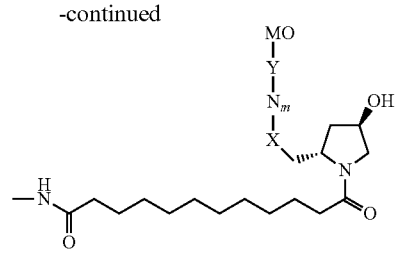

wherein X is a phosphodiester linkage; each N of $N_m$ is a deoxyadenosine (A); m is 2; Y is a phosphodiester linkage; and MO is 5'-$C_SA_SA_SU_SG_SC_SU_SG_SC_SA_SAAC_SA_SA_SU_SG_SC_SU_SG_SC_SA_S$-3' (SEQ ID NO: 7), wherein each nucleoside followed by a subscript "S" is a S-cEt nucleoside, each nucleoside not followed by a subscript is a deoxynucleoside, and each internucleoside linkage between two S-cEt nucleosides is a phosphorothioate linkage, and the remaining internucleoside linkages are phosphodiester linkages; and wherein Y is linked to the 3' terminus of MO; or a pharmaceutically acceptable salt thereof.

2. A compound having the structure:
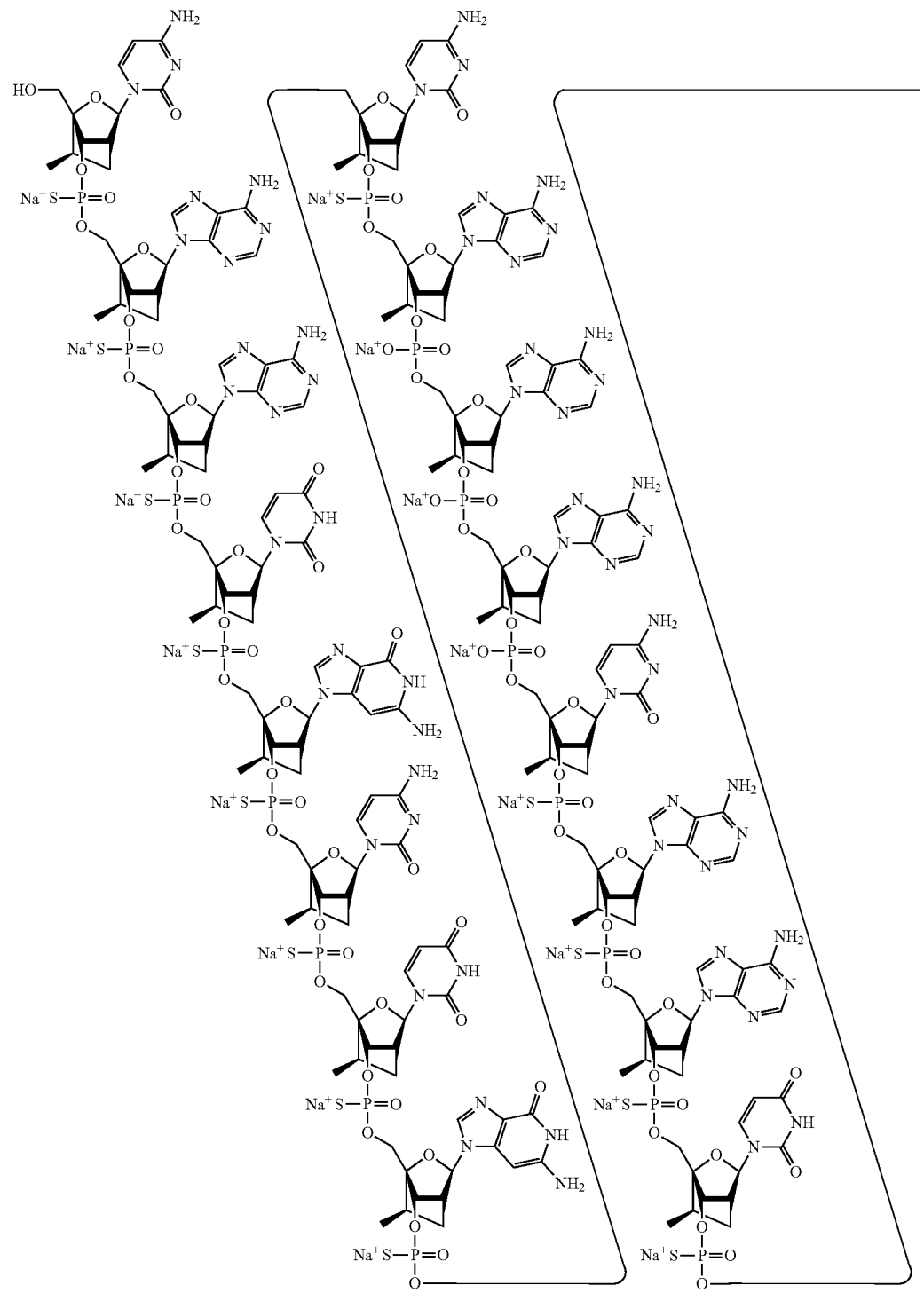

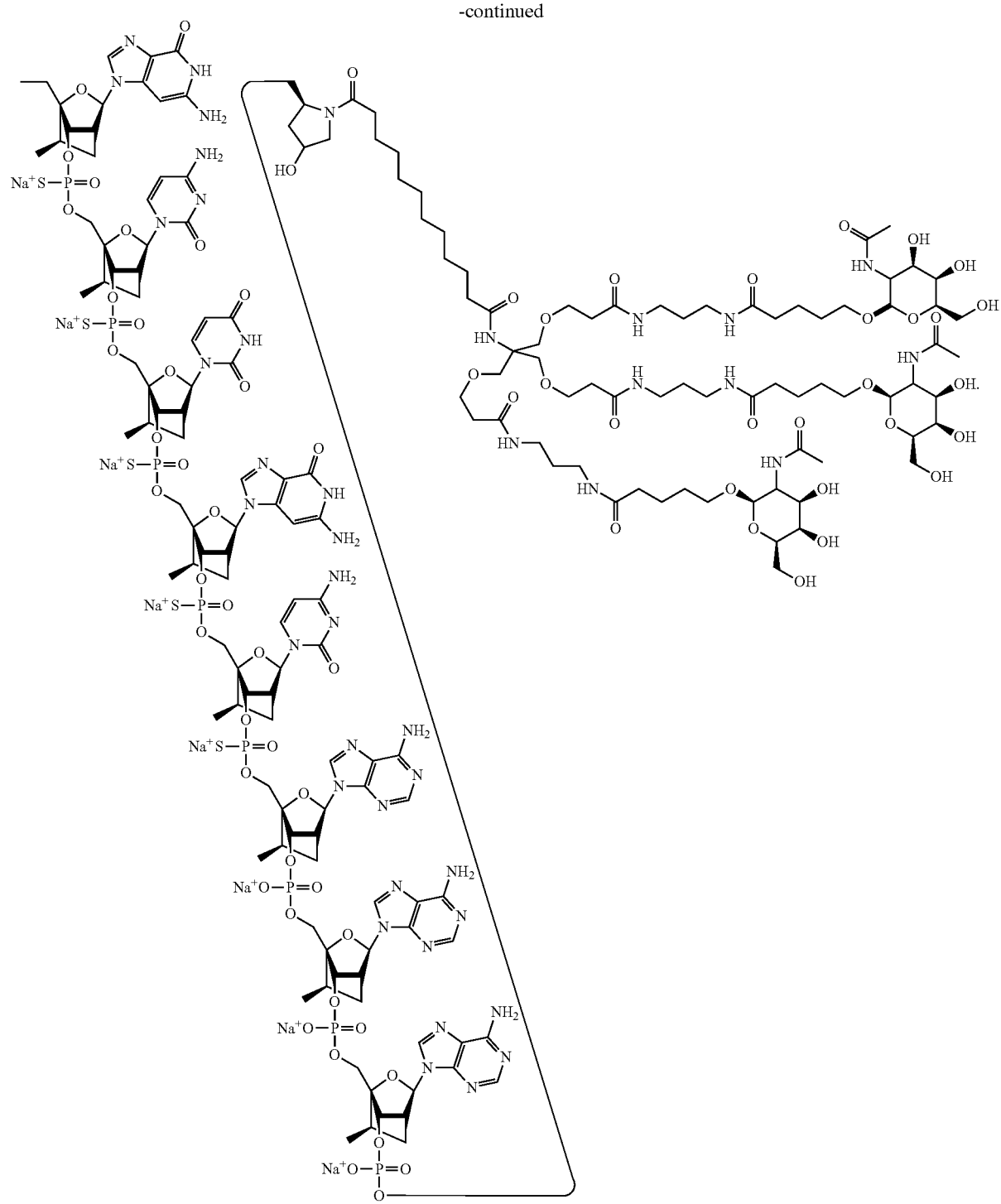

3. A pharmaceutical composition comprising a compound of claim 1 and a pharmaceutically acceptable carrier.

4. The pharmaceutical composition of claim 3, which is an aqueous composition.

5. The pharmaceutical composition of claim 3, which is a lyophilized composition.

6. A pharmaceutical composition comprising a compound of claim 2 and a pharmaceutically acceptable carrier.

7. The pharmaceutical composition of claim 6, which is an aqueous composition.

8. The pharmaceutical composition of claim 6, which is a lyophilized composition.

\* \* \* \* \*

UNITED STATES PATENT AND TRADEMARK OFFICE
CERTIFICATE OF CORRECTION

PATENT NO. : 9,487,783 B2
APPLICATION NO. : 14/819648
DATED : November 8, 2016
INVENTOR(S) : Balkrishen Bhat et al.

It is certified that error appears in the above-identified patent and that said Letters Patent is hereby corrected as shown below:

In Claim 1, the structure shown at Column 119, Line 47, to Column 120, Line 46, is replaced with the following structure:

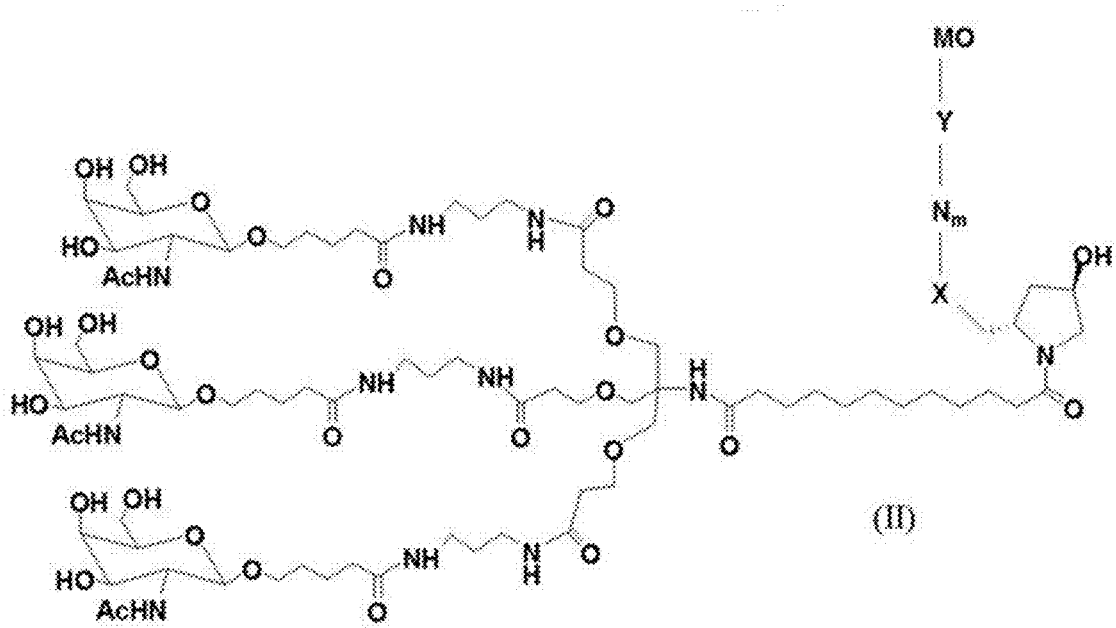

--                                                                                              --

Signed and Sealed this
Twenty-ninth Day of May, 2018

Andrei Iancu
*Director of the United States Patent and Trademark Office*

CERTIFICATE OF CORRECTION (continued) Page 2 of 2
U.S. Pat. No. 9,487,783 B2

In Claim 2, the structure shown at Column 121, Line 2, to Column 124, Line 57, is replaced with the following structure:

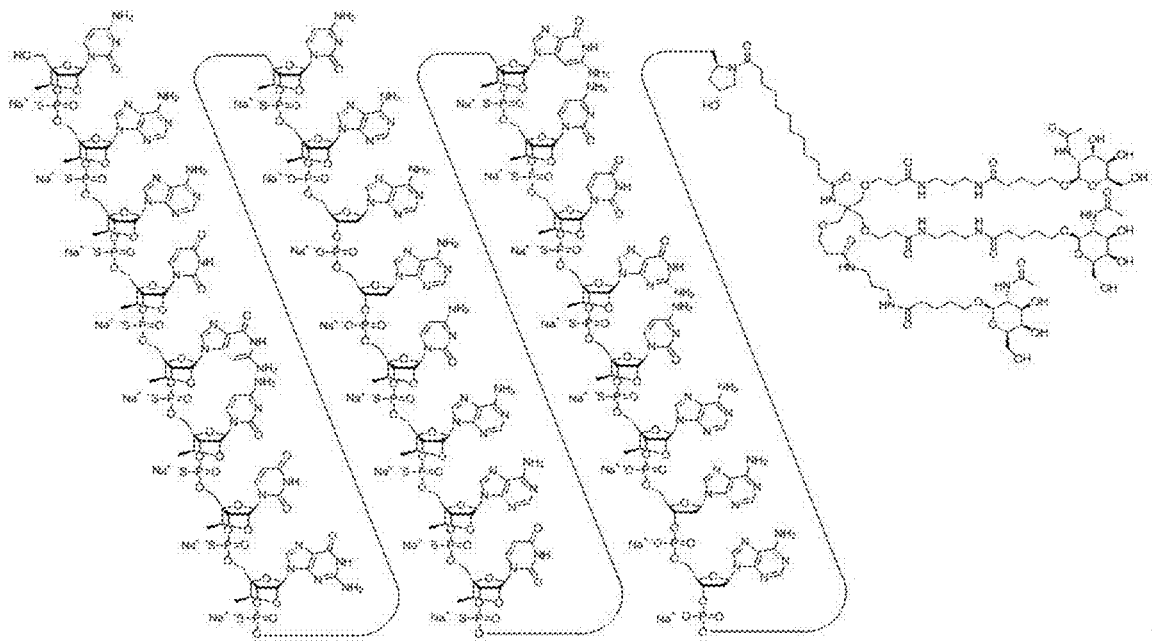

--                                                                                             --